United States Patent
Rousso et al.

(10) Patent No.: US 7,966,067 B2
(45) Date of Patent: Jun. 21, 2011

(54) APPARATUS AND METHOD FOR DELIVERING ELECTRICAL SIGNALS TO A HEART

(75) Inventors: Benny Rousso, Rishon-LeZion (IL); Netanel Eizenberg, Ramat-Gan (IL); David Prutchi, Voorhees, NJ (US); Yuval Mika, Closter, NJ (US); Yehuda Snir, Kiryat-Tivon (IL)

(73) Assignee: Impulse Dynamics NV, Curacao (AN)

( * ) Notice: Subject to any disclaimer, the term of this patent is extended or adjusted under 35 U.S.C. 154(b) by 541 days.

(21) Appl. No.: 11/991,481

(22) PCT Filed: Sep. 6, 2006

(86) PCT No.: PCT/IL2006/001042
§ 371 (c)(1),
(2), (4) Date: Mar. 5, 2008

(87) PCT Pub. No.: WO2007/029254
PCT Pub. Date: Mar. 15, 2007

(65) Prior Publication Data
US 2009/0099618 A1    Apr. 16, 2009

Related U.S. Application Data

(60) Provisional application No. 60/714,460, filed on Sep. 6, 2005.

(51) Int. Cl.
*A61N 1/00* (2006.01)
(52) U.S. Cl. .......................................................... 607/9
(58) Field of Classification Search ................. 607/4–28
See application file for complete search history.

(56) References Cited

U.S. PATENT DOCUMENTS

| | | | |
|---|---|---|---|
| 4,387,717 A | 6/1983 | Brownlee et al. |
| 5,738,105 A | 4/1998 | Kroll |
| 5,978,707 A | 11/1999 | Krig et al. |
| 6,233,487 B1 | 5/2001 | Mika et al. |
| 6,261,280 B1 | 7/2001 | Houben et al. |
| 6,263,242 B1 | 7/2001 | Mika et al. |
| 6,292,693 B1 | 9/2001 | Darvish et al. |
| 6,370,430 B1 | 4/2002 | Mika et al. |
| 6,480,737 B1 | 11/2002 | Policker et al. |

FOREIGN PATENT DOCUMENTS

| | | |
|---|---|---|
| WO | WO 97/25098 | 7/1997 |
| WO | WO 98/10831 | 3/1998 |
| WO | WO 98/10832 | 3/1998 |

(Continued)

OTHER PUBLICATIONS

International Preliminary Report on Patentability Dated Mar. 20, 2008 From the International Bureau of WIPO Re.: Application No. PCT/IL2006/001042.

*Primary Examiner* — Scott M Getzow

(57) ABSTRACT

Devices, systems and methods for controlling (inhibiting or enabling) the delivery of electrotherapeutic signals to a heart using sensing of local and/or global ECG signals to detect ventricular arrhythmia or indication of possible ventricular arrhythmia in the heart. The devices, systems and methods process the sensed signals and are capable of delivering electrotherapeutic signals to the heart in the presence of a supra-ventricular arrhythmia such as atrial fibrillation and atrial flutter, while inhibiting the delivering electrotherapeutic signals in the presence of PVCs and/or extopic beats, and/or ventricular arrhythmia. The electrotherapeutic signals may include, among others, pacing signals and cardiac contractility modulating signals.

40 Claims, 32 Drawing Sheets

FOREIGN PATENT DOCUMENTS

| WO | WO 99/27994 | 6/1999 |
| WO | WO 00/57952 | 10/2000 |
| WO | WO 01/00137 | 1/2001 |
| WO | WO 01/13992 | 3/2001 |
| WO | WO 01/87134 | 11/2001 |

APPARATUS AND METHOD FOR DELIVERING ELECTRICAL SIGNALS TO A HEART

CROSS-REFERENCE TO RELATED US APPLICATIONS

This application is a National Phase of PCT Patent Application No. PCT/IL2006/001042 having International Filing Date of Sep. 6, 2006, which claims the benefit of US Provisional Patent Application No. 60/714,460 filed on Sep. 6, 2005, entitled "APPARATUS AND METHOD FOR DELIVERING ELECTRICAL SIGNALS TO A HEART", The contents of the above Applications are all incorporated herein by reference.

FIELD OF THE INVENTION

The present invention relates generally to the field of methods and medical devices for modulating cardiac muscle activity and contractility and for cardiac pacing and more specifically to the field of methods and devices for delivering of cardiac contractility modulating signals to the heart of patients with supra-ventricular heart rate disorders.

BACKGROUND OF THE INVENTION cardiac contractility modulating (CCM) devices are devices which modulate the activity of excitable tissues by application of non-excitatory electrical field signals to the excitable tissue through suitable electrodes in contact with the cardiac tissue. For example, CCM devices may be used, inter alia, to increase or decrease the contractility of cardiac muscle in vitro, in vivo and in situ. as disclosed in detail in PCT application PCT/IL97/00012 (International Publication Number WO 97/25098) to Ben-Haim et al., titled "ELECTRICAL MUSCLE CONTROLLER", incorporated herein by reference. Other methods and applications of CCM devices are disclosed in PCT application PCT/IL97/00231 (International Publication Number WO 98/10828) titled "APPARATUS AND METHOD FOR CONTROLLING THE CONTRACTILITY OF MUSCLES" to Ben Haim et al., incorporated herein by reference, PCT application PCT/IL97/00232 (International Publication Number WO 98/10829) titled "DRUG-DEVICE COMBINATION FOR CONTROLLING THE CONTRACTILITY OF MUSCLES" to Ben Haim et al., incorporated herein by reference and PCT application PCT/IL97/00233 (International Publication Number WO 98/10830) titled "FENCING OF CARDIAC MUSCLES" to Ben Haim et al., incorporated herein by reference, PCT application PCT/IL97/00235 (International Publications Number WO 98/10831) to Ben Haim et al., titled "CARDIAC OUTPUT CONTROLLER", incorporated herein by reference.

Further applications of the CCM including devices combining cardiac pacing and cardiac contractility modulation are disclosed in PCT Application, International Publication No. WO 98/10832, titled "CARDIAC OUTPUT ENHANCED PACEMAKER" to Ben Haim et al., co-assigned to the assignee of the present application. Such CCM devices function by applying to selected cardiac segments electrical signals of suitable amplitude and waveform, appropriately timed with respect to the heart's intrinsic electrical activity or with respect to paced cardiac electrical activity. The contraction of the selected segments can be modulated to increase or decrease the stroke volume of the heart. The timing of the CCM signals must be carefully controlled since application of the CCM signal to the myocardium at inappropriate times may be arrhythmogenic. The CCM signal must therefore be applied to the selected cardiac region within a defined time interval during which the selected cardiac region will not be stimulated by the CCM signal.

As disclosed in International Publication No. WO 98/10832, the ETC signal may be timed relative to a trigger signal which is also used as a pacing trigger, or may be timed relative to locally sensed depolarizing electrogram signals.

Timing of the delivery of CCM signals relative to the time of detection of locally sensed electrogram signals may present certain practical problems. For example, triggering of the CCM signal by any locally detected depolarizing signals irrespective of the time of detection of the depolarizing signal within the cardiac beat cycle, may increase the probability of spurious detection of noise signals or of ectopic beats such as premature ventricular contractions (PVCs) or the like, which may lead to delivery of improperly timed and potentially arrhythmogenic CCM signals. It is therefore desirable to have a method for determining proper timing of the delivery of CCM signals without unduly increasing the probability of delivering an improperly timed CCM signal caused by spurious noise detection or by detection of ectopic beats.

One approach used for to detecting suspected events such as ectopic beats is to use a combination of sensing leads, typically including an atrial lead (as well as one or more ventricular leads to detect such events. Sensing the electrical events recorded simultaneously by ventricular and atrial leads provides information based inter alias, on the signal shape, duration and timing. This multiple lead information may be processed using a variety of detection and decision algorithms) and used to differentiate between normal cardiac events (such as intrinsically naturally initiated ventricular pacing and ectopic or other abnormal forms of cardiac electrical events (such as, for example PVCs). When such a suspected abnormal cardiac event is detected, the delivery of a CCM signal within the current beat cycle (and optionally within one or more of the following beat cycles) is inhibited.

However, the use of multiple leads including an atrial lead complicates and often increases the time required for lead placement.

Typically, about 35% of cardiac patients are diagnosed with Atrial fibrillation (AF) or paroxysmal AF or are candidates to develop AF. Currently, the treatment of such patients with supra-ventricular paroxysmal cardiac disorders present a challenge for CCM therapy as current ectopic beat detection methods and algorithms do not enable differentiating between temporally abnormal electrical activity due to an ectopic beat propagating from a lateral ventricular focus and an abnormally timed beat resulting from paroxysmal atrial activity. As a result many of the patients with AF or belonging to a group with increased probability for developing AF are not candidates for CCM therapy using a CCM device. Furthermore, if a patient already having an implanted CCM device develops AF, the CCM therapy is inhibited whenever an atrium is arrythmogenic. This situation is undesirable, as the benefits of CCM therapy cannot be delivered to the ventricles while any atrial arrythmogenic activity is detected.

Another problem which may arise in the use of CCM devices is that a CCM device may often be implanted in a patient which has a previously implanted pacemaker. In such a situation the pacemaker of the patient may or may not pace the heart of the patient, independently. Such independent pacing is not synchronized with the activity of the CCBM device. In such a case, if the CCM is expected to timely and safely deliver CCM signals to the heart, the CCM device must be able to recognize the pacing of the heart by the independent pacemaker and to suitably detect the pacing and to suitably adapt the CCM delivery parameters in accordance with the pacemaker activity.

It may therefore be advantageous to be able to safely deliver ventricular CCM signals to a patient's heart in the presence of AF as well as to safely and effectively deliver CCM signals to the heart of patients having an independent implanted pacemaker.

SUMMARY OF THE INVENTION

The present application provides devices, methods and a systems capable of delivering CCM signals to one or more of the cardiac ventricles of a patient having AF or paroxysmal AF or suspected of developing a supra-ventricular arrhythmia.

One aspect of the present invention is a sensing configuration based on one or more ventricular sensing electrodes which is used together with a distant electrode (preferably, but not obligatorily, the electrically conducting can of the CCM device or CCM/pacemaker device, or CCM/Pacemaker/Defibrillator device) to provide one or more locally sensed signal (useful for obtaining sharply defined timing information of local ventricular electrical events) and an additional (one or more) ECG signal (useful as a global signal for obtaining information about electrical events which may have occurred at a ventricular location distant from the site where the locally sensed event is recorded, which may have therefore not been detected using the locally sensed signal). These local and global signals are processed to detect and distinguish between a "true" ventricular ectopic electrical event (in which case the delivery of CCM signal(s) is inhibited) and an electrical event originating from a supra-ventricular source such as atrial fibrillation (AF) or paroxysmal AF (in which case a ventricular CCM signal may be safely delivered).

In accordance with one embodiment of the present invention of the present invention, the ECG signal may be an Intra-cardiac ECG (IECG) signal (such as but not limited to a unipolar recording between the can of the CCM device and one of the ventricular electrodes disposed in the ventricle.

In accordance with another embodiment of the present invention, the ECG signal(s) may be recorded using one or more non-implanted electrodes externally applied to the subject (this embodiment may be particularly suitable for cases where the CCM device is a bedside device.

In accordance with yet another embodiment of the present invention, the ECG signal(s) may be recorded using one or more non-cardiac electrodes implanted in the subject, such as, but not limited to subcutaneously implanted electrodes (For example, this embodiment may be implemented in cases having such subcutaneously implanted electrodes useful for cardiac shock therapy in conjunction with cardiac defibrillator devices). Combinations of IECG signals and ECG signals recorded with externally applied ECG electrodes and/or with any other type of electrodes implanted outside of the heart of the patient may also be used in the present invention.

Another aspect of the present invention is that the recording of the global ECG signal enables the use of a simplified lead system in which there is no need for a sensing atrial lead. In such a simplified system, preferably (but not obligatorily) only one or two ventricular leads are used (and, preferably, the can of the implanted device), obviating the need for an atrial lead.

In accordance with another aspect of the present invention, the ECG signal (global signal) is used to differentiate between an electrical event due to an arrythmogenic atrium and an electrical event due to a distant ventricular ectopic beat. This is made possible due to an increased effective sensing range of unipolar differential recording performed between the distant electrode (preferably, but not obligatorily, the can of the CCM device) and one or more of the ventricular electrode(s), as compared to the very limited effective sensing range obtainable when recording locally sensed events (for example by using differential recording between two narrowly spaced electrode tip and ring, as is known in the art, or the like) using a ventricular electrode. This is enabled by the much larger distance between the can and the ventricular electrode(s). The probability of detecting a distant ectopic activity (such as, for example an ectopic event generated in the lateral part of a ventricular wall) is much larger using such globally recorded IECG than the probability of detecting such an event using ventricular local sensing with it's limited effective sensing range.

In accordance with one aspect of the present invention, a template matching algorithm may be performed on the recorded IECG signal(s) to detect an ectopic event based on morphological criteria of the suspected event (many different types of morphological criteria may be used in the present invention).

In accordance with another aspect of the present invention, the template and the decision criteria used for performing the decision whether an event represents a normal cardiac beat or a suspected ectopic event, may be based on a fairly early portion of the recorded IECG signal. For example, the part of the IECG signal compared to the template may be the first 40 milliseconds of the signal recorded from the beginning of the beat cycle (however, other different intervals may also be used). This may reflect the fact that typically the decision whether to deliver a CCM signal to the ventricle may have to be taken in the first 100 milliseconds or so of the beat cycle (though some other values may also be used).

In accordance with another aspect of the present invention, the template may be a dynamic template which may be based on data continuously acquired from the patient and continuously adapting to time varying changes occurring in the heart of the patient. Such variations may include, inter alia, drug induced changes in cardiac electrical properties and activity, and changes in cardiac electrical waveforms due to a change in the physiological condition of the patient. Such changes may also include but are not limited to, physical stress related changes in heart rate or changes in electrical properties of cardiac muscle cell or in the properties of other electrically excitable cardiac tissues and/or pathways, hormonally induced changes due to intrinsic adrenergic or cholinergic effects, long term changes due to electrode movements or resistivity changes caused by deposition of extraneous material on the electrodes, changes in heart rate, changes in recorded waveforms due to artificial pacing by a pacemaker, or other such effects).

In accordance with another aspect of the present invention, the CCM device (and/or the biventricular pacing device and/or the combined pacemaker/CCM device, and/or a combined Pacemaker/CCM/ICD device) of the present invention may locally sense electrical activity using one or more implanted ventricular electrode(s). The locally sensed ventricular signals may be processed and analyzed to determine a plurality of signal parameters, such as, for example the R-R interval(s). In the case were two locally sensed ventricular signals are recorded by two ventricular sensing electrodes, the R-R interval for each of the ventricular electrodes may be independently recorded and used for determining if the locally sensed event satisfies certain criteria for a normal event (non-suspected event). When two ventricular electrodes are used it is also possible to measure the difference in the time of sensing of the electrical event by the two electrodes. This determined delay may also be used for deciding if the event may be classified as a normal event or as a suspected event.

In accordance with another aspect of the present invention, the CCM device is adapted for detecting whether a beat is a paced beat. This may simply be performed in cases in which the CCM device also includes pacing circuitry, in which the pacing circuitry provides a suitable timing signal representing the initiation of a paced beat. However, in cases in which a non-synchronized pacemaker is implanted in the patient in addition to the CCM device, the CCM devices of the present invention may detect if the beat is paced by the separate pacemaker by analyzing the waveforms of the sensed signals. This detection may be performed by morphological criteria based on the typical specific morphological parameters of the pacing artifact. When a beat is detected and classified as a paced beat, the CCM device applies a different unique set of testing criteria specifically constructed for paced beats. Thus, the CCM devices of the present invention may implement multiple sets of different detection and decision criteria (including different templates, different permissible R-R intervals, different permissible signal propagation criteria, and the like) for identifiable and classifiable different types of cardiac beats. For example, there may be a unique set of detection and decision criteria for paced and non-paced beats, and for different ranges of the heart rate (for which there may be changes in signal morphologies and timing, as well as for excitation wave propagation velocity). For example, for each heart rate range of several different predefined and/or experimentally determined heart rate ranges, there may be assigned a unique set of detection and decision criteria. Furthermore, external/physiological input may also be used to define and/or select a specific set of detection and decision criteria (such as, but not limited to, information related to patient's stress such as standing, walking, running, climbing stairs, and the like), or the time of the day, which may be associated with patient's activity.

In accordance with an embodiment of the present invention, the systems and devices of the present invention may be individually adapted for a specific patient by suitably collecting cardiac event data from the patient under different patient conditions (paced and non-paced beats, beats at various different heart rate ranges, and the like). After the different sets of parameters are determined and stored, the device may suitably use a selected set of decision and testing parameters based on a classification of a beat into a specific group of conditions.

In accordance with another aspect of the present invention, the systems and devices of the present invention may automatically and dynamically adapt to the current patient situation by dynamically adjusting the beat classification to the current state of the patient. For example, typically, heart rates within the range of 60-120 beats per minute are considered within the normal range in which CCM delivery is permissible. However the device may also consider the recent patient history and may base decisions on this current patient state. Thus, if the recent patient history as recorded by the device was of R-R intervals corresponding to a heart rate in the range of 60-70 beats per minute, the system will dynamically adapt the permissible R-R interval range such that the detection of a single beat with an R-R interval corresponding to an instantaneous heart rate of 110 beats per minute may now be detected as belonging to an abnormal heart rate group, and a CCM delivery will be inhibited for that beat.

The present application also provides a device, a method and a system capable of performing biventricular cardiac pacing (BIV pacing) in the cardiac ventricles of a patient having AF or paroxysmal AF or suspected of developing a supra-ventricular arrhythmia. Such biventricular pacing may be applied with or without the delivery of CCM signal(s), as the present invention allows real-time classification or almost real-time classification (for example, within a few milliseconds) of the heart beat and detection of ventricular ectopies even in the absence of atrial sensing, or in the presence atrial fibrillation. It is noted that for the purpose of this application the term "biventricular pacing" is also used to denote (and therefore by definition includes within its scope) all various different forms of cardiac resynchronization known in the art.

There is therefore provided, in accordance with an embodiment of the present invention, a method for controlling the delivery of a CCM signal to a heart of a subject. The method includes applying one or more electrodes to one or more ventricular sites of the heart, differentially recording at least one unipolar intra-cardiac electrocardiogram signal between at least one ventricular electrode disposed at a first site of the one or more ventricular sites and a distant electrode implanted in the subject, recording at least one locally sensed electrical signal from the least one ventricular electrode, processing the intra-cardiac electrocardiogram signal and the locally sensed signal to detect a suspected ectopic electrical event within a cardiac cycle of the heart and inhibiting the delivery of the CCM signal to the heart upon detecting the suspected ectopic electrical event.

There is also provided, in accordance with an embodiment of the present invention, a method for controlling the delivery of a CCM signal to a heart of a subject within a cardiac beat cycle, the method includes:

applying electrodes to one or more ventricular sites of the heart, differentially recording a first intra-cardiac electrocardiogram signal between a first ventricular electrode disposed at a first site of the one or more ventricular sites and a distant electrode implanted in said subject, the distant electrode may be any electrode which is relatively remote from the first and second ventricular site, including but not limited to an external electrode attached to the subject, a remote electrode subcutaneously implanted in the subject, a can electrode or any other type of electrode which is relatively distant or remote from the site of implantation of the first and/or the second local ventricular electrodes)—this signal may be defined as a first global signal, differentially recording a second intra-cardiac electrocardiogram signal between a second ventricular electrode disposed at a second site of the one or more ventricular sites and a distant electrode (the distant electrode may be the same distant electrode used for obtaining the first global signal but may also be another different distant electrode—and the resulting differentially recorded signal may be defined as a second global signal), recording a locally sensed third electrical signal from the first electrode (by using a unipolar recording against a reference electrode, such as, for example the can of an implanted device, or by using a bipolar recording using an additional ventricular electrode disposed close to the first ventricular electrode), this third signal may also be defined as a first local signal, recording a locally sensed fourth electrical signal from the second electrode (by using a unipolar recording against a reference electrode, such as, for example the can of an implanted device, or by using a bipolar recording using an additional ventricular electrode disposed close to the second ventricular electrode)—this fourth signal may also be defined as a first local signal, and processing the first electrocardiogram signal (the first global signal), the second electrocardiogram signal (the second global signal), the third signal (the first local signal) and the fourth signal (the second local signal) to detect a suspected ectopic electrical event within the cardiac beat cycle and inhibiting the delivery of a CCM signal to the heart upon detecting the suspected ectopic electrical event.

There is also provided, in accordance with an embodiment of the present invention, a device for controlling the delivery of a CCM signal to a heart of a subject within a cardiac beat cycle. The device includes a cardiac contractility modulating unit configured for being coupled to one or more ventricular electrodes for delivering cardiac contractility modulating signals to the heart. The device also includes a sensing unit operatively couplable to at least one of the one or more ventricular electrodes and to a distant electrode implanted in the subject. The sensing unit is configured for sensing at least one intra-cardiac electrocardiogram signal between a ventricular electrode and a distant electrode implanted in said subject, and for sensing at least one locally sensed electrical signal from the ventricular electrode. The device also includes a processing unit operatively coupled to the cardiac contractility modulating unit and to the sensing unit for controlling the operation of at least the cardiac contractility modulating unit, for receiving from the sensing unit signals representing the intra-cardiac electrocardiogram signal and the locally sensed electrical signal, for processing the electrocardiogram signal and the locally sensed signal to detect a suspected ectopic electrical event (such as, for example, an event from a remote location in the heart) within the cardiac beat cycle and for inhibiting the delivery of a cardiac contractility modulating signal to the heart upon detecting the suspected ectopic electrical event. The device also includes a power source for providing power to the cardiac contractility modulating unit, the sensing unit and the processing unit.

Furthermore, in accordance with an embodiment of the invention, the distant electrode includes at least part of an electrically conducting can of a device implanted in the subject.

It is noted, that the devices and methods of the present invention provide the ability to sense and process signals within a single heart cycle almost immediately (or within a few milliseconds from the local sense event), enabling the identification of remote ectopic activity. It is not necessary to sense and process a whole QRS complex, allowing the making of a real-time decision within the current heart beat cycle (in other words, the devices and methods of the present invention enable real time decision making within each individual beat cycle). This is different from known ICD devices and methods, which normally take a decision whether or not to provide electrical therapy several seconds after sensing and processing multiple heart beat cycles.

It is noted that, in accordance with embodiments of the present invention, the distant electrode may also be a part of a dedicated lead implanted near the device, and/or outside the ventricular chamber and/or a lead positioned in a location that allows measuring a signal vector suitable for identifying remote ectopic activity (such as, but not limited to, the LV lateral wall or posterior wall). It may also be an implantable lead, and may be positioned sub-cutaneously, or epicardially, or transvenously, or in another chamber of the heart.

It is noted that, in accordance with embodiments of the present invention, the devices and systems described herein may use other leads in the heart with a dedicated electrode or with an electrode that simultaneously serves for other purposes. Examples may include but are not limited to, a separate pacemaker lead or ICD lead, or a coronary sinus lead which may allow (possibly in parallel to its original function) connectivity to an electrode that provides signal(s) from outside the RV or LV, and thus allows better measurement of RV and LV remote ectopic activity. Such signals may be sensed and/or recorded between electrodes positioned outside the LV or RV chamber, or between one or more of such electrodes and the device's can, or between one or more such electrodes and an electrode positioned inside the RV or LV chambers.

Furthermore, in accordance with an embodiment of the invention, the power source is selected from a power source disposed within the device and a power receiving device configured for receiving power wirelessly transmitted from an external power source disposed outside of the subject.

There is also provided, in accordance with an embodiment of the present invention, a method for controlling the delivery of a CCM signal to a heart of a subject, the method includes applying one or more ventricular electrodes to one or more ventricular sites of the subject, recording at least one electrocardiogram signal of the subject, recording at least one locally sensed electrical signal from the one or more ventricular electrode, processing the electrocardiogram signal and the at least one locally sensed signal to detect a suspected ectopic electrical event within the current cardiac cycle, and inhibiting the delivery of one or more CCM signals to the heart upon detecting the suspected ectopic electrical event.

Furthermore, in accordance with an embodiment of the invention, the electrocardiogram signal is selected from, at least one unipolar intra-cardiac electrocardiogram signal recorded between at least one ventricular electrode disposed at a first site of the one or more ventricular sites and a distant electrode implanted in the subject, and at least one electrocardiogram signal recorded using one or more non-implanted electrodes externally applied to the subject.

Furthermore, in accordance with an embodiment of the invention, the current beat cycle is a paced beat cycle and the suspected ectopic electrical event is an ectopic event other than a pacing induced ventricular electrical activity.

There is also provided, in accordance with an embodiment of the present invention, a device for controlling the delivery of electrotherapeutic signals to a heart of a subject within a cardiac beat cycle. The device includes at least one electrotherapeutic signal delivering unit configured for being coupled to one or more ventricular electrodes for delivering one or more electrotherapeutic signals to the heart. The device also includes a sensing unit operatively couplable to at least one electrodes of the one or more ventricular electrodes and to a distant electrode implanted in the subject. The sensing unit is configured for sensing at least one intra-cardiac electrocardiogram signal between a ventricular electrode and a distant electrode implanted in the subject and for sensing at least one locally sensed electrical signal from the ventricular electrode. The device also includes a processing unit operatively coupled to the at least one electrotherapeutic signal delivering unit and to the sensing unit. The processing unit is configured for controlling the operation of the electrotherapeutic signal delivering unit, for receiving from the sensing unit signals representing the intra-cardiac electrocardiogram signal and the locally sensed electrical signal, for processing the electrocardiogram signal and the locally sensed signal to detect a suspected ectopic electrical event within the cardiac beat cycle and for inhibiting the delivery of the electrotherapeutic signal to the heart upon detecting the suspected ectopic electrical event. The device also includes a power source for providing power to the at least one electrotherapeutic unit, the sensing unit and the processing unit.

Furthermore, in accordance with an embodiment of the invention, the distant electrode includes at least part of an electrically conducting can of said device implanted in said subject.

Furthermore, in accordance with an embodiment of the invention, the power source is selected from a power source disposed within the device and a power receiving device configured for receiving power wirelessly transmitted from an external power source disposed outside of the subject.

Furthermore, in accordance with an embodiment of the invention, the at least one electrotherapeutic unit is selected from a pacing unit configured for performing at least biventricular pacing of the heart, a cardiac contractility modulating unit configured for delivering non-excitatory cardiac contractility modulating signals to the heart, and combinations of the pacing unit and the cardiac contractility modulating unit.

Furthermore, in accordance with an embodiment of the invention, the device includes a telemetry unit suitably coupled to the processing unit for telemetrically communicating signals between the device and a telemetry unit external to the device.

Furthermore, in accordance with an embodiment of the invention, the processing unit is configured for recording at least one electrocardiogram signal of the subject, recording at least one locally sensed electrical signal from at least one ventricular electrode, processing the electrocardiogram signal and the at least one locally sensed signal to detect a suspected ectopic electrical event within a current cardiac cycle and inhibiting the delivery of one or more of the electrotherapeutic signals to the heart upon detecting the suspected ectopic electrical event.

Furthermore, in accordance with an embodiment of the invention, the processing unit is configured for differentially recording a first intra-cardiac electrocardiogram signal between a first ventricular electrode disposed at a first site of one or more ventricular sites and a distant electrode implanted in the subject, differentially recording a second intra-cardiac electrocardiogram signal between a second ventricular electrode disposed at a second site of said one or more ventricular sites and the distant electrode, recording a locally sensed third electrical signal from the first electrode and a locally sensed fourth electrical signal from the second electrode, processing the first electrocardiogram signal, the second electrocardiogram signal, the third signal and the fourth signal to detect a suspected ectopic electrical event within a cardiac beat cycle, and inhibiting the delivery of an electrotherapeutic signal to the heart upon detecting the suspected ectopic electrical event.

Furthermore, in accordance with an embodiment of the invention, the distant electrode comprises at least part of an electrically conducting can of the device.

There is also provided, in accordance with an embodiment of the present invention, a method for controlling the delivery of electrotherapeutic signals to a heart of a subject. The method includes applying one or more electrodes to one or more ventricular sites of the subject, recording at least one electrocardiogram signal of the subject, recording at least one locally sensed electrical signal from the at least one ventricular electrode, processing the electrocardiogram signal and the at least one locally sensed signal to detect a suspected ectopic electrical event within the current cardiac cycle and inhibiting the delivery of one or more of the electrotherapeutic signals to the heart upon detecting the suspected ectopic electrical event.

Furthermore, in accordance with an embodiment of the invention, the electrocardiogram signal is selected from, at least one unipolar intra-cardiac electrocardiogram signal recorded between at least one ventricular electrode disposed at a first site of the one or more ventricular sites and a distant electrode implanted in the subject, and at least one electrocardiogram signal recorded using one or more non-implanted electrodes externally applied to the subject.

Furthermore, in accordance with an embodiment of the invention, the current beat cycle is a paced beat cycle and the suspected ectopic electrical event is an ectopic event other than a pacing induced ventricular electrical activity.

Furthermore, in accordance with an embodiment of the invention, the electrotherapeutic signals are selected from one or more ventricular pacing signals, one or more non-excitatory cardiac contractility modulating signals, and combinations thereof.

Furthermore, in accordance with an embodiment of the invention, the at least one locally sensed electrical signal is a signal obtained by bipolar recording using a ventricular electrode and a distant electrode implanted in said subject.

Furthermore, in accordance with an embodiment of the invention, the distant electrode is an electrode implanted in the subject and substantially distant from the ventricular electrode.

Furthermore, in accordance with an embodiment of the invention, said distant electrode is an electrode subcutaneously implanted in said subject.

Furthermore, in accordance with an embodiment of the invention, the distant electrode includes at least part of an electrically conducting can of a device implanted in the subject.

Furthermore, in accordance with an embodiment of the invention, the processing includes differentiating between an electrical event related to an arrhythmogenic atrium and an electrical event related to a suspected ectopic event selected from a distant ventricular ectopic beat, a premature ventricular contraction and a ventricular arrhythmic event, and the inhibiting of the delivery of one or more of the electrotherapeutic signals to the heart is performed upon detecting the suspected ectopic electrical event and is not performed upon the detection of the electrical event related to an arrhythmogenic atrium.

Furthermore, in accordance with an embodiment of the invention, the processing includes performing a template matching between at least a portion of the at least one electrocardiogram signal and a template for detecting an ectopic event based on morphological criteria of the electrocardiogram.

Furthermore, in accordance with an embodiment of the invention, the template is selected from a fixed template and a dynamically adaptive template.

Furthermore, in accordance with an embodiment of the invention, the template is a dynamically adaptive template and the dynamically adaptive template is updated based on previously recorded electrocardiogram signals.

Furthermore, in accordance with an embodiment of the invention, the result of the template matching includes computing a value representing the degree of matching of the current sensed electrocardiogram signal to the template and using at least this value for deciding whether the delivery of the electrotherapeutic signals to the heart should be inhibited or not.

Furthermore, in accordance with an embodiment of the invention, the detecting of the suspected ectopic electrical event is performed based on at least one additional test criterion or decision rule.

Furthermore, in accordance with an embodiment of the invention, the at least one additional test criterion or decision rule is selected from an R-R interval based criterion, and a criterion based on the delay in the sensing of an electrical event by two differently positioned local sensing electrodes.

Furthermore, in accordance with an embodiment of the invention, the two differently positioned local sensing electrodes are ventricular electrodes.

Furthermore, in accordance with an embodiment of the invention, the processing includes processing at least portions of the at least one electrocardiogram signal and at least portions of the at least one locally sensed electrical signal to detect an ectopic event based on one or more test criterion or decision rule.

Furthermore, in accordance with an embodiment of the invention, said one or more test criterion or decision rule is selected from an R-R interval based criterion, and a criterion based on the delay in the sensing of an electrical event by two differently positioned local sensing electrodes.

Furthermore, in accordance with an embodiment of the invention, one or more of the test criteria or decision rules may be different for different conditions of said subject.

Furthermore, in accordance with an embodiment of the invention, the different conditions of the subject are selected from the heart rate of said subject, paced and non-paced beats, drug induced changes in cardiac electrical properties and activity, changes in cardiac electrical waveforms due to a change in the physiological condition of the subject, physical stress related changes in heart rate or in heart electrical properties of cardiac muscle cells, changes, changes in the properties of electrically excitable cardiac tissues, changes in the properties of electrically excitable cardiac pathways, hormonally induced changes due to intrinsic adrenergic or cholinergic effects, long term changes due to electrode movements or resistivity changes caused by deposition of extraneous material on sensing electrodes, and combinations thereof.

Furthermore, in accordance with an embodiment of the invention, the processing includes classifying sensed beats as belonging to a plurality of different beat classes.

Furthermore, in accordance with an embodiment of the invention, the test criteria or decision rules may be different for different beat classes.

Furthermore, in accordance with an embodiment of the invention, the different beat classes are automatically adaptive classes which are dynamically modified by continuously processing stored beat data to adapt the classes in accordance with the current state of the subject.

Furthermore, in accordance with an embodiment of the invention, in accordance with an embodiment of the invention, the method automatically varies one or more of the test criteria or the decision rules, depending on the beat class into which the current beat has been classified.

Finally, in accordance with an embodiment of the invention, the methods devices and systems of the present invention may also be implemented for the construction and operation of combined pacemaker/CCM/ICD devices which include pacing, CCM therapy and defibrillating capabilities.

BRIEF DESCRIPTION OF THE DRAWINGS

The invention is herein described, by way of example only, with reference to the accompanying drawings, in which like components are designated by like reference numerals, wherein.

DETAILED DESCRIPTION OF THE INVENTION

Notation Used Throughout

Figure 1:
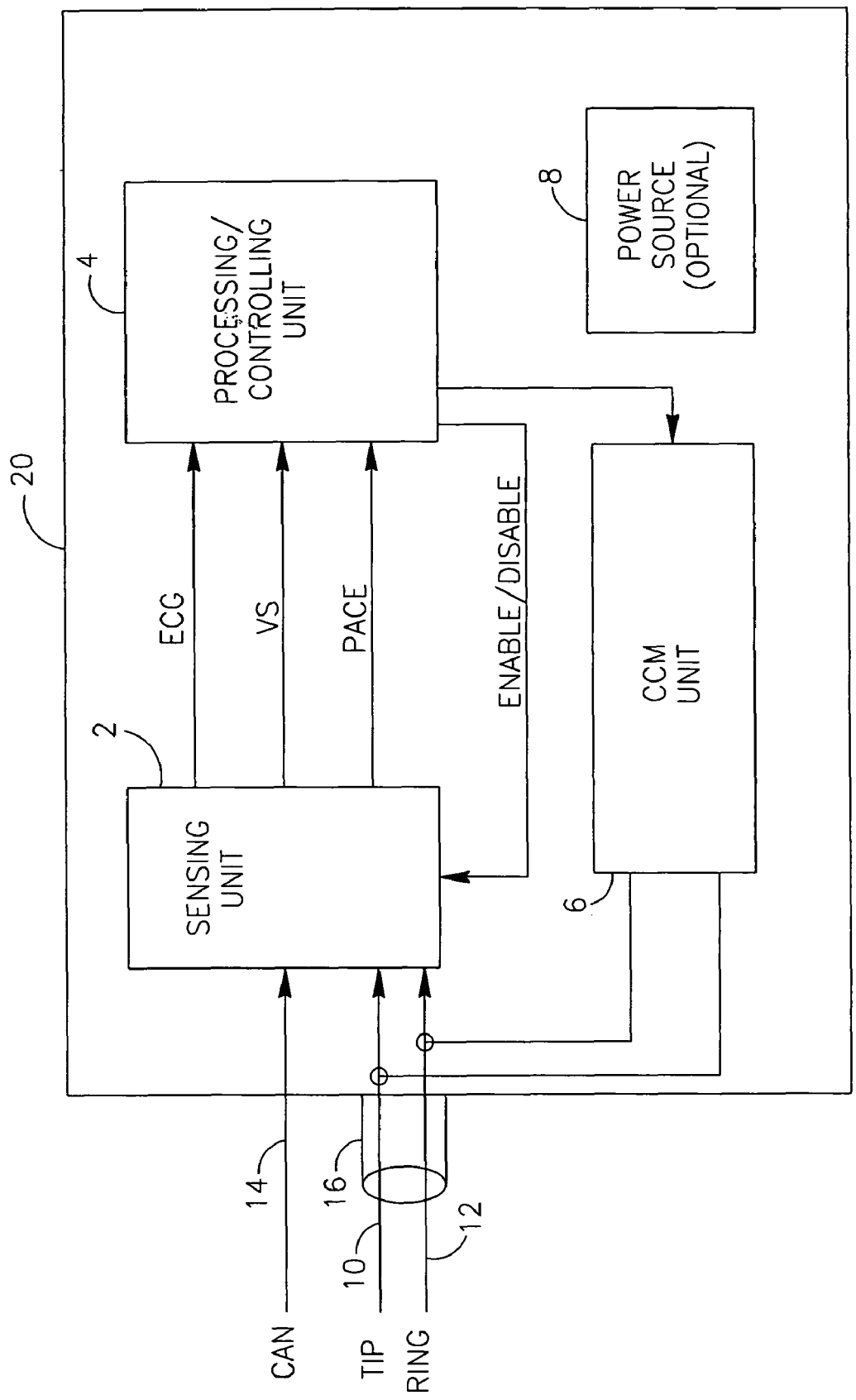
FIG. 1 is a schematic functional block diagram illustrating a CCM device, in accordance with an embodiment of the present invention.

The following notation is used throughout this document.

| Term | Definition |
| --- | --- |
| BIV | Biventricular |
| CCM | Cardiac Contractility Modulating |
| CHF | Congestive Heart Failure |
| CS | Coronary Sinus |
| GCV | Great Cardiac Vein |
| HR | Heart rate |
| IECG | Intra-cardiac Electrocardiogram |
| IEGM | Intra-cardiac Electrogram |
| LUT | Look Up Table |
| LV | Left ventricle |
| LVP | Left Ventricular Pressure |
| msec | millisecond |
| PAC | Premature Atrial Contraction |
| PE | Paced Event |
| PVC | Premature Ventricular Contraction |
| RA | Right atrium |
| RV | Right ventricle |
| SE | Sensed Event |
| SVC | Superior Vena Cava |
| VS | Ventricular Signal |

The application discloses, inter alia, devices systems and methods for delivering CCM signal(s) to a chamber of the heart undergoing electrical therapy (typically, one or more of the cardiac ventricles). The devices and methods are designed for inhibiting the delivery of the CCM signal(s) based on sensing electrical events at the cardiac chamber being therapeutically treated (regardless of electrical events in other cardiac chambers).

The devices and systems of the present invention are capable of delivering CCM signal(s) in about 70% or more (typically 80-90%) of the normal ventricular activity events, even in the presence of arrhythmia in other chambers of the same heart (for example, in the presence of supra ventricular arrhythmias such as atrial fibrillation), with negligible probability (<<1%) of CCM signal(s) delivery on a PVC.

This improved performance of CCM therapy delivery of the devices and methods disclosed in the present application is in contrast to that of currently known CCM devices which while being capable of detecting PVCs and inhibiting CCM signal delivery upon the detection of PVCs, also cause 100% inhibition of CCM signal(s) in the presence of atrial fibrillation (even if a CCM is desired at such non ventricular arrhythmia situations). Therefore, the devices and methods disclosed hereinbelow are advantageous in delivering improved therapeutic performance.

In accordance with an embodiment of the invention, the delivery of CCM signal(s) is inhibited when there is a sensed event within less than (Preferably) 150 msec from the beginning of a sensed local cardiac electrical activity.

In accordance with an embodiment of the invention, sensing may be performed in the same chamber in which the CCM signal(s) are to be delivered, without performing sensing in other cardiac chambers (e.g. in the Atria). Alternatively, if sensing is performed in other cardiac chambers, such as for example in the atria, The control of CCM signal delivery may ignore events detected by such atrial sensing. Thus, the delivery of CCM signal(s) to the chamber (ventricle) in need of therapy may be carried out even in the presence of arrhythmia (atrial fibrillation) in other cardiac chambers. The detection of atrial arrhythmia does not cause the inhibiting of delivery of CCM signal(s) but does not prevent the detection of ventricular arrhythmia with concomitant inhibition of CCM signal delivery.

In accordance with another feature of the invention, the device may also base the decision of whether or not the CCM delivery should be inhibited on cardiac events detected by using remote sensing and/or unipolar sensing.

In accordance with another feature of the invention, the device may use electrocardiogram morphology to decide whether or not to inhibit the delivery of CCM signals. The device may use a template of "correct" morphology, and may compare the sensed event to the template to decide whether the CCM should be inhibited. The device may use a set of predetermined templates (each selected to match a sensed condition) or it may adapt itself during use to changes in the heart activity.

In accordance with another feature of the invention, the device may also detect PVCs (e.g. based on global information obtained by using remote sensing and/or unipolar sensing, as is disclosed in detail hereinafter) and inhibit the delivery of CCM signal delivery when such PVCs are detected.

In accordance with another feature of the invention, the device may include a feature of automatic dynamic adaptation of the analysis of detected signals to normal or other changes in the heart's activity. This "adaptive learning" may be used initially, in order to adapt the device to the cardiac rhythm and specific characteristics of a specific recipient's heart and may also be used to adapt to changes in the same individual's heart caused by different patient conditions, such as, but not limited to, change of patients posture, activity, fitness, drug induced effects, and other physiological conditions. Based on multiple sensing events (collected and processed during many cardiac beat cycles, over extended time periods), the device may define the boundaries of "normal" activity and may determine ranges within which the sensed events are classified as: "Good", "Bad" and "Forbidden".

It is noted, that for the purposes of this application the terms "Bad" and "Atypical" are synonymously and interchangeably used throughout the specification and the drawing figures.

It is further noted, that for the purposes of this application the terms "Forbidden", "Unacceptable" and "Worse" are synonymously and interchangeably used throughout the specification and the drawing figures.

A slight deviation from the "good event" boundaries is regarded as "bad" and has less weight than an event that is within the "good" boundaries. Thus, a single or temporary deviation may have essentially no (or very little) effect on the decision to inhibit electrotherapy in future cases. However, many repeated "bad" events may shift the definition of the "good" boundaries, therefore adapting to changes such as change in activity of the patient. Events that are classified as forbidden (being too far removed from normal boundaries, such as inherently abnormal heart rate) will not be taken into account neither for delivery of electrotherapy nor for the dynamic calculation of the "good" boundaries.

The Automatic dynamic adaptation feature may be advantageous in cases where the heart changes its activity pattern frequently (such as, but not limited to, due to posture changes and/or physical activity changes). Preferably (but not obligatorily), the device may have a separate decision profile for each state (or for several states).

In accordance with another embodiment of the invention, the device may detect cardiac pacing performed in the same heart and may be capable of operating in the presence of such independent pacing by a separate pace maker (such as in the case when an independent pacemaker co-exists in the same patient in addition to a separate independent CCM device constructed and operating in accordance with the present invention).

The devices and systems of the present invention may detect different R-R intervals and/or atrial arrhythmia and/or different types of conduction block such as, but not limited to, AV block of different degrees, left bundle branch block (LBBB), left bundle branch block (RBBB), and the like.

Preferably (but not obligatorily), the devices and systems of the present invention allow the narrowing of windows of inhibition, by providing classification of multiple patient's cardiac states, and the use of parameters with narrow windows per state. This may reduce the occurrence of events in which cardiac therapy (such as, but not limited to CC signal delivery) is unduly inhibited.

In addition, the therapy may be adapted to apply various different therapy modes in response to the detection of different patient states. Thus, a different therapy may be administered to the heart and/or the currently applied therapy type may be inhibited, upon detection of such a change of state. Different therapies that may be applied or changed may include but are not limited to different CCM signal parameters (such as, but not limited to CCM signal waveform, CCM signal amplitude, CCM signal delay, CCM signal duration, and CCM signal frequency). Additionally or alternatively, the delivery of therapeutic signals may be modified by selecting between uniphasic therapeutic signal delivery, biphasic therapeutic signal delivery, unipolar therapeutic signal delivery, bipolar therapeutic signal delivery, the number and location of CCM delivery electrode/s, and the like.

In addition, the devices and systems of the present invention may provide also additional therapies and/or treatments selected from multiple non-excitatory therapies, cardioversion/defibrillation therapy, pacing therapy (anti-bradycardia), anti-tachycardia therapy (rapid pacing overdrive), resynchronization therapy (Bi-Ventricular pacing), and any other suitable cardiac electrotherapy form known in the art, by including the proper components for delivering such additional and/or complementary therapy forms to the patient and/or by adapting the electronic circuitry of the devices and systems of the present invention describe herein to also include the necessary configurations and/or programs for delivering such additional cardiac therapy modes to the patient. Devices and methods therapies for applying such additional cardiac therapy modes are well known in the art and are therefore not described herein in detail.

The different chamber states (For example, atrial fibrillating, atrial fluttering, tachycardia, bradycardia, normal beating, and the like) affect the timing of treatment such as, for example, if and when to deliver CCM therapy and/or what type of therapy to provide. Thus the present invention includes defining the chamber's state (such as by performing sensing detection and analysis and/or classification as disclosed herein) and then adjusting and/or modifying the device settings and/or parameters accordingly.

The present invention may also include automatic smooth transition from one state to the other. Intermittent changes between normal beats to atrial fibrillation or from normal beats to paced beats may be automatically identified and handled by the system, and the system selects the appropriate parameter set for the detected state and allows adaptation thereof to maintain continuity of CCM therapy delivery and/ or of other types of therapy or therapies, if used.

Reference is now made to FIG. 1 which is a schematic functional block diagram illustrating a CCM device, in accordance with an embodiment of the present invention. The CCM device 20 includes a sensing unit 2, a processing/controlling unit 4, a CCM unit 6 and a power source 8. The sensing unit 2 is connectable to suitable implantable electrodes. In the embodiment shown in FIG. 1, the sensing unit 2 may be coupled to a suitable ventricular lead 16 having a tip electrode 10, a ring electrode 12. The sensing unit 2 is also suitably connected to a can electrode 14 (the can is not shown for the sake of clarity of illustration). The electrodes and leads may be any suitable type of lead or electrode known in the art. The electrode 14 is preferably implemented as the can of the CCM device (not shown) or any electrically conducting suitable part of the can, but may also be any other type of suitable electrode implanted in the patient and relatively distant from the site of implantation of the electrodes 10 and 12.

The sensing unit 2 is used to sense a signal differentially recorded between the tip electrode 10 and the ring electrode 12. This signal is generally referred to as a locally sensed signal and is useful for obtaining relatively sharply defined timing information of locally sensed events occurring in the rather limited sensing range of the ventricular electrode tip and ring.

It is noted that while the embodiment of FIG. 1 is illustrated with a tip electrode and a ring electrode, this is not obligatory and many other types of arrangements of the ventricular electrode may be used. For example, a ventricular lead configuration having two rings electrodes disposed relatively close to each other, may also be used as is known in the art. Thus, any type of electrode configuration suitable for recording a locally sensed signal may be used with the device of the present invention.

The sensing unit 2 may also be used for sensing a global signal by performing a unipolar recording of the potential difference between the tip electrode 10 and the can electrode 14 (or, alternatively, between the ring electrode 12 and the can electrode 14). This sensed signal is referred to as the unipolar Intra-cardiac ECG (IECG) signal hereinafter. The signal is useful for obtaining information on electrical events occurring in a much larger sensing region positioned between the ventricular electrode used and the can electrode. The IECG global signal may thus contain useful information about events which occur at a much larger distance from the ventricular electrode tip or ring being used and is used in the present invention to detect, inter alia, distant ectopic activity (such as, for example an ectopic event generated in the lateral part of a ventricular wall).

The sensing unit 2 is suitably connected to the processing/controlling unit 4. The sensing unit 2 may output the sensed ECG (labeled ECG in FIG. 1) signal and the locally sensed ventricular signal (labeled VS in FIG. 1) and may also provide the processing/controlling unit 4 with signals representing the occurrence of a pacing event (labeled: PACE, in FIG. 1). Such signals may be obtained from several possible sources (not shown) including analog signal detecting unit(s) (not shown) included in the device 20 and operative to detect pacing artifacts, or from digital processing and monitoring of the signals recorded in one or more of the electrodes coupled to the sensing unit 2 or, alternatively, from a pacing unit (not shown) that may optionally be included in the CCM device 20. This pacing indicating signal indicates that pacing has occurred, irrespective of the way that the information was obtained.

The sensing unit 2 may also include further circuitry for filtering or conditioning the input signals and may also include switching and/or isolating and/or over voltage protecting circuitry as is known in the art.

In cases where the CCM signals are delivered through the same electrodes that perform the sensing, the processing/controlling unit 4 may output a suitable enable/disable signal or switching signal to the sensing unit 2 for isolating the sensing circuitry from the voltages applied by the CCM unit 6. The processing/controlling unit 4 is suitably connected to the CCM unit 6 and provides suitable control signals to the CCM unit 6 for controlling the delivering of CCM signals to the electrodes 10 and 12 of the ventricular lead 16.

The processing/controlling unit 4 receives the locally sensed ventricular signal (VS) and the global IECG signal (ECG) and may digitize and store the signals (in a suitable memory device (not shown) for further processing as is disclosed in detail hereinafter. The power source 8 may be any suitable electrical power source known in the art and may (optionally) be housed inside the can of the CCM device 20. Alternatively, the power source 8 may be an external power source such as a DC current supply or a mains power supply or any other suitable power source known in the art and disposed out of the CCM device (An external power source may be used, for example, in the case of a bedside non-implanted CCM device, connectable to electrodes implanted in the patient).

Figure 2:
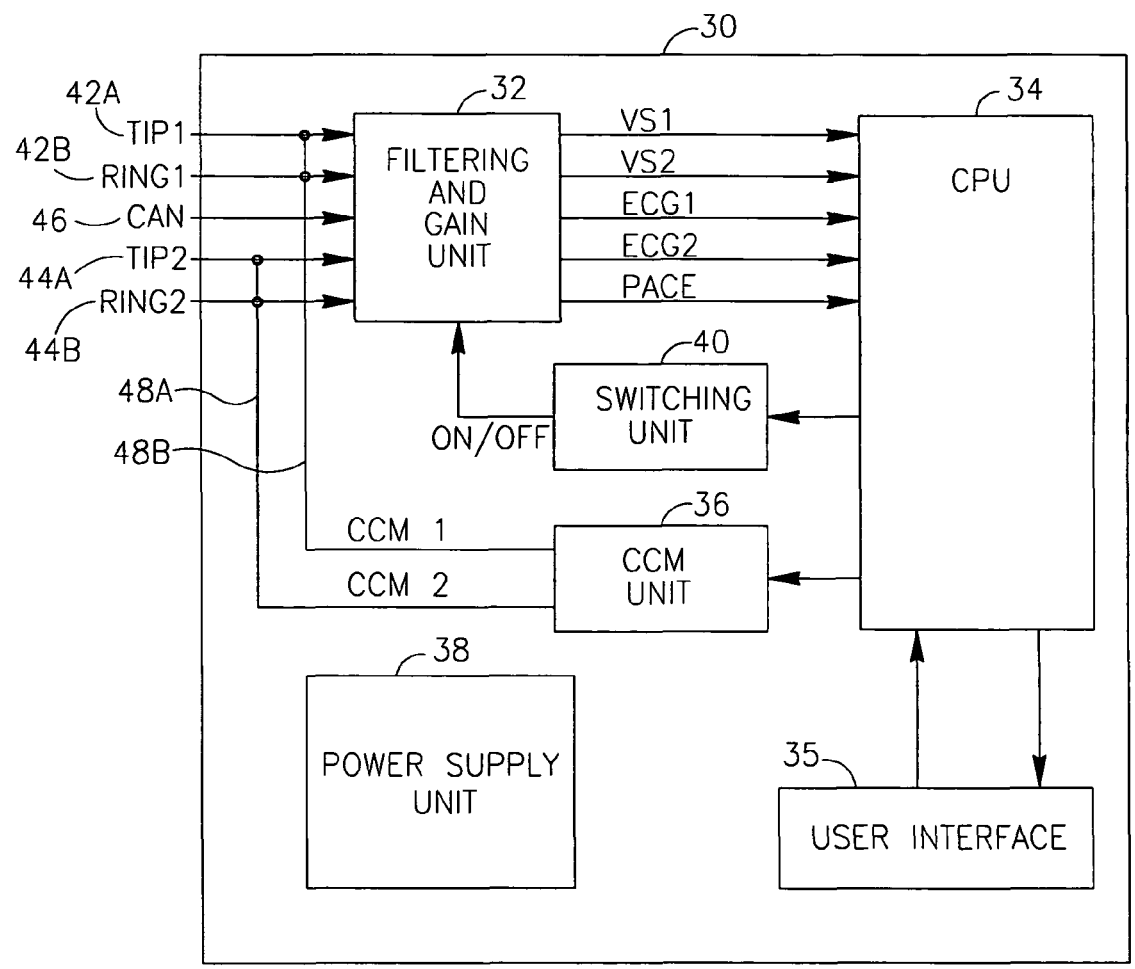
FIG. 2 is a schematic functional block diagram illustrating a CCM device adapted for using two pairs of ventricular sensing electrodes for sensing cardiac events and for controlling the delivering of CCM signals to the ventricle(s) based on information obtained from the two pairs of ventricular sensing electrodes and a can electrode, in accordance with an embodiment of the present invention.

Reference is now made to FIG. 2 which is a schematic functional block diagram illustrating a CCM device adapted for using two pairs of ventricular sensing electrodes for sensing cardiac events and for controlling the delivering of CCM signals to the ventricle(s) based on information obtained from the two pairs of ventricular sensing electrodes and a can electrode, in accordance with an embodiment of the present invention.

The device 30 includes a filtering and gain unit 32, a central processing unit (CPU) 34, a CCM unit 36, a switching unit 40, a user interface 35 and a power supply unit 38. The filtering and gain unit 32 may be suitably coupled to the tip electrode 42A and the ring electrode 42B of a first ventricular electrode pair (not shown in detail in FIG. 2) and to the tip electrode 44A and the ring electrode 44B of a second ventricular electrode pair (not shown in detail in FIG. 2). The filtering and gain unit 32 may also be suitably coupled to the can electrode 46 which may, preferably be the electrically conducting can of the CCM device 30, but may also be any other type of suitable electrode relatively distant from the ventricular electrodes implanted in the heart of the patient.

The CCM unit 36 is connected by suitable electrical conductor pairs 48A and 48B (schematically shown in FIG. 2), to the electrodes 44A and 44B and 42A and 42B, respectively of the ventricular electrodes to enable the delivery of CCM signals to one or more ventricular sites through one or both of the ventricular electrodes. The switching unit 40 is suitably connected to the CPU 34 and to the filtering and gain unit 32. The CPU 34 may provide enabling control signals to the switching unit 40. The switching unit 40 may switch the filtering and gain unit 32 on or off depending on the signal received from the CPU 34. The CPU 34 thus controls the ON/OFF state of the filtering and gain unit 32 to protect the circuitry of the unit 32 during the application of high voltage to the ventricular electrodes by the CCM unit 36.

The power supply unit 38 may be implemented as disclosed in detail hereinabove for the power source 8 of FIG. 1 (as an internal or external power source).

The filtering and gain unit 32 is suitably coupled to the CPU 34 and provides the CPU 34 with conditioned (filtered and/or otherwise suitably modified output signals and/or conditioned and amplified signals representative of the locally sensed signal of the first ventricular electrode pair (VS1), the locally sensed signal of the second ventricular electrode pair (VS2), a first unipolar recorded IECG signal recorded differentially between a first ventricular electrode (either 42A or 42B) and the can electrode 46 (ECG1), and a second unipolar recorded IECG signal recorded differentially between a second ventricular electrode (either 44A or 44B) and the can electrode 46 (ECG2). A pace signal representing the occurrence of pacing is also provided by the filtering and gain unit 32 to the CPU 34 (as explained in detail with respect to the PACE signal of the sensing unit 2 of FIG. 1).

The CPU 34 may digitize (the digitizing unit is not shown, for the sake of clarity of illustration) all the signals provided by the filtering and gain unit 32 and may store, record and process these signals to perform various detection, testing classification and decision operations performed by suitable programs operating on the CPU 34 (or embedded or stored therein). The details of such detection, testing classification and decision operations and algorithms are disclosed hereinafter. Based on the decisions computationally made by the CPU 34, the CPU 34 may control the switching unit 40 and the CCM unit 36 by suitable control signals to deliver CCM signals to the heart.

The user interface 35 may be any type of user interface device or devices which may allow input of instructions and data by the user into the device 30 and/or output of data, reports, graphs and numerical or alphanumeric data and/or symbols to the user of the device. The user interface 35 may include, but is not limited to, any number of various types of display devices as well as any input device, keyboard, mouse, or pointing device or combinations of such devices, as is known in the art. Thus, the user may receive data from the device 30 and may also be used to interact with and/or to program and/or to control the device 30, as is know in the art.

Figure 3:
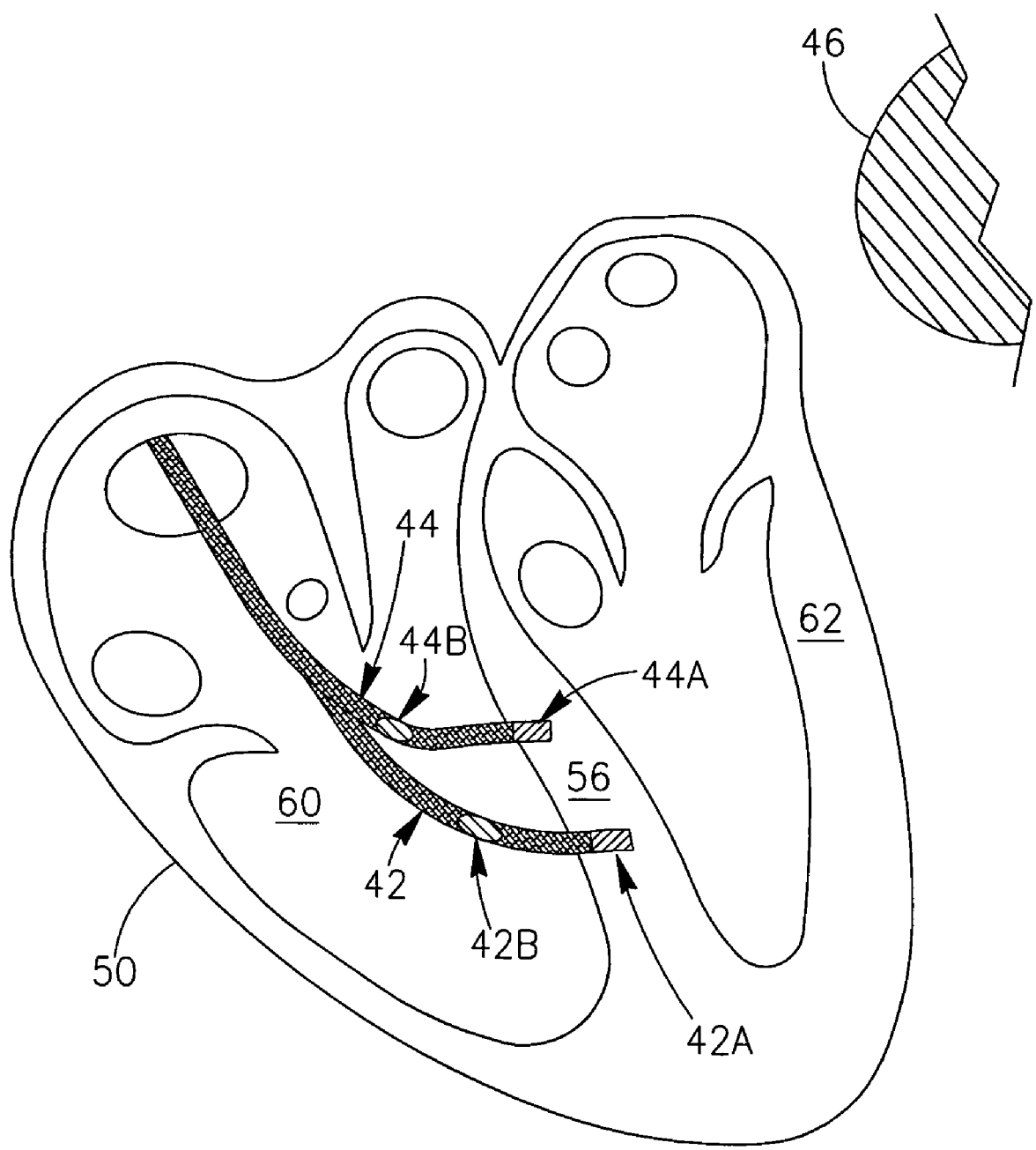
FIG. 3 is a schematic part cross-sectional diagram, illustrating a typical arrangement of two ventricular electrodes placed in the septum region of the ventricles of a heart for sensing signals of cardiac events and for delivering CCM signals to one or more of the cardiac ventricles.

Reference is now made to FIG. 3 which is a schematic part cross-sectional diagram, illustrating a typical (non-limiting) arrangement of two ventricular electrodes placed in the septum region of the ventricles of a heart for sensing signals of cardiac events and for delivering CCM signals to one or more of the cardiac ventricles.

The ventricular lead 42 is shown attached to the septum 56 of the heart 50. The electrode 42 has a tip electrode 42A embedded in the septum 56 and a ring electrode 42B disposed in the right ventricular chamber 60. Another ventricular lead 44 is shown attached to the septum 56 and has a tip electrode 44A embedded in a different site of the septum 56 and a ring electrode 44B disposed in the right ventricular chamber 60. Part of the can electrode 46 of the CCM device 30 (of FIG. 2) is also shown located outside the heart. However, other, distant electrodes implanted at a site distant from the heart 50 (such as, but not limited to subcutaneously implanted ECG electrodes) may be used instead of the can 46 for recording an ECG signal. Additionally or alternatively, one or more non-implanted external electrodes (not shown in FIG. 3) may be placed on the patient's skin and used to record a global ECG signal independently from the ventricular electrodes 42 and 44, as is known in the art. Such recorded ECG signals may be used by the methods and devices of the present invention together with one or more locally sensed ventricular signal(s), for controlling the delivery of the CCM signals to the heart 50.

It is noted that this electrode arrangement is shown by way of example only and is not intended to limit the range of possible alternative electrode placement arrangements and configurations. Thus, it is possible to use a single ventricular electrode (and the can electrode) for the purposes of the present invention. Alternatively, any practically achievable number and arrangement of ventricular electrodes and can electrode(s) (or other distant electrode or electrodes) may also be used in the devices and methods of the present invention and are intended to be within the scope and spirit of the invention. It is further noted that the type, construction, geometry, configuration shape and dimensions of the electrodes and leads used for the present invention may be varied depending on the specific application and other design, electrical and practical considerations, as is known in the art of implantable electrodes.

Figure 4:
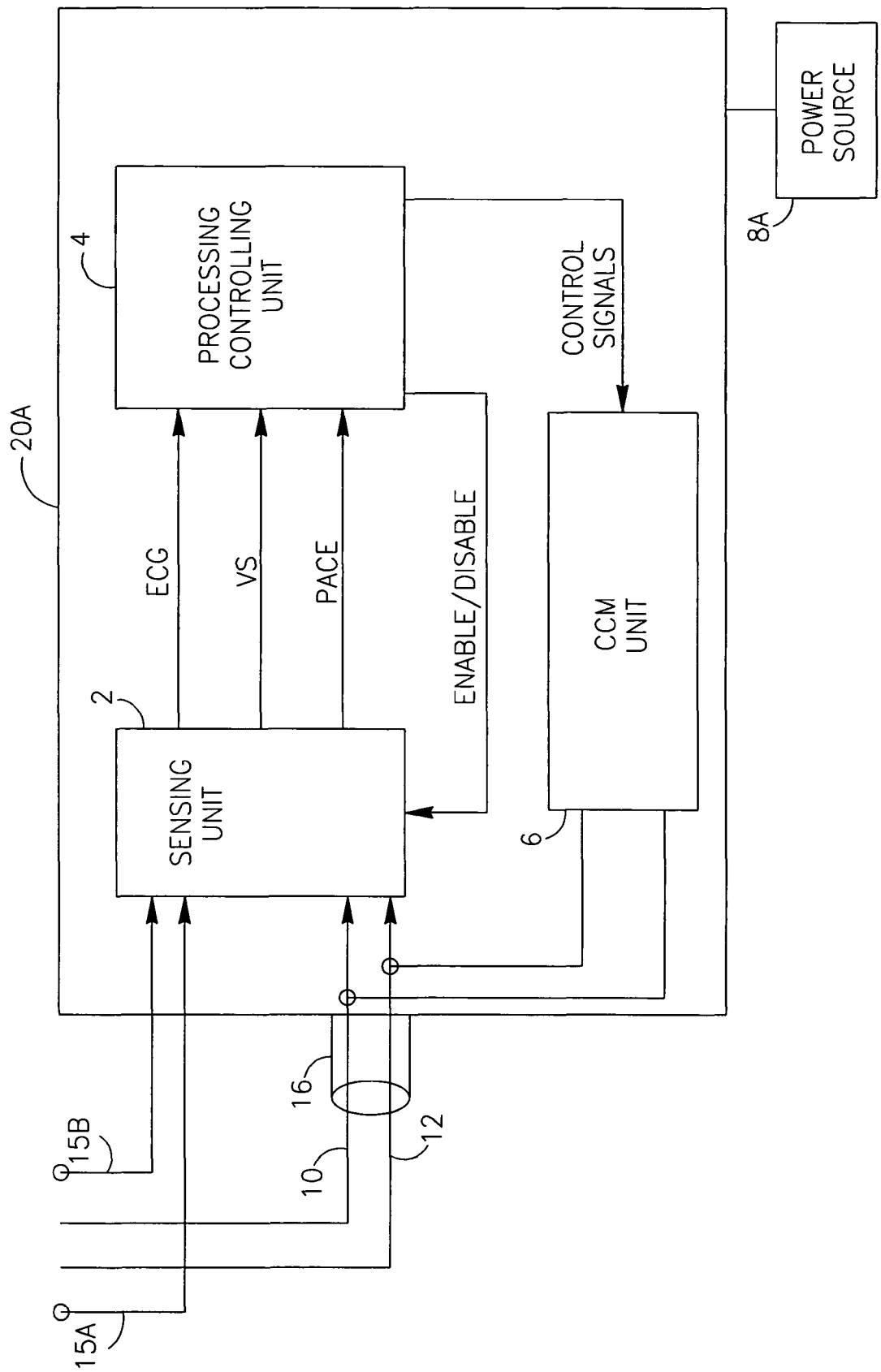
FIG. 4 is a schematic functional block diagram illustrating a CCM device adapted for use with a pair of intra-ventricular electrodes and with two or more ECG electrodes, in accordance with an embodiment of the present invention.

Reference is now made to FIG. 4 which is a schematic functional block diagram illustrating a CCM device adapted for use with a pair of intra-ventricular electrodes and with two or more ECG electrodes, in accordance with an embodiment of the present invention.

The device 20A is similar in construction and operation to the device 20 of FIG. 1, except that the power source 8A is an external power source disposed outside the can of the CCM device 20A and that the sensing unit 2 is coupled to a pair of ECG electrodes 15A and 15B instead of being coupled to the can electrode 14 of FIG. 1. The ECG electrodes may be any suitable ECG electrodes applied to the patient. For example, in a bedside implementation of the CCM device 20A, the ECG electrodes 15A and 15B may be standard patch electrodes externally electrically coupled to the skin of the patient as is known in the art. Any other type of external ECG electrodes may be used as the external ECG electrodes.

Alternatively, the electrodes 15A and 15B may be any suitable type of ECG electrodes implanted in the patient at a body location outside the heart of the patient. For example, the ECG electrodes 15A and 15B may be subcutaneously implanted electrodes (such as, but not limited to the subcutaneous electrodes used for delivering shock therapy to patients). However other types of electrodes implanted in locations outside of the heart may also be used in the present invention.

Figure 5:
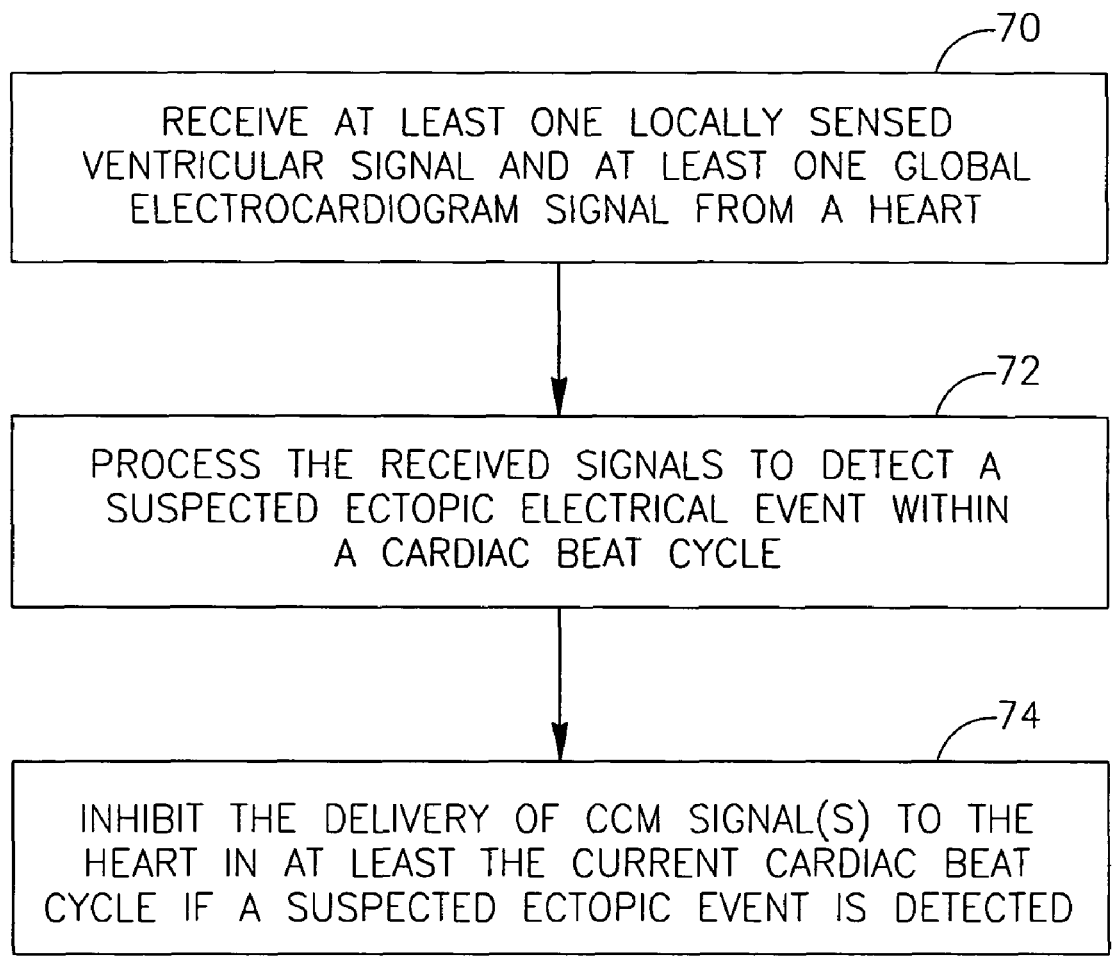
FIG. 5 is a schematic flow diagram representing steps of a general method for operating the CCM devices and systems of FIGS. 1-2 and 4, in accordance with an embodiment of the present invention.

Reference is now made to FIG. 5 which is a schematic flow diagram representing steps of a general method for operating the CCM devices and systems of FIGS. 1-2 and 4, in accordance with an embodiment of the present invention.

In accordance with an embodiment of the present invention, the method of CCM delivery control is based on receiving at least one locally sensed ventricular signal and at least one intra-cardiac electrocardiogram (IECG) signal recorded in a heart (step 70). The program implementing the method, processes the received signals to detect a suspected ectopic electrical event within a cardiac beat cycle (step 72). Typically (but not obligatorily), a detected ectopic event may be due to an electrical event occurring in a ventricular site distant from the site of recording of the locally sensed ventricular signal. For example, when the locally sensed signal is recorded at a septal region as illustrated in FIG. 3, an electrical event detected in the global IECG signal may represent an ectopic beat generated in the lateral ventricular wall of the LV—for example, at a site 62 fairly distant from the local sensing site at the septum 56.

It is noted that other types of distant cardiac ectopic events occurring in other parts of the ventricles of the hear may also elude detection by local sensing ventricular electrodes but may be picked up and detected successfully by the type of global recording (ECG type recording) described herein due to its extended sensing range of such ECG recording electrode arrangements Such an ectopic beat may be out of the limited sensing range of the septal local sense ventricular electrodes (which is typically limited to a few millimeters from the recording site) but may be clearly detected in the IECG unipolar recorded between the can electrode 14 (of FIG. 1) and one of the ventricular electrodes 10 (tip electrode) or 12 (ring electrode) of FIG. 1. Similarly, with reference to FIGS. 2 and 3, such a distant ectopic beat may be detected by the IECG unipolar recorded between the can electrode 46 (of FIG. 2) and one of the ventricular electrodes 42A, or 42B, and 44A or 44B of the ventricular leads 42 and 44, respectively, of FIGS. 2 and 3.

After the locally sensed signal(s) and the global signal(s) have been processed and analyzed for the presence of a suspected ectopic event (as will be disclosed in details hereinafter with respect to different embodiments of the invention), the program may, if a suspected ectopic event has been detected, inhibit the delivery of a CCM signal to the heart in at least the current cardiac beat cycle (step 74). It is noted that while the program implementing the method may be designed to inhibit the delivery of CCM signal only within the current beat cycle, it may also be set, in accordance with an additional embodiment of the present invention, to inhibit CCM signal delivery in more than one beat cycle occurring after the beat cycle in which the ectopic events was detected.

Figure 6:
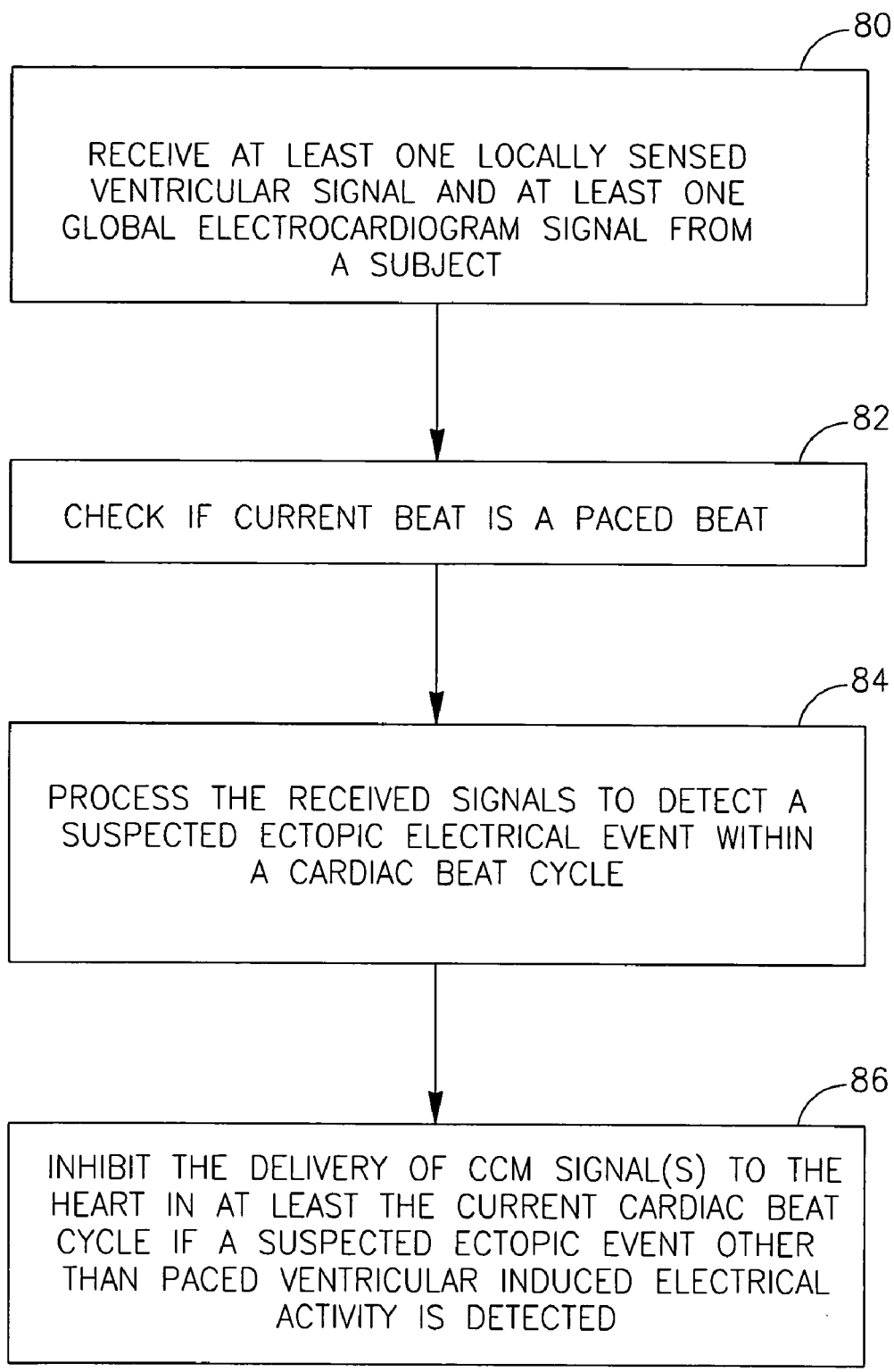
FIG. 6 is a schematic flow diagram representing steps of a general method for operating the CCM devices and systems of FIGS. 1-2 and 4, in the presence of pacing of the heart, in accordance with an embodiment of the present invention.

Reference is now made to FIG. 6 which is a schematic flow diagram representing steps of a general method for operating the CCM devices and systems of FIGS. 1-2 and 4, in the presence of pacing of the heart, in accordance with an embodiment of the present invention.

In accordance with an embodiment of the present invention, the method of CCM delivery control is based on receiving at least one locally sensed ventricular signal and at least one global electrocardiogram (ECG) signal recorded from a subject (step 80). The program implementing the method checks (within each beat cycle) if the current beat is a paced beat (step 82). The program processes the received signals to detect a suspected ectopic electrical event within a cardiac beat cycle (step 84).

After the locally sensed signal(s) and the global signal(s) have been processed and analyzed for the presence of a suspected ectopic event (as will be disclosed in detail hereinafter with respect to different embodiments of the invention), the program may, if a suspected ectopic event other than paced ventricular induced electrical activity has been detected, inhibit the delivery of a CCM signal to the heart in at least the current cardiac beat cycle (step 86). For example, the sensing unit 2 of the device 20 (FIG. 1) may, upon detecting the electrical artifact associated with pacing of the heart, provide the processing/controlling unit 4 with a suitable PACE signal (or flag) indicative of the detected pacing (or of pacing scheduled by an internal pacemaker circuitry included in the device 20). The PACE signal or flag may be used by the processing/controlling unit 4 to avoid the detection of the pacing artifact signal as a suspected ectopic beat. This may effectively prevent unnecessary inhibition of the delivery of CCM signals to the heart in paced beats.

It is noted that while the program implementing the method may be designed to inhibit the delivery of the CCM signal only within the current beat cycle, it may also be set, in accordance with an additional embodiment of the present invention, to inhibit CCM signal delivery in more than one beat cycle occurring after the beat cycle in which the suspected ectopic event was detected.

Figure 7:
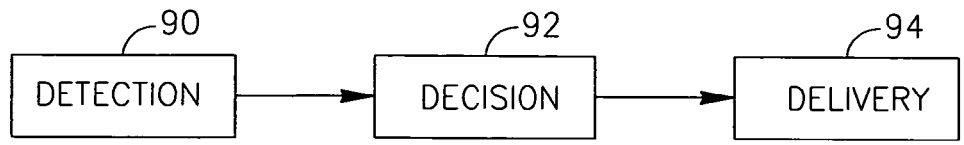
FIG. 7 is a general functional block diagram schematically illustrating the general organization of an embodiment of the CCM delivery controlling method of the present invention.

Reference is now made to FIG. 7 which is a general functional block diagram schematically illustrating the general organization of the CCM delivery controlling method of the present invention.

In general, the method includes three main blocks of operations, the detection block 90 includes steps and operations associated with conditioning and/r filtering the input signal received from the electrodes and processing of the input signals to detect significant electrical events occurring in the heart and satisfying selected criteria including pacing artifacts, paced events, and sensed events and for determining the desired timing for delivery of CCM within the current beat from the detected electrical events.

The decision block 92 analyzes the current beat based on some of the information processed in the detection block 90, determines if the beat is paced or sensed and analyzes the locally sensed signals to determine if they pass certain tests including R-R test—testing the time from the previous locally sensed event (as disclosed in detail hereinafter), V12 test (applied only in cases of two (or more) local sense ventricular electrodes)—testing the delay of sensing the event in two different local sense electrodes. The decision block 92 also analyzes the global ECG signal(s) to detect abnormal activity just before the scheduled time of delivery of the CCM signal by using various detection strategies (including but not limited to morphological tests which vary for different beat types). The decision block 92 may also update all adaptive parameters in use.

The delivery block 94 delivers one or more CCM signal(s) to the heart after checking if CCM delivery is enabled and if no abnormality was detected in the event signals of the current beat or of a selectable number of preceding beats.

A general description of possible steps in each of the blocks 90, 92 and 94 is given below (it is noted that the use of the word step in the following description does not mean that the steps are consecutive and/or that the steps are performed in the order listed below. Some of the steps listed below may be performed in parallel or in partially overlapping time periods. Thus, a higher step number does not necessarily mean that the step with a lower step number is performed before a step with a higher step number):

Detection Steps:
1. Decision on paced ventricular beat (this step may be done in parallel to step 2 below):
   option a: receive a notification from a pacemaker.
   option b: analyze the sensed signals (typically this is done by hardware, such as, but not limited to, suitable analog circuitry) in the frequency range of 300-3000 Hz and detect envelope level to detect pace artifact.
   option c: analyze the local sense/ECG sense signals as received (in the frequency range <500 Hz) by the program software algorithm and detect a fast spike as indicator to pace artifact (this is typically done by a combination of a highpass filter and two threshold system, but other methods may also be used).
2. Local sensing of electrical activity (this step may be done in parallel to step 1 above):
   filtering the signal and applying thresholds.
   In this step it may be possible to use adaptive threshold(s) over time, based on recent history of detected signals.
   In this step it may be possible to use more than one set of thresholds, depending on whether the beat is classified as paced or not paced (more specifically, it may be possible to use two different sets of thresholds, one set for paced beats and one set for sensed beats).
3. Handle the cases of mixed pace and sense events ("=simultaneous").
   If a pace event and a sense event (in one or more channels/electrodes) have occurred within a short time period from each other ("simultaneous" time, usually in the range of 0-15 ms), then determine if the sense event is actually a false detection of the pace artifact, or a true sense. Likewise, if multiple simultaneous events occurred, allow the user to define the condition as noise (user is defined as the user of the device having a User interface, such as for example, a person or cardiologist who is adjusting or setting the parameters of detection algorithms of the device).
4. Determine the desired timing for CCM delivery:
   wait a desired delay time period CCM_DELAY from the last local sense event in a given beat. If there is only one ventricular electrode, then simply wait for a CCM_DELAY time period after the sense event.
   if multiple (k) electrodes are used, the program starts the CCM_DELAY period only after k events were sensed by all k electrodes within a defined short time period (e.g. 100 ms), such as not to mix events from this beat and a past beat.
Decision Steps:
5. Analysis of the current beat (done once step 4 above is completed, just at the time CCM should start):
   a. determine if beat is paced (if step 1 detected artifact within some time, such as, but not limited to, 0-100 ms before the local sense).
For a LOCAL SIGNAL:
   b. Determine if time of local sense is reasonable (time from past local sense, relative to fixed limits, and/or relative to statistics of recent heart beats). This is defined as "RR test".
   c. If more than one electrode is used, determine if time of local sense is reasonable relative to the sense time of the other electrodes in the current heart beat (relative to fixed limits, and/or relative to statistics of recent heart beats). This is defined as "V12 test". It is noted that there may be more than one parameter set used for the RR and V12 tests, responsive to whether the beat is classified as a paced beat or not.
For a GLOBAL SIGNAL:
   d. Analyze global electrogram(s) (ECG signal(s)) to detect abnormal activity just before the CCM delivery time.
   The definition of normality/abnormality is as follows:
      option I: compare the morphology of a selected early part of the global ECG signal with past beats by using a comparison to a template and check differences/relative differences
      option II: compare the relative energy of the current ECG signal prior to the CCM with the overall energy of a normal ECG. In this step there may be more than one parameter set, responsive to whether the beat is classified as a paced beat or not.

Furthermore, there may be more than one parameter set, responsive to the heart rate (RR interval) (different heart rate ranges may be assigned different template parameters).

e. Update all adaptive parameters depending on:

The program checks if the beat meet all criteria. If the beat m does meet all criteria, it is assigned "good alpha" status, and the updating step performs normal adaptation of the template(s).

If the beat meets all fixed time limits but does not meet the adaptive time limits, the program assigns the beat "bad alpha" status, and the updating step performs very slow adaptation of the template(s).

If the beat exceeds the fixed time limits (such as in the case of a too long or a too short RR interval) the program assigns the beat "worst" status, and the updating step does not perform adaptation of the template(s). (meaning that the update step does not use the current ECG signal for computing the adapted template for use in the next beat).

Delivery:

6. CCM delivery step:

a. The program checks if CCM delivery is enabled, and b. If no abnormality was detected in the current beat or in the previous N beats (for this purpose N=0, 1, 2, 3, 4, 5 . . . , may be any suitable number of beats)

c. The program then delivers the CCM signal(s) to the heart.

It is noted that all the handling of pacing is only done if it is known that the patient has an active ventricular pacemaker. Otherwise, these steps in the algorithm concerning paced beats are not used.

To summarize some of the main features of the above algorithm:

1) The decision is performed within a heart beat.

2) A combination of local detection (used to determine timing) and global detection (for sensing and detecting of remote cardiac muscle activity) is used.

3) No atrial lead sensing is needed or performed (in other words there is no atrial lead).

4) The algorithm can adapt to the presence of paced beats (by using suitable detection of pace artifacts and by using different sets of parameters for detection in paced and in non-paced beats (beat classification algorithms).

5) The algorithms allows adaptation to various patient conditions (whether by parameter adaptation or by using multiple sets of parameters (paced/normal beat, HR dependent, and the like).

Figure 8:
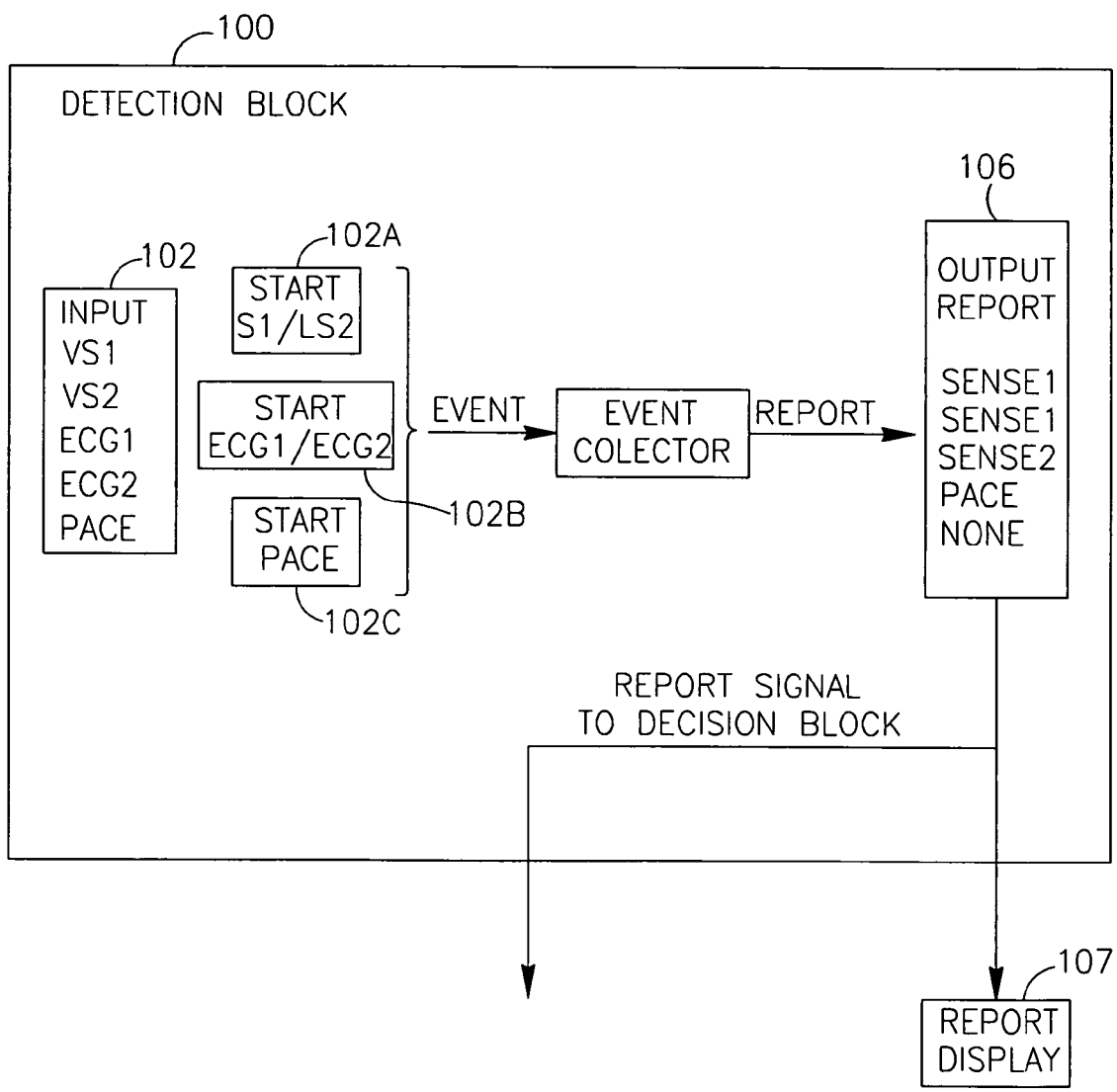
FIG. 8 is as schematic block diagram illustrating the decision block of a method of controlling the delivery of CCM signals adapted for using two locally sensed ventricular signals and two global ECG signals, in accordance with an embodiment of the present invention.

Reference is now made to FIG. 8 which is as schematic block diagram illustrating the detection block of a method of controlling the delivery of CCM signals adapted for using two locally sensed ventricular signals and two global ECG signals, in accordance with an embodiment of the present invention.

The detection block uses five input signals 102 received from five channels. The input signals include locally sensed ventricular signals VS1 and VS2 received from two independent ventricular local sense electrodes (such as for example the ventricular lead 42 and 44 of FIGS. 2 and 3). The input signals also include two globally sensed EGC signals ECG1 and ECG2 each unipolar recorded against a distant electrode as explained in detail hereinabove (such as, for example, the can electrode 44 of FIG. 2). The input signals also include a PACE signal which includes information about whether the current beat is paced or not paced, as disclosed in detail hereinabove (for example, the PACE signal may be provided by the filtering and gain unit 32 of FIG. 3.

The input signals VS1 and VS2, ECG1 and ECG2 and PACE are processed by the corresponding event detecting blocs 102A, 102B and 102C, respectively, of the event detecting block 100 (as is disclosed in detail with respect to the flow charts of FIGS. 10-13, hereinafter).

An event collector block 104 included in the detection block 100 performs the collection and recording of various channel data as is disclosed in detail hereinafter with respect to the flow chart of FIG. 13. The data collected by the event collector block 104 may be output to the decision block 110 (see FIG. 9 below) for further processing. The detection block 100 also include a report generating block 106 which may output appropriate reporting signals for use by the decision block 110 (in the form of flags or other logical signals or any other suitable signals) and additional other suitable signals (which may include graphic and/o alphanumeric information) for reporting to the user of the device. The report data may, for example, be sent to the user interface unit 35 of FIG. 2 to be presented on a suitable display device (not shown) included in the user interface 35.

Figure 9:
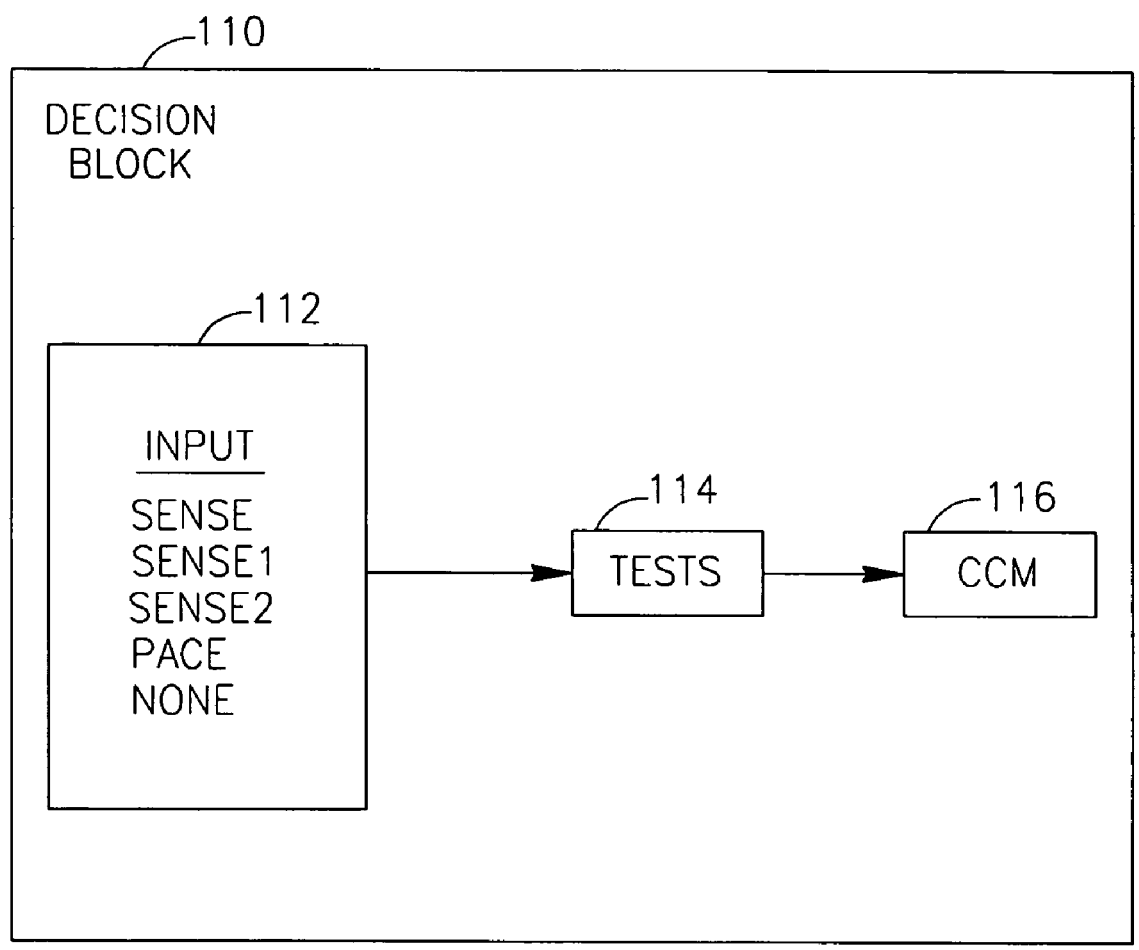
FIG. 9 is as schematic block diagram illustrating the decision block of a method of controlling the delivery of CCM signals adapted for using two locally sensed ventricular signals and two global ECG signals, in accordance with an embodiment of the present invention.

Reference is now made to FIG. 9 which is as schematic block diagram illustrating the decision block of a method of controlling the delivery of CCM signals adapted for using two locally sensed ventricular signals and two global ECG signals, in accordance with an embodiment of the present invention.

The decision block 110 includes an input signal block 112 which receives from the detection block as input a marker signal selected from the following marker signals: SENSE, SENSE1, SENSE2, PACE and NONE. These reported marker signals are generated as output of the output report block 106 of the detection block 100 (FIG. 8). The tests block 114 of the decision block 110 performs various tests (as disclosed in more detail hereinafter) on the data received from the detection block 100 and on other digitized signal data received from the recorded channels (VS1, VS2, ECG1 and ECG2) based on the recorded channels data and on the type of the currently received report marker signal (which can be a single marker signal selected from the possible marker signals SENSE, SENSE1, SENSE2, PACE and NONE.

The decision block also includes a CCM block 116 for handling the controlling of the delivery of one or more CCM signal(s) to the heart, based on the output of the tests block 114. A specific (non-limiting) implementation of the steps performed by the decision block 110 is disclosed in detail with respect to the flow charts of FIGS. 14A, 14B, 15A and 15B, hereinafter).

Figure 10:
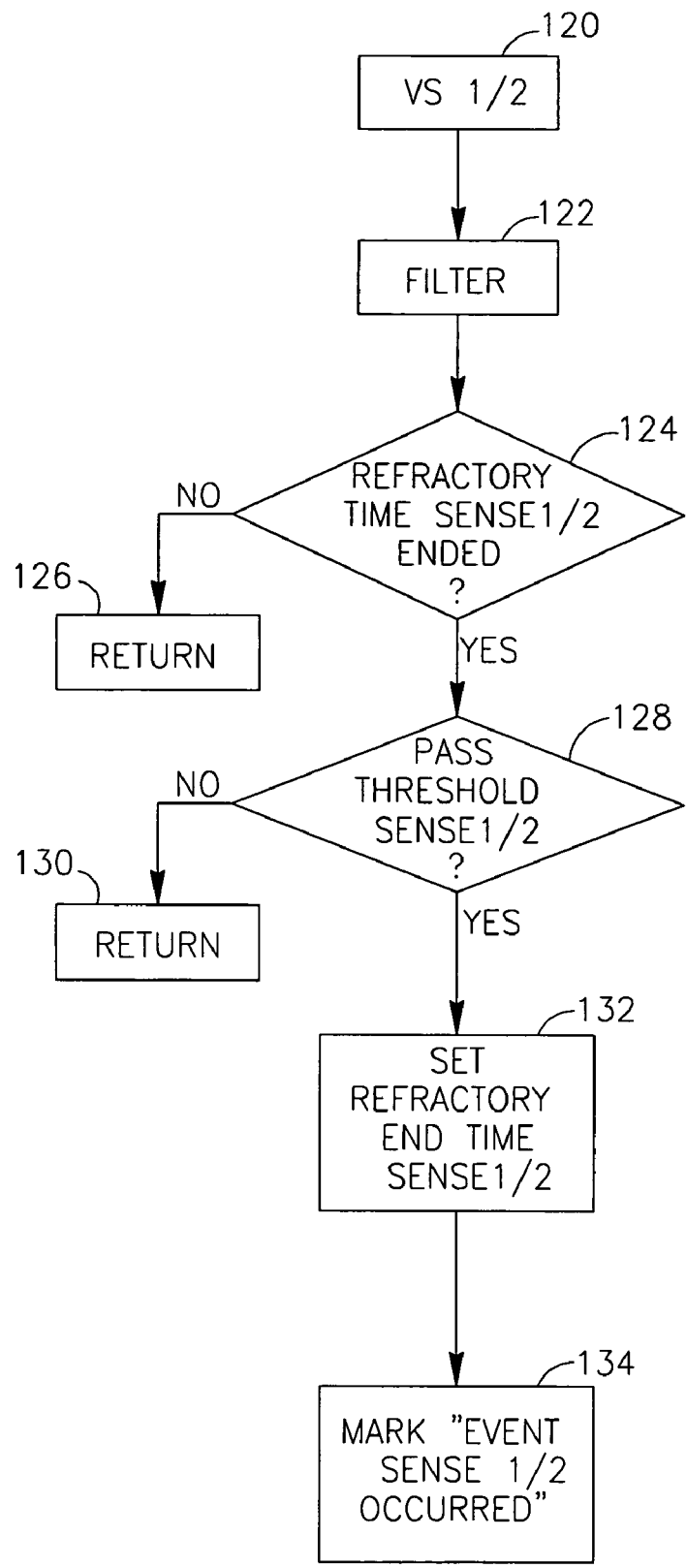
FIGS. 10-13, 14A-14B, and 15A-15B are schematic flow diagrams illustrating the steps of a specific implementation of the CCM delivery control method schematically illustrated in the functional block diagrams FIGS. 9 and 10.

Reference is now made to FIGS. 10-13, 14A-14B, and 15A-15B which are schematic flow diagrams illustrating the steps of a specific implementation of the CCM delivery control method schematically illustrated in the functional block diagrams FIGS. 9 and 10.

FIG. 10 illustrates the steps of an implementation of the event detecting block 102A of the detection block 100 (FIG. 8). The steps described are performed on the signals received from each of the ventricular channels VS1 and VS2. It is noted that while only one common scheme (flow chart) is shown for the sake of brevity of presentation, the steps for analyzing the signals from the VS1 and VS2 ventricular local sense channels may be performed in parallel (simultaneously) and independently for each of the channels VS1 and VS2.

The program receives the signals VS1 and VS2 (step 120), The signals are suitably filtered (step 122). The program then checks whether the refractory time for each of the channels VS1 and VS2 has ended (step 124). The refractory time of each of the ventricular channels VS1 and VS2 is a predetermined time period (which may be user programmable) which determines a time period starting from the detection of a PACE or SENSE. The refractory time for VS1 may be different then or equal to the refractory time of the channel VS2 (depending, inter alia, on the pacing site and on the specific sites of positioning of each ventricular local sense electrodes). After a PACE is detected, a counter starts counting the time for each of the refractory periods of each of the channels VS1 and VS2.

If the refractory time period of a channel (either VS1 or VS2) has not ended yet, the program returns to the beginning of the loop of the checking step 124 for the appropriate channel, to continue the checking (step 126). If the refractory time period of a ventricular channel (VS1 or VS2) has ended, the program checks if the channel signal passed the threshold test set for the appropriate channel (step 128).

In the threshold test for the local sense ventricular channels VS1 and VS2, the channel signal is tested to find if the signal exceeded a predetermined voltage level (the threshold is TH1 for the Channel VS1 and TH2 for the channel VS2). If the threshold was not crossed, the program returns control (step 130) to the beginning of step 128 and continues to check for threshold passing. If the threshold was crossed, the program sets a refractory end time for the relevant channel VS1 or VS2 (step 132) and marks (sets a flag) "EVENT SENSE 1 OCCURRED" or "EVENT SENSE 2 OCCURRED" depending on the relevant channel in which the threshold was crossed (step 134).

Figure 11:
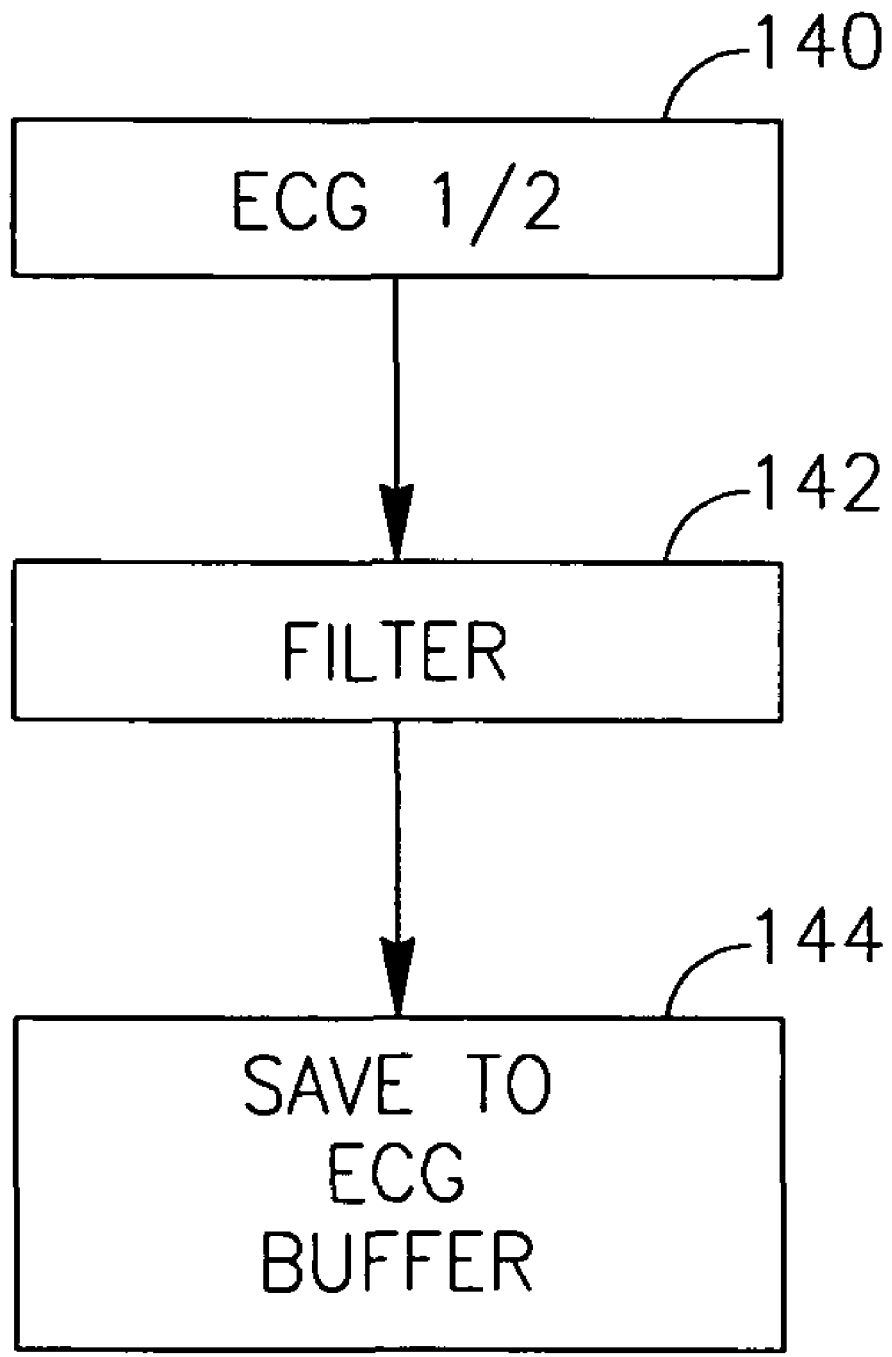

FIG. 11 illustrates the steps of an implementation of the event detecting block 102B of the detection block 100 (FIG. 8). The steps described are performed on the signals received from each of the global ECG channels ECG1 and ECG2. It is noted that while only one common scheme (flow chart) is shown for the sake of brevity of presentation, the steps for analyzing the signals from the global ECG channels ECG1 and ECG2 may be performed in parallel (simultaneously) and independently for each of the global channels ECG1 and ECG2.

The program receives the global signals ECG1 and ECG2 (step 140), The signals are suitably filtered (step 142). The program then saves the recorded global ECG channels ECG1 and ECG2 in a suitable buffer (ECG buffer). The buffer may be any type of memory device (not shown) or storage device (not shown) known in the art communicating with the processor controller or CPU in the CCM control device. The stored ECG signals may be later used in the decision block for comparison to the template (template test), and for any other purposes such as for updating dynamic or adaptive templates and the like.

Figure 12:
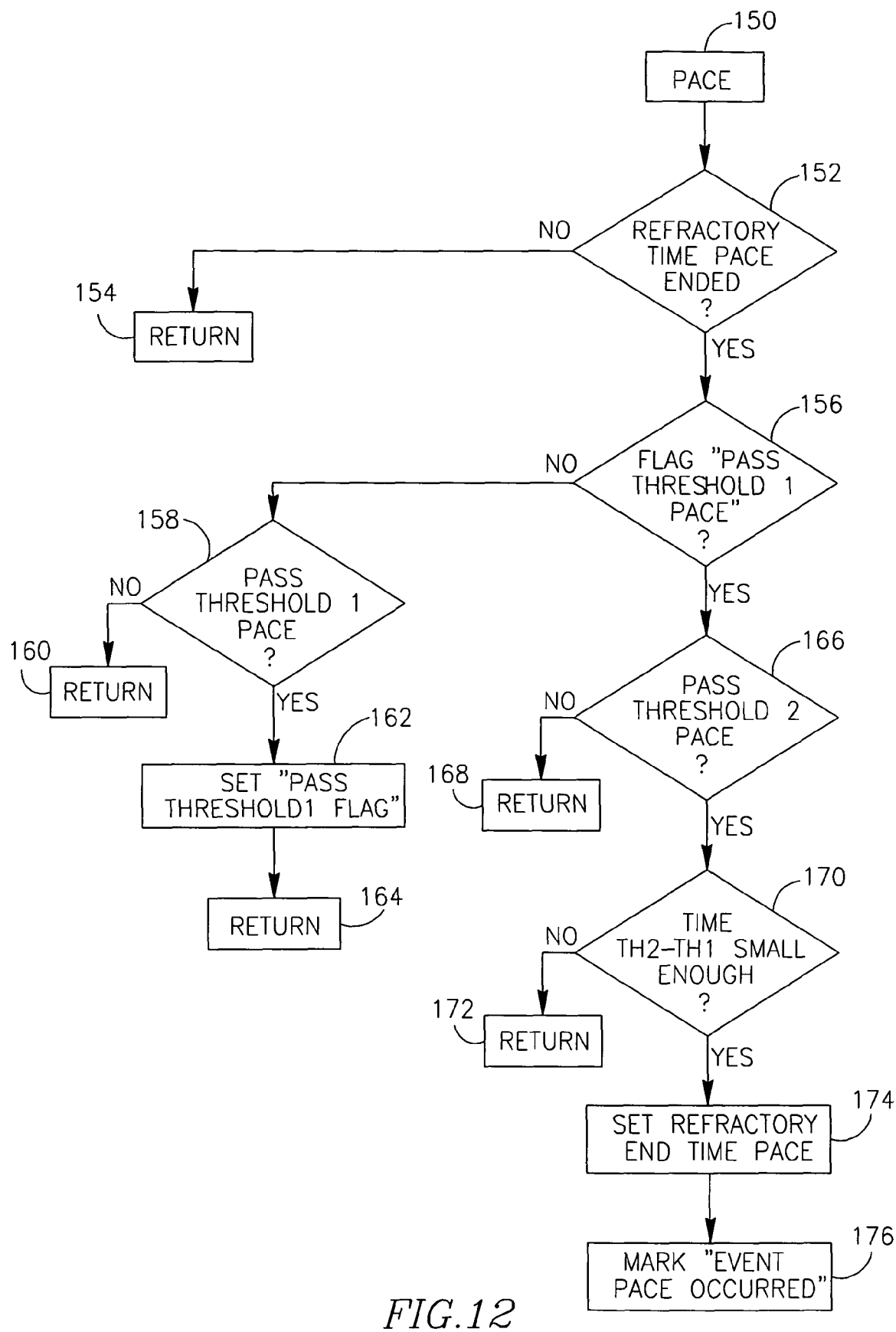

FIG. 12 illustrates the steps of an implementation of the event detecting block 102B of the detection block 100 (FIG. 8). The program receives data from a PACE Channel. The Pace channel may be any of the channels containing cardiac signals which are pacing related or contain electrical signals associated with the pacing of the heart (such as, for example VS1, VS2, ECG1, ECG2 or any combination of such signal channels such as a signal obtained from analog or digital subtraction or addition of these channels—in one possible practical example, one may use ECG1-ECG2 as the pace channel).

When the program receives a data point of the pace channel, the program checks if the refractory end pace time ended (step 152). The refractory pace time end is the end of a preset (user programmable) time period which begins after the first detection of a PACE event in the pace channel. If the refractory pace time period has not ended, the programs returns control (step 154) and waits for the next pace channel data point. If refractory pace time period has ended, the program checks whether the flag "PASS THRESHOLD 1 PACE" is on (step 156). This flag is raised if the pace event crossed the first pacing threshold (which is a user programmable threshold value). If the flag "PASS THRESHOLD 1 PACE" is not on (meaning that there was no previous crossing of pace threshold 1), the program checks whether the current pace channel data point crossed the first pace threshold 1 (step 158).

If the current pace channel data point did not cross the first pace threshold 1, the program returns control and waits for the next data point (step 160). If the current pace channel data point crossed the first pace threshold 1, the program sets "PASS THRESHOLD 1 FLAG" on (step 162) and returns control (step 164). The program then checks whether the current pace channel data point crossed a second pace threshold—"pace threshold 2" (step 166). If the current pace channel data point did not cross the pace threshold 2, the program returns control and waits for the next data point (step 168). If the current pace channel data point crossed the pace threshold 2, the program sets the refractory end time pace—meaning that a pace event refractory period end point time is computed and stored (Step 174) and a flag "EVENT PACE OCCURRED" is set (step 176) to indicate that a PACE event has occurred.

Figure 13:
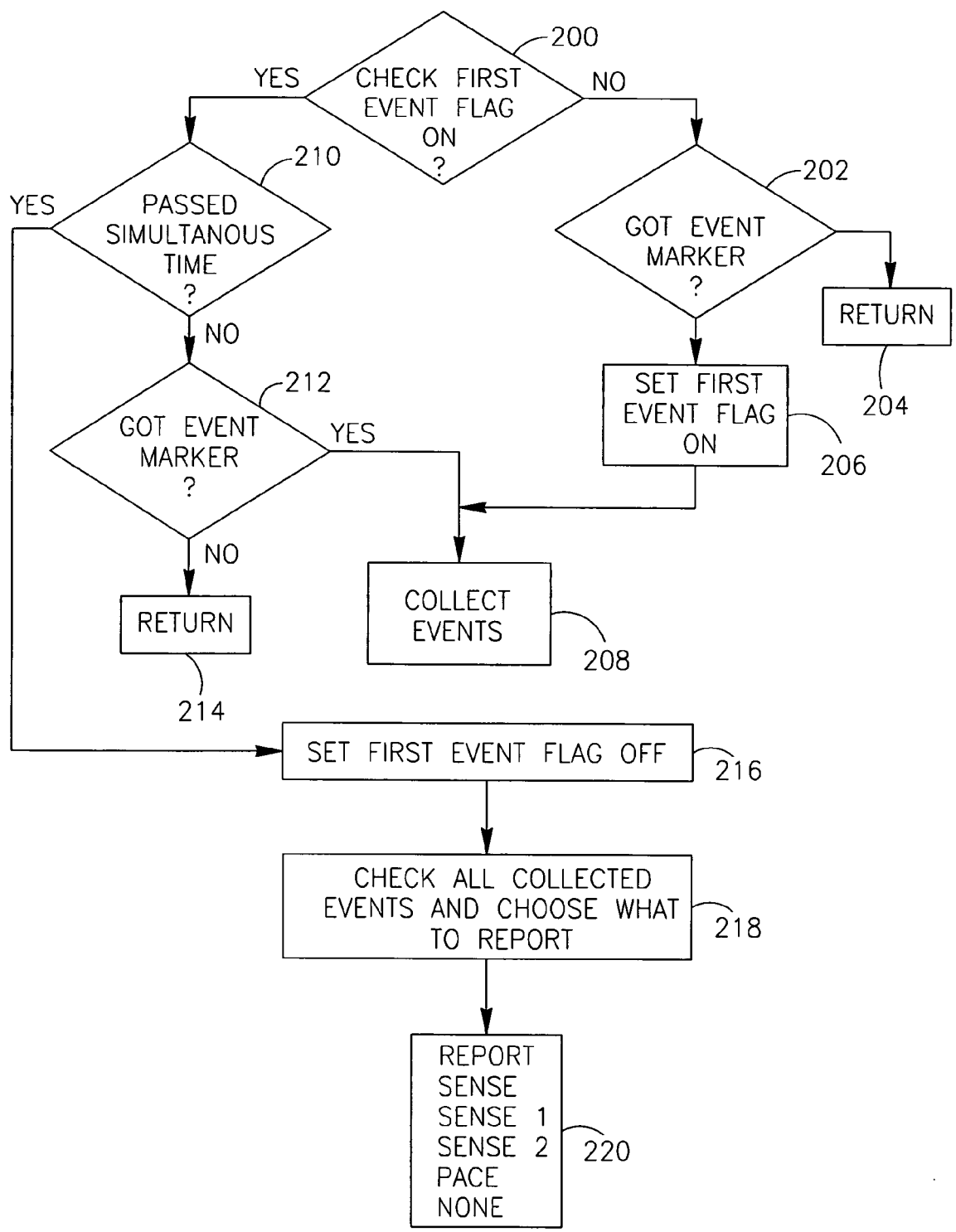

FIG. 13 illustrates the steps of an implementation of the event collector block 104 of the detection block 100 (FIG. 8). The program checks whether the first event flag is on (step 200). If the first event flag is not on, the program checks whether there is an event marker (step 202). If there is no event marker on, the program returns control (step 204) and waits for the next data point. It there is an event marker on, the program sets the first event flag on (step 206) and collects the events by storing the relevant events that occurred (step 208).

If the first event flag is on, the program checks whether the simultaneous time test was passed (step 210). The simultaneous time is a user programmable preset time period. In accordance with one possible embodiment, the simultaneous time period may be in the range of 6-25 milliseconds, but other different values may also be programmed by the user. Events in any channel which occurred within time period are considered as related events and are recorded as relevant events in the "collect events" step 208. If the simultaneous time test is not passed (which means that the current event was outside of the simultaneous time period invoked by the previous event) the program checks whether an event marker is on (step 212). If an event marker is not on, the program returns control (step 214) and waits for the next data. an event marker is on, the program collects the events (step 208).

If the simultaneous time test is passed (which means that the current event occurred within of the simultaneous time period invoked by the previous event), the program sets the first event flag OFF (step 216), checks all the collected event data to decide what report marker to report to the decision block 110 (step 218) and reports to the decision block 110 based on the decision (received on in step 218) a single report marker selected from the following report markers: SENSE, SENSE1, SENSE2, PACE, and NONE (step 220). The decision of which report mark is to be output to the decision block 110 is performed based on preset (possibly user programmable) rules which may be stored in a suitable lookup table (LUT). For example, in accordance with an exemplary, non-limiting embodiment of the present invention, the lookup table may be configured to include the following decision rules:

a) If there was an event detected in VS1—the output is report marker SENSE1.

b) If there was an event detected in VS2—the output is report marker SENSE2.

c) If there was an event detected in VS1 VS2 within the set simultaneous time period—the output is report marker SENSE.

d) If any of the following event combinations occurred within the set simultaneous time period: I. PACE only II. VS1 and PACE III. VS2 and PACE IV. VS1 and VS2 and PACE.

Then the output is report marker PACE.

e). If one or more of predetermined user definable set of conditions was detected, then output is report marker NONE.

It is noted that the user definable conditions may vary depending on the specific embodiment of the present invention. For example, one such user definable condition included in the decision rule e above may be the detection of noise according to certain criteria (for example, if the RMS noise level is computed for certain selected parts of the channel signal(s), then a condition may be met if the current noise level exceeds a certain user defined or automatically determined noise threshold, and this may trigger the report of a NONE report marker. In another possible example, if three VS1 events are detected within the simultaneous time period, this may trigger the report of a NONE report marker). It is, however, noted that the use of these specific decision rules is optional, is not obligatory to the implementation of the embodiments of the present invention, and that many other types of decision rules and/or combinations of decision rules may be used for triggering an output of a report marker NONE.

It is also noted that the methods devices and programs of the present invention may also be successfully operated in cases where the NONE report marker is not included in the list of possible report markers that may be output by the step 220 of FIG. 13.

Figure 14A:
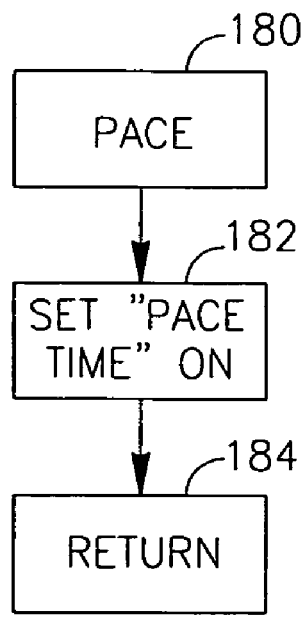
Figure 14B:
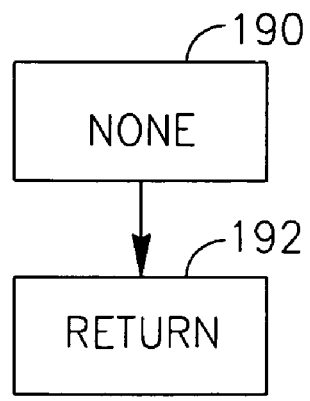

FIGS. 14A-14B illustrates the steps of an implementation of part of the input signal block 112 of the decision block 110 (FIG. 9). The program checks the incoming report marker received from the detection block 110. In FIG. 14A, if the program receives a report marker PACE (step 180) the program sets marker "PACE TIME" ON (meaning that the beat has been identified as a paced beat) and returns control to the other processes running in the decision block (step 184). Turning to FIG. 14B, if the program receives a report marker NONE (step 190) the program returns control to the other processes running in the decision block (step 192).

Figure 15A:
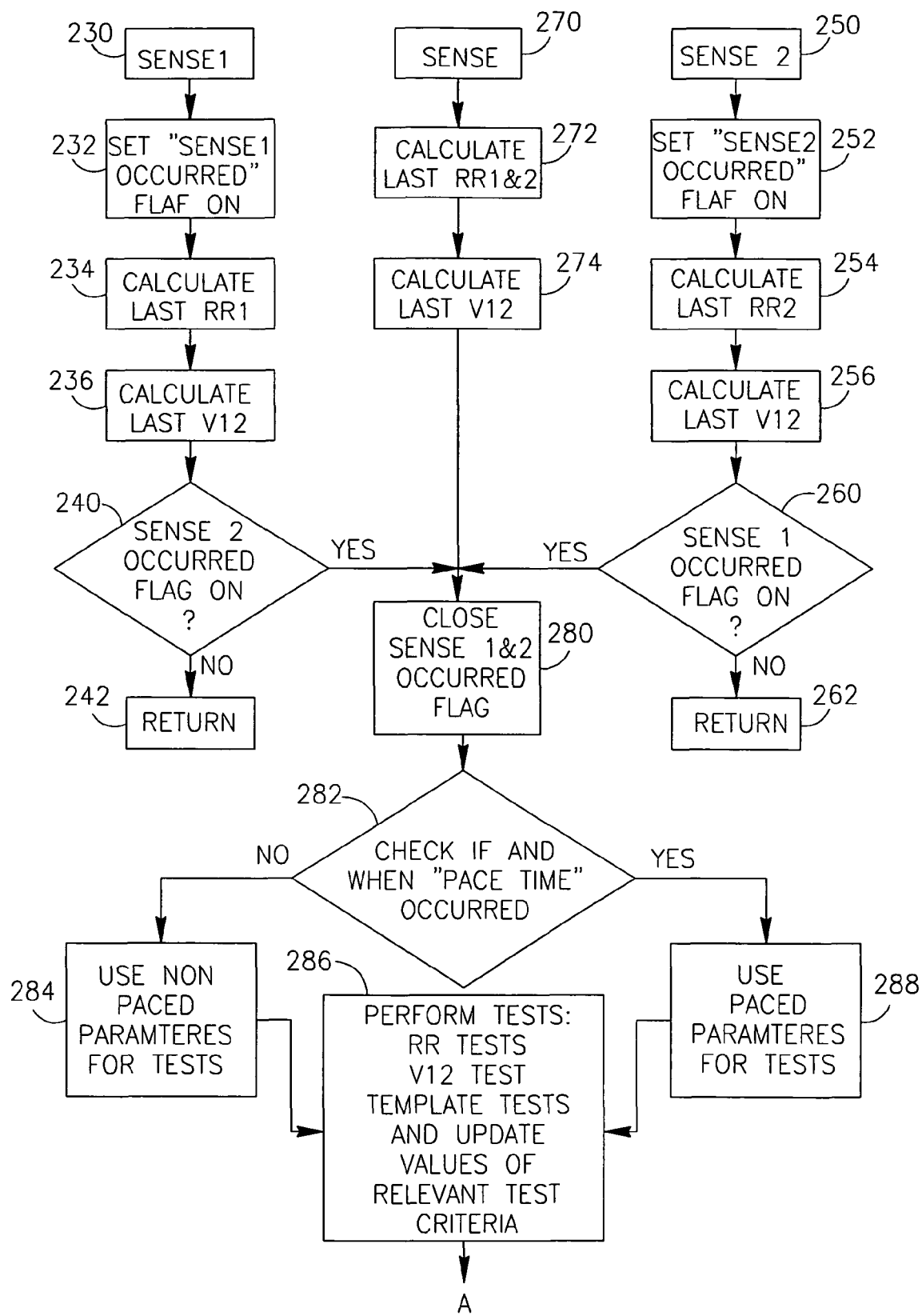
Figure 15B:
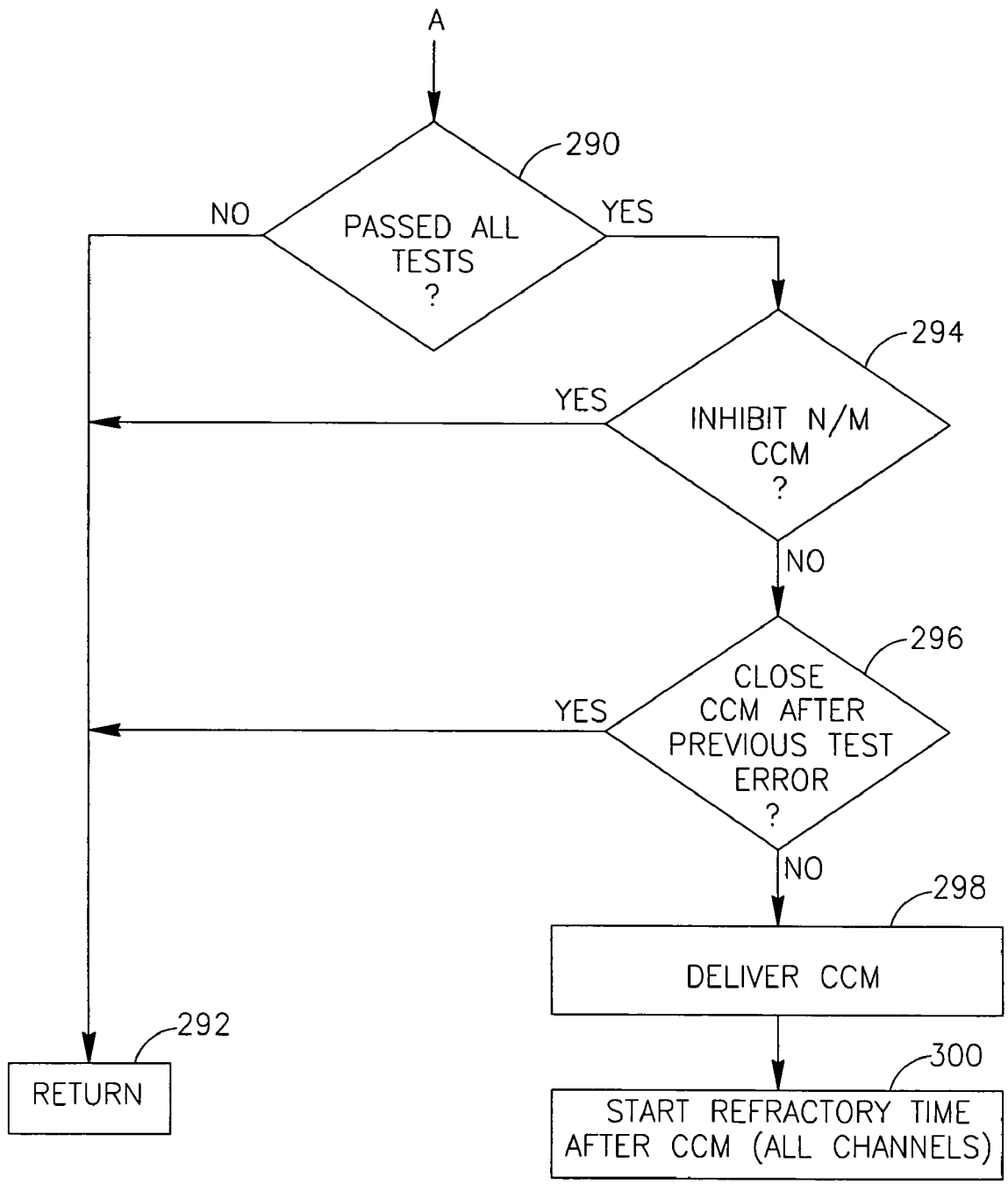

In FIGS. 15A and 15B, the program may start at one of step 230, or step 270, or step 250, depending on the specific report marker received from the report generating block 106 of FIG. 10.

If the program receives a report marker SENSE1 (step 230), the program sets the "SENSE1 OCCURRED" flag on (step 232), calculates and stores the last RR1 (step 234) by using the stored timing data of the current and previous times of SENSE1 events, and calculates and stores the last V12 (step 236). The last V12 is the value of the delay between detecting a sense in channel VS1 and in VS2. The program then checks whether the "SENSE2 OCCURRED" flag is on (step 240). If the "SENSE2 OCCURRED" flag is not on, the program returns control and waits for the next data (step 242). If the "SENSE2 OCCURRED" flag is on, the program closes the "SENSE1 OCCURRED" flag and the "SENSE2 OCCURRED" flag by turning both flags off (step 280).

If the program receives a report marker SENSE2 (step 250), the program sets the "SENSE2 OCCURRED" flag on (step 252), calculates and stores the last RR2 (step 254) by using the stored timing data of the current and previous times of SENSE2 events, and calculates and stores the last V12 (step 256). The program then checks whether the "SENSE1 OCCURRED" flag is on (step 260). If the "SENSE1 OCCURRED" flag is not on, the program returns control and waits for the next data (step 262). If the "SENSE1 OCCURRED" flag is on, the program closes the "SENSE1 OCCURRED" flag and the "SENSE2 OCCURRED" flag by turning both flags off (step 280).

If the program receives a report marker SENSE (step 270), the program calculates and stores the last RR1 and the last RR2 (step 272) by using the stored timing data of the current and previous times of the SENSE1 and SENSE2 events, and calculates and stores the last V12 (step 274). The program then closes the "SENSE1 OCCURRED" flag and the "SENSE2 OCCURRED" flag by turning both flags off (step 280).

After the completion of step 280 (reached through any appropriate path of FIG. 15A as dictated by the report marker type as disclosed hereinabove, the program checks whether a "PACE TIME" occurred and when it occurred (step 282). If a PACE TIME has not occurred, the program fetches the appropriate set of parameters intended for use in Non-paced beats (step 284) and proceeds to use the fetched Non-paced test parameters in the tests, performs the tests RR1 test, RR2 test, V12 test and TEMPLATE test using the fetched parameters and updates the relevant dynamic test parameters by suitably recalculating the dynamically updated parameters using the current RR (step 286). If a PACE TIME has occurred, the program fetches the appropriate set of parameters intended for use in paced beats (step 288) and proceeds to use the fetched paced test parameters in the tests, performs the tests RR1 test, RR2 test, V12 test and TEMPLATE test using the fetched (paced) parameters and updates the relevant dynamic test parameters by suitably recalculating the dynamically updated parameters using the current RR (step 286).

The program then checks whether all the tests (RR1 test, RR2 test, V12 test and TEMPLATE test) were successfully passed (step 290). If not all the tests were passed, the program returns control and waits for the next data (step 292). If all the tests were passed, the program proceeds to test whether the current beat is marked as "INHIBIT N/M CCM" (step 294). If the current beat is marked as "INHIBIT N/M CCM" this means that the program is currently set to inhibit the delivery of CCM signals in N out of M cardiac beats (where M>N), and that the current beat is marked as one of these N beats in which the CCM signal delivery should be inhibited. The program then transfers control to step 292 without delivering a CCM signal(s) to the heart, and waits for the next data. If the current beat is not marked as "INHIBIT N/M CCM" the program checks whether there is a current instruction to close (inhibit) CCM after a previous test resulted in error (step 296). Wherein "error" is defined as any condition in which at least one test failed or caused the device to inhibit the delivery of a CCM in the preceding beat cycle.

If there is a current instruction to close (inhibit) CCM signal delivery after a previous test resulted in error, the program returns control and waits for the next data without delivering a CCM signal (step 292). If there is no current instruction to close (inhibit) CCM signal delivery (due to previous error), the program delivers a CCM signal to the heart (step 298) and starts a refractory time period during which the program ignores the data on all channels (step 300) to avoid any spurious signals due to the effects of the CCM signal associated electrical artifacts.

Figure 16:
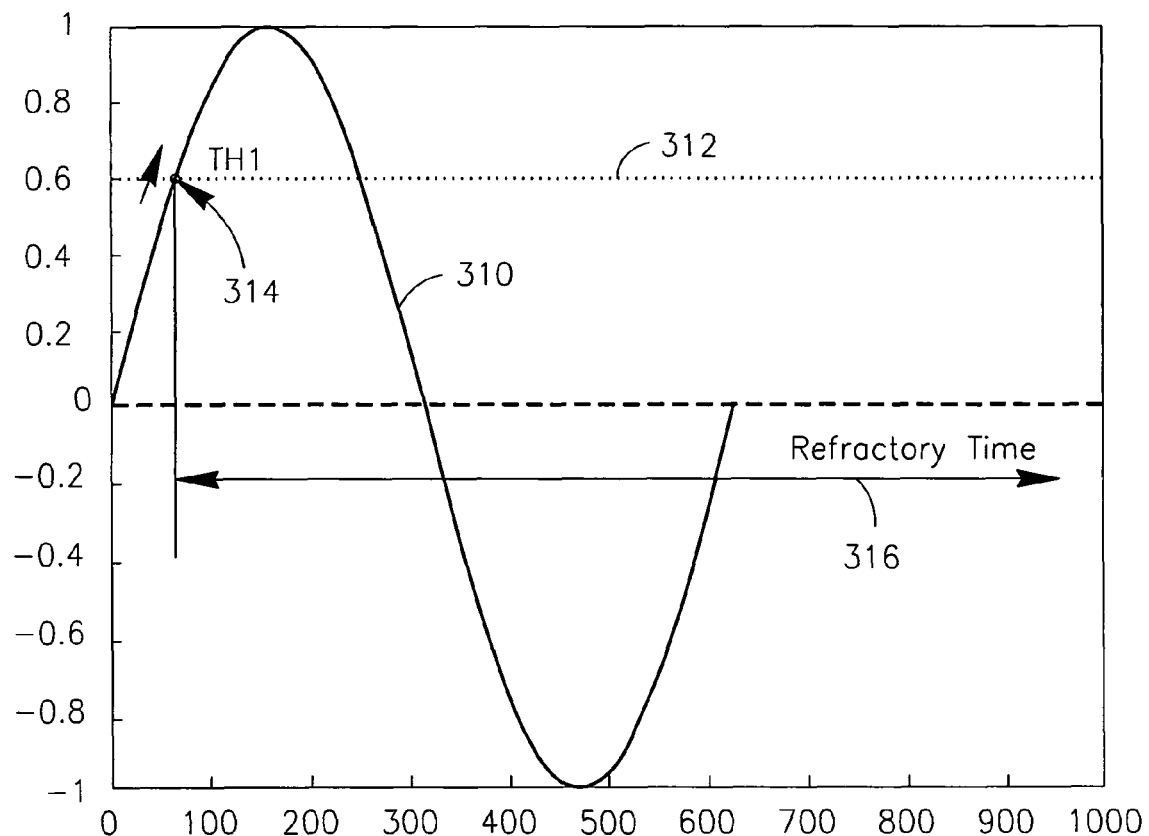
FIG. 16 is a schematic diagram illustrating one possible embodiment of a method of implementing the single threshold for the ventricular local sense channels of the present invention.

Reference is now made to FIG. 16 which is a schematic diagram illustrating one possible embodiment of a method of implementing the single threshold for the ventricular local sense channels of the present invention.

The curve 310 represents a schematically drawn sense channel recorded signal (sense event), the vertical axis represents the signal amplitude in arbitrary units and the horizontal axis represents time in arbitrary units. The horizontal line 312 represents the user definable voltage threshold set for the signal. The signal is arbitrarily shown as the signal recorded in channel VS1. The signal amplitude crosses the threshold TH1 at the point 314 which is detected and recorded as a SENSE1. The double headed arrow 316 represents the duration of the refractory period activated after the threshold crossing of point 314. During this refractory period all other signals in this channel are ignored. The threshold for the second channel VS2 may work similarly.

However, as both the value TH1 and the duration of the refractory period 314 are user programmable depending, inter alia on the user judgment of the best settings, the threshold TH1 and the refractory period duration of channel VS1 need not be identical to the threshold TH2 and the refractory period duration of channel VS2. It is noted that the thresholds Th1 and TH2 may be set at either positive voltage values or a negative voltage values, depending, inter alia on the polarity of the electrodes and on the shape of the resulting recorded sense signal.

Figure 17:
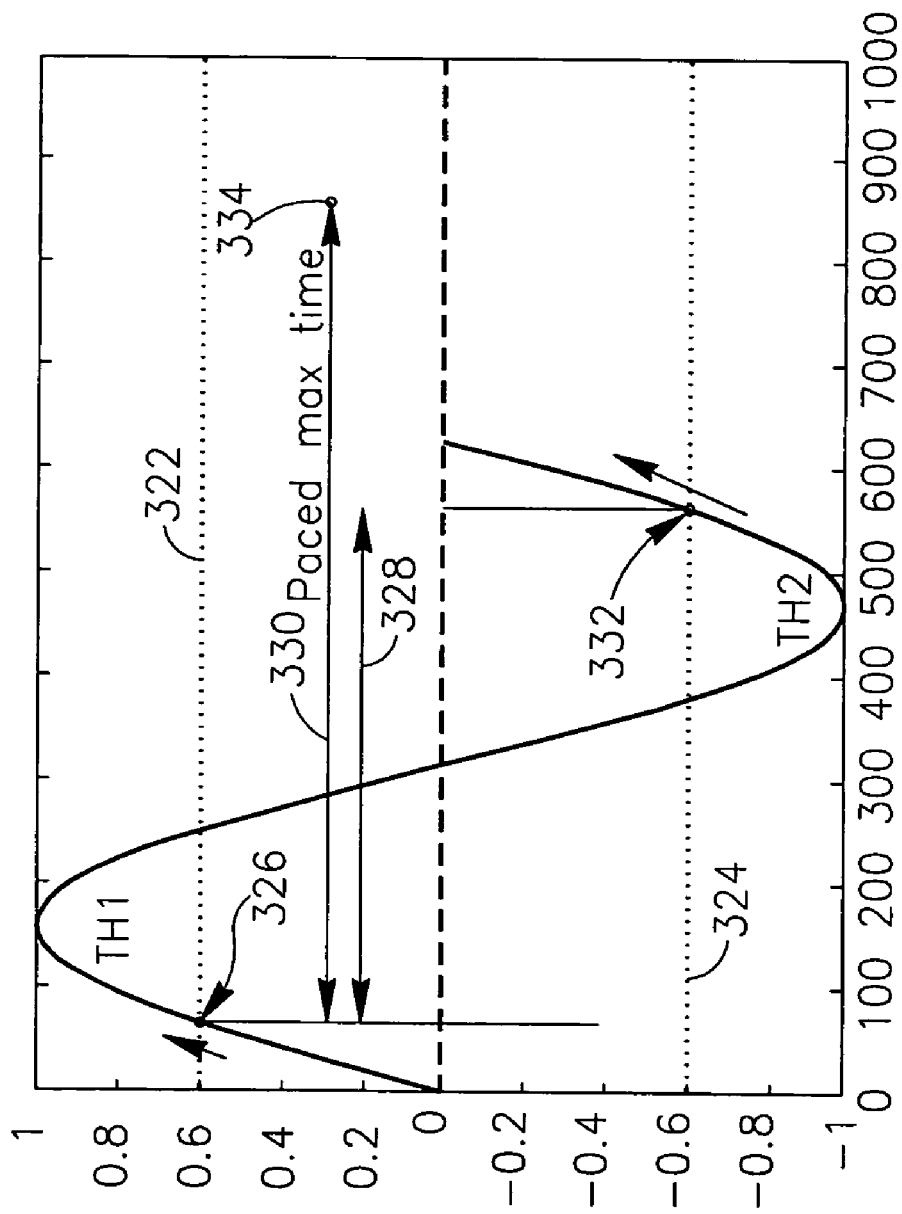
FIG. 17 is a schematic diagram illustrating one possible embodiment of a method of implementing the double threshold and time proximity test for the pace detection algorithms of a possible embodiment of the present invention.

Reference is now made to FIG. 17 which is a schematic diagram illustrating one possible embodiment of a method of implementing the double threshold and time proximity test for the pace detection algorithms of a possible embodiment of the present invention. The curve 320 represents a schematically drawn pace channel recorded signal (which may in practice be any of the channels VS1, VS2, ECG1, ECG2 or any other combination of these channels obtainable by a mathematical manipulation such as subtraction addition or the like). The vertical axis represents the signal amplitude in arbitrary units and the horizontal axis represents time in arbitrary units. The horizontal lines 322 and 324 represent the user definable first voltage threshold TH1 set for the signal and the user definable first voltage threshold TH2 set for the signal, respectively.

The signal amplitude crosses the (positive) threshold TH1 at the point 326. The signal amplitude crosses the (negative) threshold TH2 at the point 332. The double headed arrow 328 represents the delay period between the first threshold crossing point 326 and the second threshold crossing point 332. The double headed arrow 330 represents a user programmable maximal pace time period which starts at the point 326. If the second threshold crossing point occurs after the end of 334 of the maximal pace time period, the algorithms do not detect this event as a pace event.

Reference is now made to FIGS. 18-21 which are schematic diagrams helpful in understanding the various test criteria and test parameters used in the testing algorithms of the decision block of FIG. 9.

Figure 18:
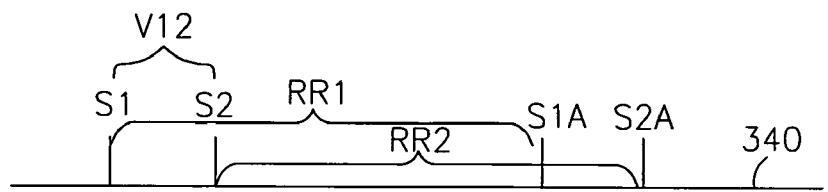
FIGS. 18-21 are schematic diagrams helpful in understanding the various test criteria and test parameters used in the testing algorithms of the decision block of FIG. 9.

In FIG. 18, the horizontal line 340 represents time. The vertical lines S1 and S1A represent the times of occurrence of two sense events (threshold crossings) of the first ventricular local sense channel VS1. The vertical lines S2 and S2A represent the times of occurrence of two sense events (threshold crossings) of the second first ventricular local sense channel VS2.

V12=distance in msec between SENSE1 at the first electrode to SENSE2 at the second electrode.

RR1=distance in msec between the current sense1 (S1A) and the previous sense1 (S1).

RR2=distance in msec between the current sense2 (S2A) and the previous sense2 (S2).

The tests include TESTS—RR1, RR2, V12

RR1, RR2 and V12 test are similar, description will be done on RR but it is relevant to all of them.

Figure 19:
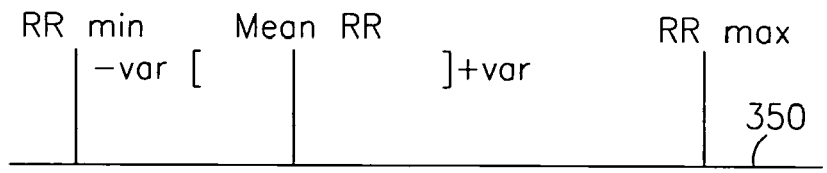

Turning to FIG. 19, the horizontal line 350 represents the parameter value in arbitrary units.

The following definitions hold:

Fixed limit—if any RR result is beyond those limits (larger than the RR fixed limit) we consider the test result as an unacceptable beat. These fixes limits are not adaptive and can be changed only by the user and will be called as RR min and RR max (represented by the two vertical lines labeled RR min and RR max of FIG. 19.

Adaptive limit: ±VAR are fixed limits around the mean RR (the mean RR is adaptively changing). here if the current RR is beyond those limits (and before RR min and RR max) we consider the test result as atypical beat.

Mean RR—in every test result we update this parameter mean RR (see updating tests)

DEFINITIONS

Figure 20:
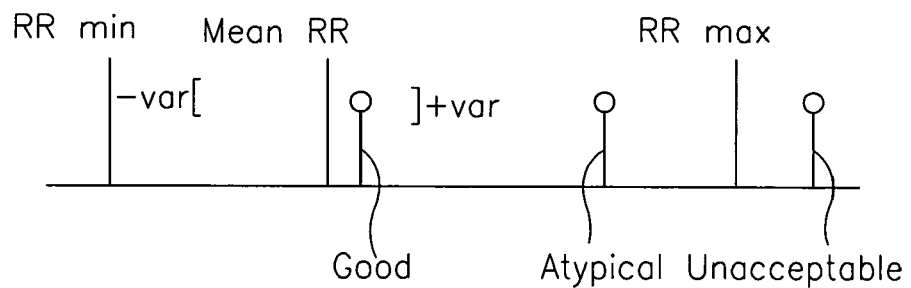

See FIGS. 19-20

Good: A beat that meets all criteria, including the adaptive criteria

Atypical: A beat that meets all fixed limits, though does not meet the adaptive limits (±Var), and is thus different than the recent beats.

Unacceptable: A beat having an RR that exceeds any of the fixed limits (i.e RR is smaller in value than RRmin or is larger in value than RRmax.

Short Description:

if ($RR<RR$ min) or ($RR>RR$ max)) then
    This_sense=Unacceptable else if ($RR<mean\_RR$+Var) and ($RR>$mean$\_RR-$Var)
    then This_sense=GOOD else This_sense=Atypical Updating after the Test If a beat is classified as Unacceptable by at least one criterion, no parameter will be adapted according to that beat. If a beat is classified as Atypical under at least one criterion, the adaptation of the means (e.g. RR_mean) and the template will be with weak weight to the current beat. In this way, an Atypical beat will have a very limited influence on the mean value of an updated parameter, and slow adaptation is obtained. This approach allows the system to adapt to physiological changes that the patient may experience.

If a beat is classified as Good under all criteria, the adaptation of the means (e.g. RR_mean) and of the template will be with more weight assigned to the current beat. In this way, a Good beat will be more influential, and faster adaptation is obtained. In this case (of Good beat), CCM signal delivery is allowed (assuming CCM is enabled and not inhibited by previous beats).

The adaptation rate may be determined by a coefficient "alpha", with values suitable for Good, and Atypical conditions. For example: Atypical_alpha<Good_alpha<1

Adaptation may be of the mean, templates and variances, although some of these may be non-adaptive (e.g. allowed variance).

For example:

New_Mean_$RR$=alpha*$RR$+(1-alpha)*Mean_$RR$

Adaptation is using the Good_alpha or Atypical_alpha (alpha=Good_alpha/Atypical_alpha) as appropriate or not updated by unacceptable beat.

Global Electrogram Templates

In accordance with an embodiment of the invention, the devices and systems described herein may use ECG templating.

It is noted that when ECG recording of the signals is performed as disclosed hereinabove, the resulting ECG signal may include a contribution from local electrical events which occurred at the local site used for performing the local bipolar recording (such as, for example the local right ventricular recording site). Therefore, in accordance with an embodiment of the invention, in order to reduce this contribution of such "local information" to the recorded ECG signal, it may be possible to subtract a function of the simultaneously recorded local signal (for example, a function of the signal bipolarly recorded at the right ventricular site) from the recorded ECG signal to obtain a "cleaner" or filtered form of the Global ECG signal for use in computing the template and for use in comparing to the template.

Typically, when two local ventricular electrodes are used for bipolar recording the locally sensed ventricular signal and the device can and a single ventricular electrode are used to bipolarly record ECG signal, the general form of such a filtered ECG signal is represented as:

$$ECG_{(FILTERED)} = (V_A - V_{CAN}) - F(V_A - V_B)$$

Wherein, $V_A$ represents the voltage at the first ventricular electrode A of a ventricular electrode pair;

$V_B$ represents the voltage at the second ventricular electrode B of a ventricular electrode pair;

$V_{CAN}$ respresents the voltage of the can electrode;

$(V_A - V_{CAN})$ represents the voltage difference recorded between the single local ventricular electrode A and the can of the CCM device (or the pacemaker device); and $F(V_A - V_B)$ represents a function of the voltage difference recorded between the pair of ventricular electrodes A and B.

It is noted that conveniently, the function F may be any suitable function, such as but not limited to multiplication or division by a constant, a linear filter, or any other type of suitable function.

In accordance with one, non-limiting embodiments of the invention the filtered ECG signal may be used in the forms represented below:

$$ECG_{(FILTERED)} = (V_A - V_{CAN}) - C(V_A - V_B)$$

Wherein C is a constant having a value between 0-1.

For example, some simple forms of which may be used are:

$$ECG_{(FILTERED)} = (V_A - V_{CAN}) - (V_A - V_B); (C=1)$$

or $$ECG_{(FILTERED)} = (V_A - V_{CAN}) - 0.5(V_A - V_B); (C=0.5)$$

However, many other different types of the function F may also be used.

It is noted that in accordance with an embodiment of the present invention it is possible to use for determining the presence of ectopic events two or more differently filtered signals acquired by applying different filtering characteristics to the same signal for accentuating either global events or conversely for accentuating local events.

For Example, it is possible to use a signal recorded between a local ventricular sensing electrode and a can electrode (unipolar recording) and to apply to filter the same signal twice to obtain two filtered output signals: a first high-pass filtered output signal that will accentuate locally sensed electrical events (due to better passing of higher frequency components typically contained in local events) and a second low-pass filtered output signal that will more effectively suppress locally sensed electrical events (due to better passing of low frequency components typically present in global events). By suitably processing these two differently filtered output signals (such as by subtracting the first filtered output signal from the second filtered output signal it is possible to selectively accentuate either global or local electrical events and to perform the detection of relevant ventricular ectopies in the presence of AF or other supra-ventricular activity, as disclosed in detail hereinabove.

The methods used in the present invention may include the use of different metrics (a score given for a match between a measured signal and the template) for comparison of the template to a signal.

Metrics for Calculating the Degree of Matching Between Measured Pulse and Template The following equations 1-7 below represent non-limiting examples of metrics (mathematical expressions) usable for the calculation of the degree of match (or error) between a measured signal and a stored template. The template is (preferably dynamically) calculated based on previous sensed signals (For example, the detection and the template may be based on the signals recorded in the 120 milliseconds preceding the time of the decision of whether to enable the delivery of a CCM signal or the delivery of biventricular pacing signals, or both, however, different lengths of this time period may also be used, such as but not limited to 150 milliseconds, or time values in the range of 30-200 milliseconds, or other suitable values may also be used). When the calculated error is below a set threshold, the sensed signal is considered "acceptable" and the CCM (or the biventricular pacing, or both) is not inhibited (unless it is inhibited for another independent reason) and the template is updated "fast" (in the sense that the new recorded signal is given higher weight in the calculation of the updated template). When the calculated error is above the set threshold, the signal is considered "problematic" and the delivery of a CCM signal (or the biventricular pacing, or both) is inhibited, and the measured new signal is given little or no weight in the updating of the template.

In the following equations,

X represents the stored template;

Y represents the measured (current) signal; and t represents the time measured from the "beginning" of the signal.

w represents the time window within which the template will be matched, $Factor_{(t)}$ represents a temporal weighting factor, and $max(|X(t)|)$ represents the peak voltage value within the template.

$Factor_{(t)}$ of equation (5) below is a temporal weighting factor which takes into account the temporal position of each data point within the new measured signal and the template, such that deviations of the currently measured signal from the temporally corresponding value of the template that occur at a time within the measured signal duration where they are more meaningful, are given more weight than such deviations that occur at a time when they are expected in normal heartbeats. For example, $factor_{(t)}$ may have a value of about 1 at the "beginning" part of the signal ("Beginning" herein refers to the parts of the sensed signal that are temporally closer to the time point at which the decision is expected whether to enable or disable the delivery of the CCM or pacing signals. This means that such parts of the signal have actually occurred temporally later within the beat cycle).

It is noted that, as these "beginning" portions of the analyzed signal are stored in a memory buffer, they may be retrieved and checked earlier and hence they are herein termed "beginning" part of the signal even though they have actually occurred later in the beat cycle.

The value of factor$_{(t)}$ may gradually decrease for parts of the data that are positioned "later" (but actually occurred before the beginning portion of the data, as explained hereinabove) within the buffered data, until a period of time when the value of factor$_{(t)}$ reduces much more quickly. Thus, a form of temporal weighting is used which assigns a higher weight to the more relevant parts of the sensed signal. Thus, In accordance with an embodiment of the present invention, equation (6) below may be used, by selecting, assigning and storing an appropriate set of values of factor$_{(t)}$ (such as, for example in a suitable look up table) for each data point included in the buffered signal (and in the template), such that in the computation of the template match (or error) any deviations of the sensed signal from the template which occur at time periods in which In this way the computed error (or the computed match) between the currently sensed signal and the template (as well as the calculated error) is affected to a higher degree by certain parts of the sensed signal than by other parts of the sensed signal. The specific values of Factor$_{(t)}$ may be preset or may be manually set, depending, inter alia, on data obtained from recorded measurements in a particular individual or patient under various patient conditions and physiological states, or on data obtained from multiple measurements in a plurality of patients under various patient conditions and physiological states.

In equation (7), the index i represents the sensed signal number. The equation compares the current measurement of sensed signal i (Y(t,i)) with the most up-to-date template (X(t,i)) and with the template as it was calculated before taking the previous sensed signal (X(t,i−1)) into account.

$$\sum_{t \in w} |(X(t) - Y(t)|  \quad (1)$$

$$\sum_{t \in w} (X(t) - Y(t))^2 \quad (2)$$

$$\sum_{t \in w} \frac{|(X(t) - Y(t)|}{\max(|X(t)|)} \quad (3)$$

$$\frac{\sum_{t \in w} ((X(t) - Y(t))^2}{\sum_{t \in w} X^2(t)} \quad (4)$$

$$\frac{\sum_{t \in w} factor_{(t)} |(X(t) - Y(t)|}{\sum_{t \in w} factor_{(t)}} \quad (5)$$

$$\frac{\sum_{t \in w} |(X(t) - Y(t)|}{\sum_{t \in w} |X(t)|} \quad (6)$$

$$\frac{\sum_{t \in w} |(X(t, i) - Y(t, i)|}{\sum_{t \in w} |X(t, i-1)|} \quad (7)$$

It is noted that in equation 3 above the use of the expression max(|X(t)|) in the denominator represents normalization of the template (but normalization of the current signal Y may also be similarly used), which may be useful to reduce the effects of temporary phenomena on the computation. Such temporary phenomena may include, for example, sporadic changes in signal amplitude due to electrode movements or to any changes in the resistance of the tissue or in the interface between the electrode(s) and the tissue, or the like. The effects of such changes which are typically unrelated to the measured cardiac electrical activity may be reduced by using normalization of the current signal or of the template by dividing each data point in the signal by the value of the maximum data point, as is well known in the art.

It will be appreciated by those skilled in the art that the specific metrics (mathematical expressions) disclosed hereinabove for computing the degree of match (or the error) of the currently evaluated sensed signal to the template are given by way of example only and are not intended to limit the scope of the metrics that may be used in of the present invention. Thus, other different equations than those disclosed hereinabove may also be used in other embodiments of the invention.

The Template is used to match the current beat's global electrogram with the history of recent beats. The template relates to samples of the "ECG" channels within a time period (e.g. 100, 130, 150 msec, or the like) prior to the CCM delivery time. Testing the correlation of the current global electrogram with the template may be performed using various matching techniques, including, but not limited to, estimation of correlation, differences, weighted differences, etc. Likewise, morphological features (derivative, peaks, energy, spectrum, etc) may be extracted from the historical representation of the template and used to compare with the current beat.

Particular (non-limiting) examples of error (mismatch) function are as follows:
When
V=current beat global electrogram
Vt=template electrogram
sumA=sum from decision point and 150 msec before
   Err=sumA(absolute(V−Vt))
   Err=sumA(absolute(V−Vt)^2)
   Err=sumA(absolute(V−Vt))\sumA(absolute(Vt))
   Err=sumA(absolute(V−Vt))\max(Vt)
   Err=sumA(absolute(V−Vt))\min(Vt)
   Err=sumA(absolute(V−Vt)^2)\sumA(Vt^2)

Total energy of ECG may cover the entire QRS signal of the current beat (spanning from ~150 msec before the local sense until about ~150 after the local sense) when the beat has no CCM artifact. This measurement may be used by switching off CCM delivery for one beat once in every several beats, such as to see a clear QRS waveform on the ECG channel.
When
sumB=sum over the total energy of the QRS complex
   Err=sumA(absolute(V))\sumB(absolute(Vt))
   Err=sumA(V^2)\sumB(absolute(Vt))
   Err=sumA(absolute(V−Vt))\sumB(Vt)
   Err=sumA(absolute(V−Vt)^2)\sumB(Vt^2)

Figure 21:
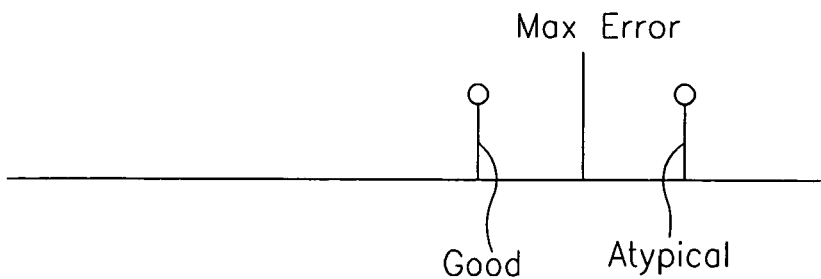

Referring now to FIG. 21, If Err is smaller than Max Error we will use Good_alpha, else we will use Atypical_alpha.

The template represents a typical representation of the recent history, for example by adapting as follows:

New_Template=alpha*ECG+(1-alpha)*Template

This computation is performed for every point along the template, synchronized to the local sense timing.

The devices and methods of the present invention have been experimentally tested in pigs. The following figures provide samples of actual data and computed dynamically adapting templates as recorded and processed and computed in the heart of a pig with two local sense channels (VS1 and VS2), two global ECG channels (ECG1 and WCG2) with unipolar recording against a distant electrode.

In all graphs of FIGS. 22-34 below, the horizontal axes of the graphs represent time in milliseconds and the vertical axes represent the signal amplitude in millivolts. It is noted that some of the data shown may represent amplified and filtered and/or conditioned signals).

Figure 22:
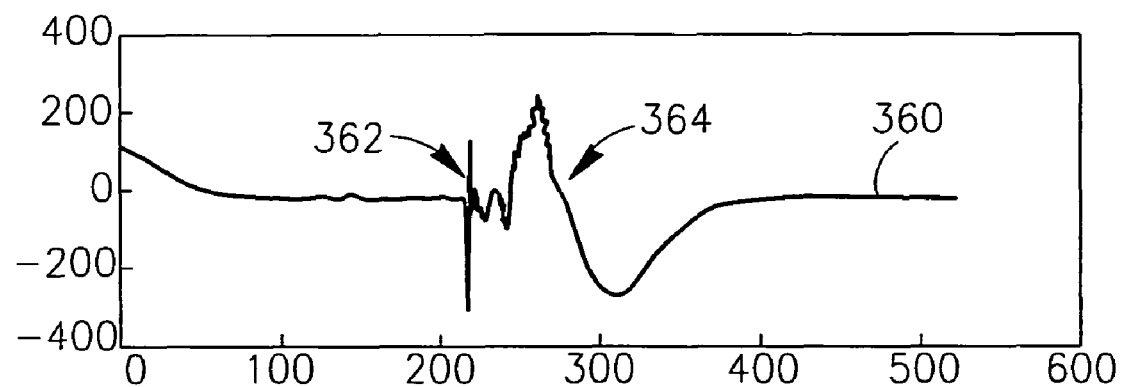
FIG. 22 is a schematic graph illustrating exemplary non-filtered digitized data representing a global ECG signal obtained from the paced heart of a pig and a filtered signal version useful for PACE detection.
Figure 22:
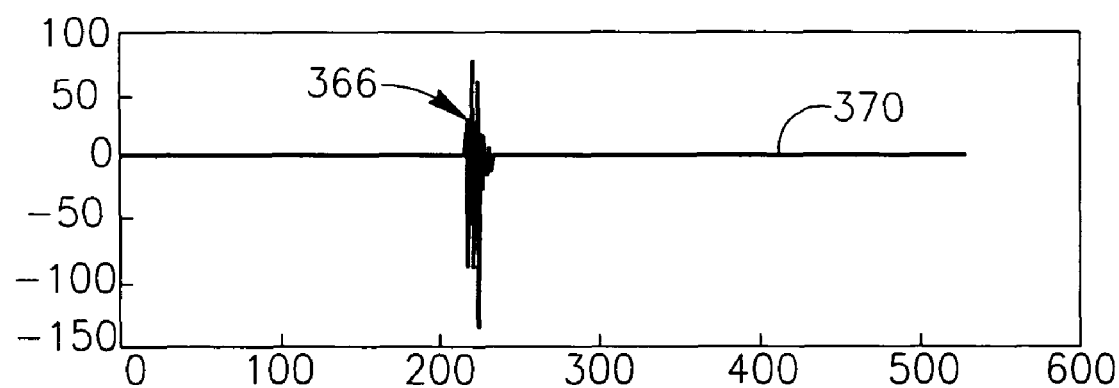

Reference is now made to FIG. 22 which is a schematic graph illustrating exemplary non-filtered and filtered digitized data representing a global ECG signal obtained from the paced heart of a pig and a filtered signal version useful for PACE detection. The curve 360 represents the signal recorded from a global ECG channel. The waveform 364 represents the ECG complex and the waveform 362 represents the pacing artifact.

The curve 380 represents the signal represented by curve 360 after filtration using high pass filter parameters which strongly attenuate the low frequency components of the ECG complex while preserving the high frequency components of the pacing induced artifact. The filtered signal 370 is useful for the pace detection algorithms of the present invention.

Figure 23:
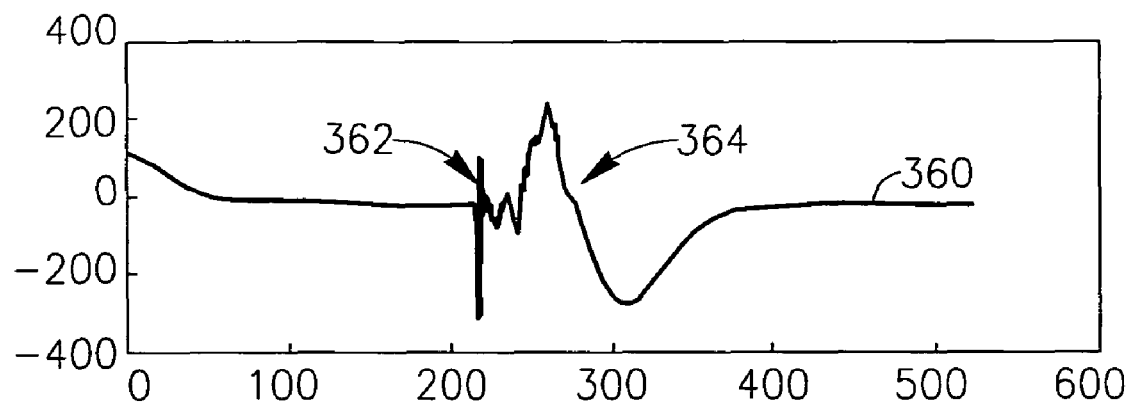
FIG. 23 is a schematic graph illustrating exemplary non-filtered digitized data representing a global ECG signal obtained from the paced heart of a pig and a filtered signal useful for computing a template.
Figure 23:
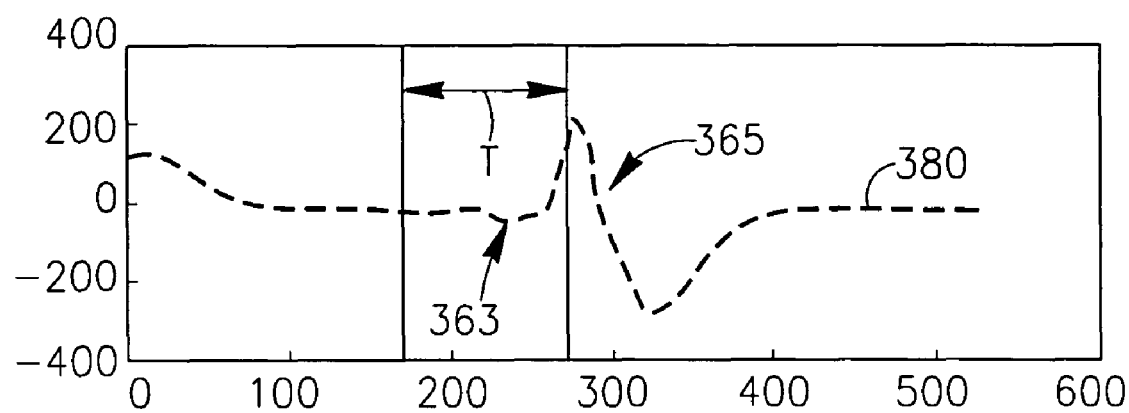

Reference is now made to FIG. 23 which is a schematic graph illustrating the same non-filtered digitized data representing a global ECG signal illustrated in FIG. 22 and another filtered signal (using different filtration parameters) useful for computing a template, in accordance with an embodiment of the present invention.

The signal curve 360 is identical to the curve 360 of FIG. 22. The curve 38 represents a filtered signal form filtered using low pass filtration parameters. It is noted that in the curve 380, the filtered Pacing artifact 363 is highly attenuated as compared to the pacing artifact 362 of the non-filtered signal curve 360. The filtered ECG complex 365 may be thus be conveniently used for constructing the ECG template as disclosed in detail hereinabove. The double headed arrow labeled T represents the approximate time duration of the ECG template typically used in the method of the present invention. It is noted that the early part of the ECG complex signal is used and is adequate for obtaining good template enabling satisfactory detection of normal beats eligible for CCM delivery at quite an early time within the beat. However, template time periods having different duration and temporal position than the exemplary period T of FIG. 23 may also be used in accordance with other embodiments of the present invention.

Figure 24:
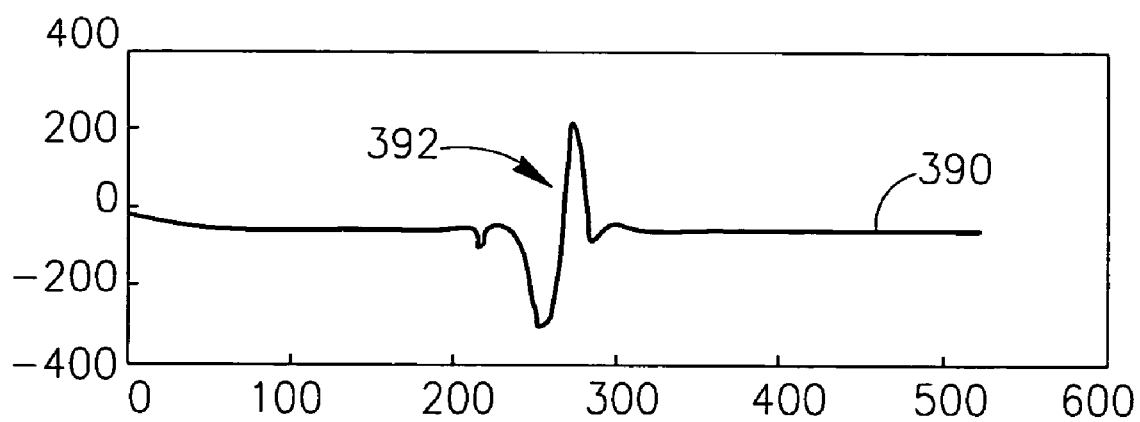
FIG. 24 is a schematic graph illustrating an example of non-filtered digitized signal data from a ventricular local sense channel (VS) in the heart of a pig, and a filtered version of the signal useful for beat threshold crossing detection.
Figure 24:
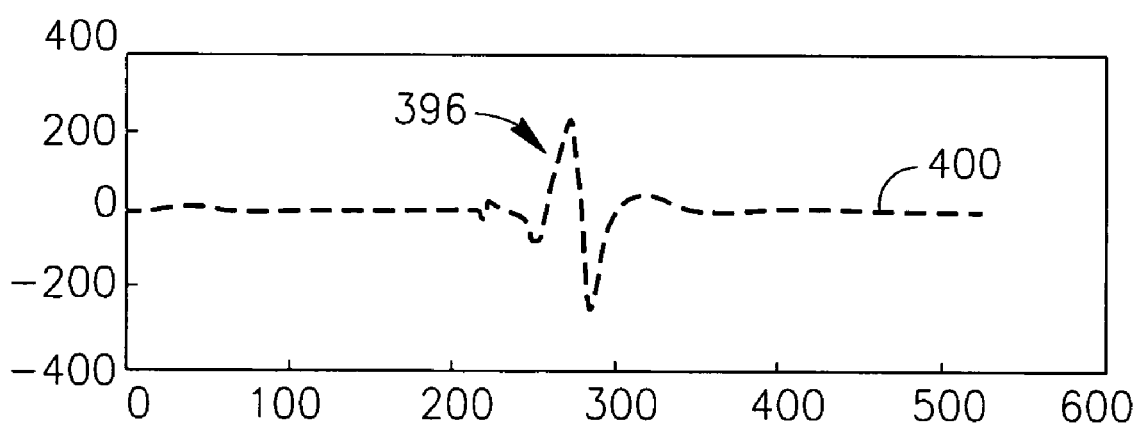

Reference is now made to FIG. 24 which is a schematic graph illustrating an example of non-filtered digitized data from a ventricular local sense channel (VS), recorded simultaneously in the pigs heart together with the signals represented by the curve 360 of FIGS. 22 and 23, and a filtered version of the signal useful for beat threshold crossing detection. The curve 390 represents the local ventricular channel SV recorded and the waveform 392 represents a SENSE electrical event representing the ventricular sensed excitation wave. The curve 400 represents a filtered version of the VS signal of curve 390 which is useful for performing the SENSE beat single threshold crossing criterion or test as disclosed hereinabove in detail in an embodiment of the method of the present invention.

Figure 25:
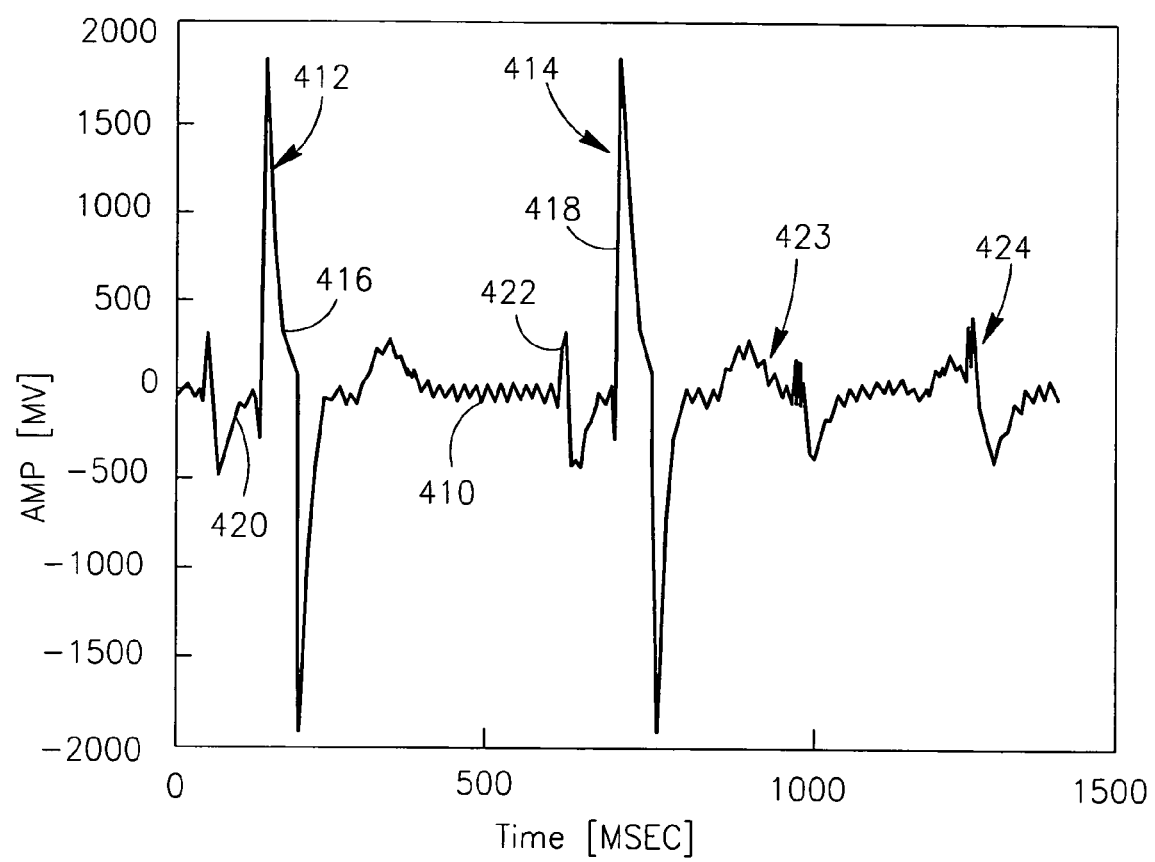
FIG. 25 is a schematic graph illustrating an example of a digitized data signal representing a global ECG signal obtained from the heart of a pig and including normal beats and PVCs.

Reference is now made to FIG. 25 which is a schematic graph illustrating an example of a digitized data signal representing a global ECG signal obtained from the heart of a pig and including normal beats and PVCs. The curve 410 represents the global recorded ECG signal. The waveforms 412 and 414 represent normal beat ECG signals and the waveforms 423 and 424 represent PVCs. In each of the normal beat waveforms 412 and 414 one can observe the switching artifacts 416 and 418, respectively, associated with the delivering of a CCM signal to the pigs ventricle. The switching artifacts 416 and 418 are superimposed on the ECG waveforms 420 and 422 of the two normal beats, respectively (which do not represent the true form of the CCM signal). The CCM device detected the two waveforms 423 and 424 as abnormal and therefore did not enable the delivering of CCM signals during the abnormal beat forms 422 and 424, which are visually identifiable as premature ventricular contractions.

Figure 26:
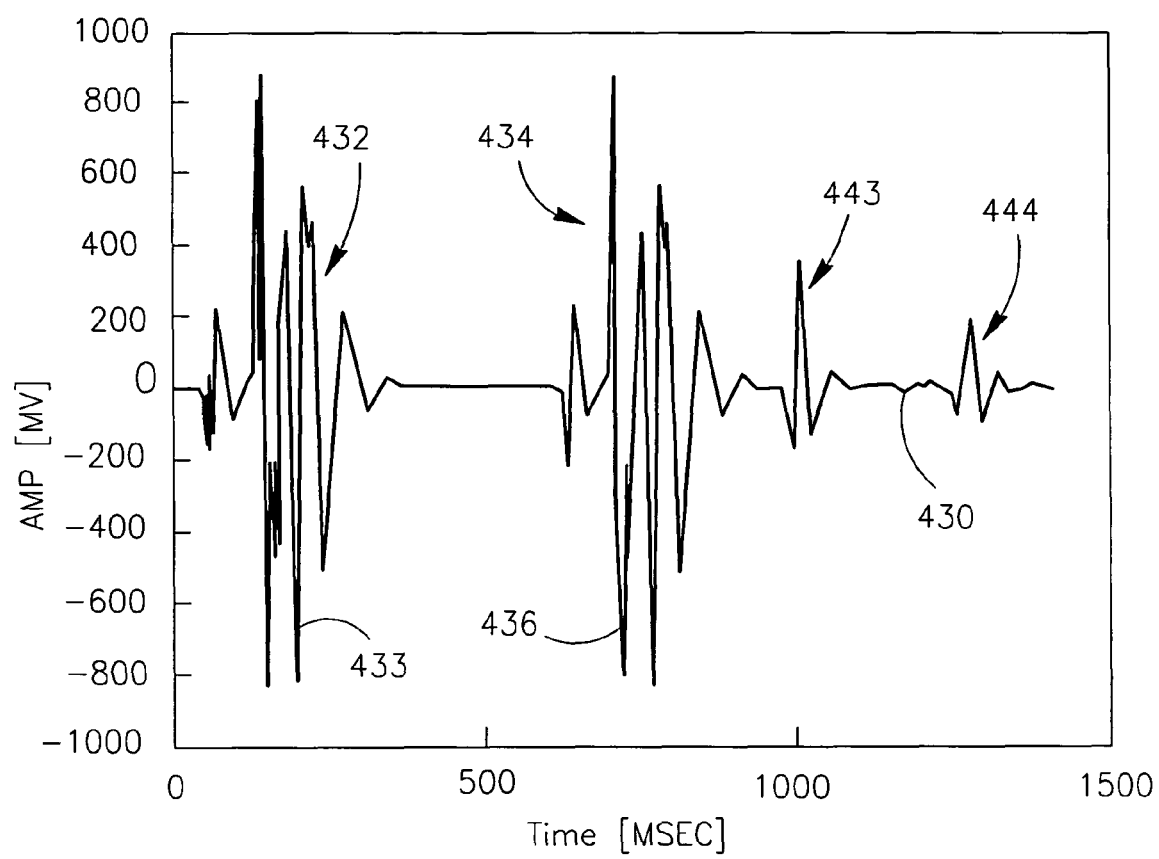
FIG. 26 is a schematic graph illustrating an example of a digitized data signal representing the ventricular local sense signal recorded simultaneously with the global ECG signal illustrated in FIG. 25.

Reference is now made to FIG. 26 which is a schematic graph illustrating an example of a digitized data signal representing the ventricular local sense signal recorded simultaneously with the global ECG signal illustrated in FIG. 25. The curve 430 represents the ventricular local sense signal recorded simultaneously with the ECG signal of curve 410 (FIG. 25). The waveforms 432 and 434 represent the locally sensed ventricular recorded normal beats including the CCM switching artifacts 433 and 436, respectively. The waveforms 443 and 444 represent the sensed PVCs which were detected as abnormal beats and are therefore without CCM induced artifacts as no CCM signals were delivered.

Figure 27:
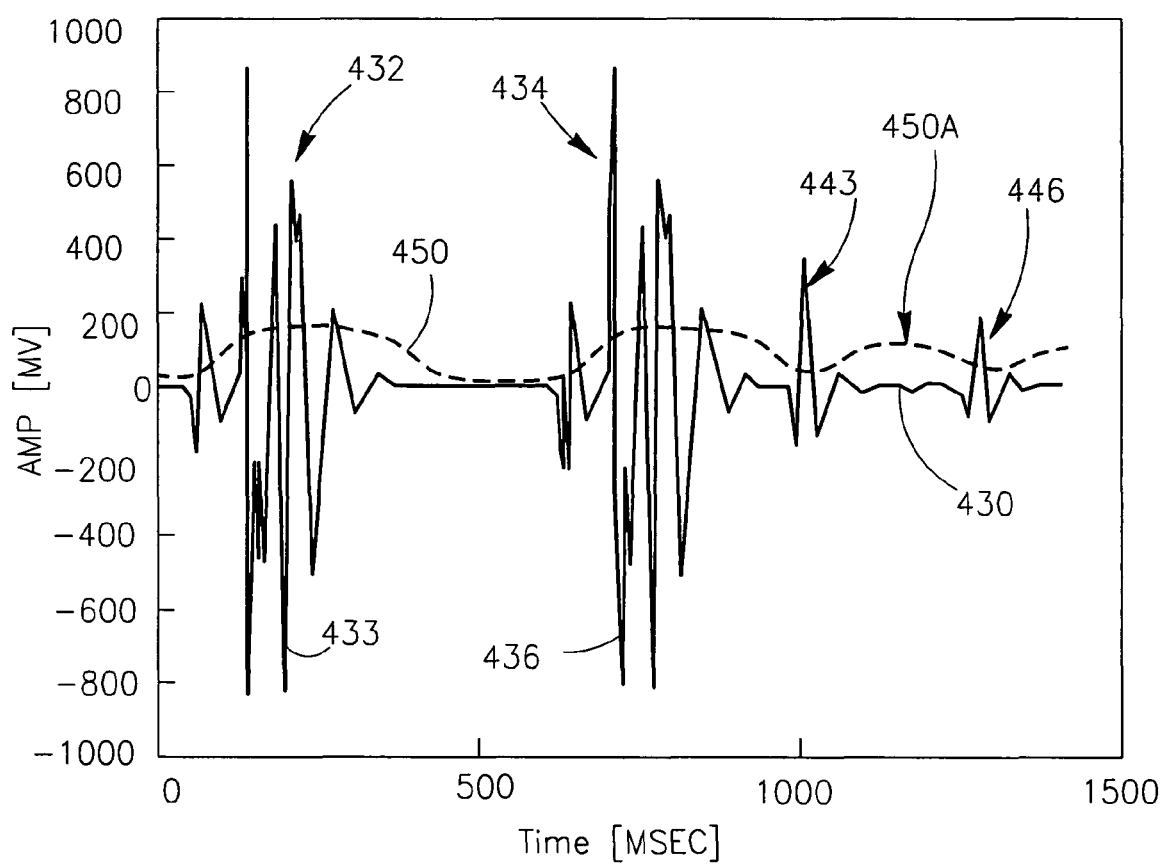
FIG. 27 is a schematic graph illustrating the same ventricular local sense signal (VS) of FIG. 26 and also a recording of the left ventricular pressure as measured in the left ventricle of the same pig.

Reference is now made to FIG. 27 which is a schematic graph illustrating the same ventricular local sense signal (VS) of FIG. 26 and also a recording of the left ventricular pressure as measured in the left ventricle of the same pig. The dashed curve 430 represents the left ventricular pressure LVP (arbitrary scale) as simultaneously measured in the left ventricle of the same pig. As is known in the art, the LVP is a good indicator for PVCs. As may be seen, the part 450A of the LVP curve 450 which is near the time of occurrence of the PVCs 443 and 446 has an abnormal shape and amplitude.

Figure 28:
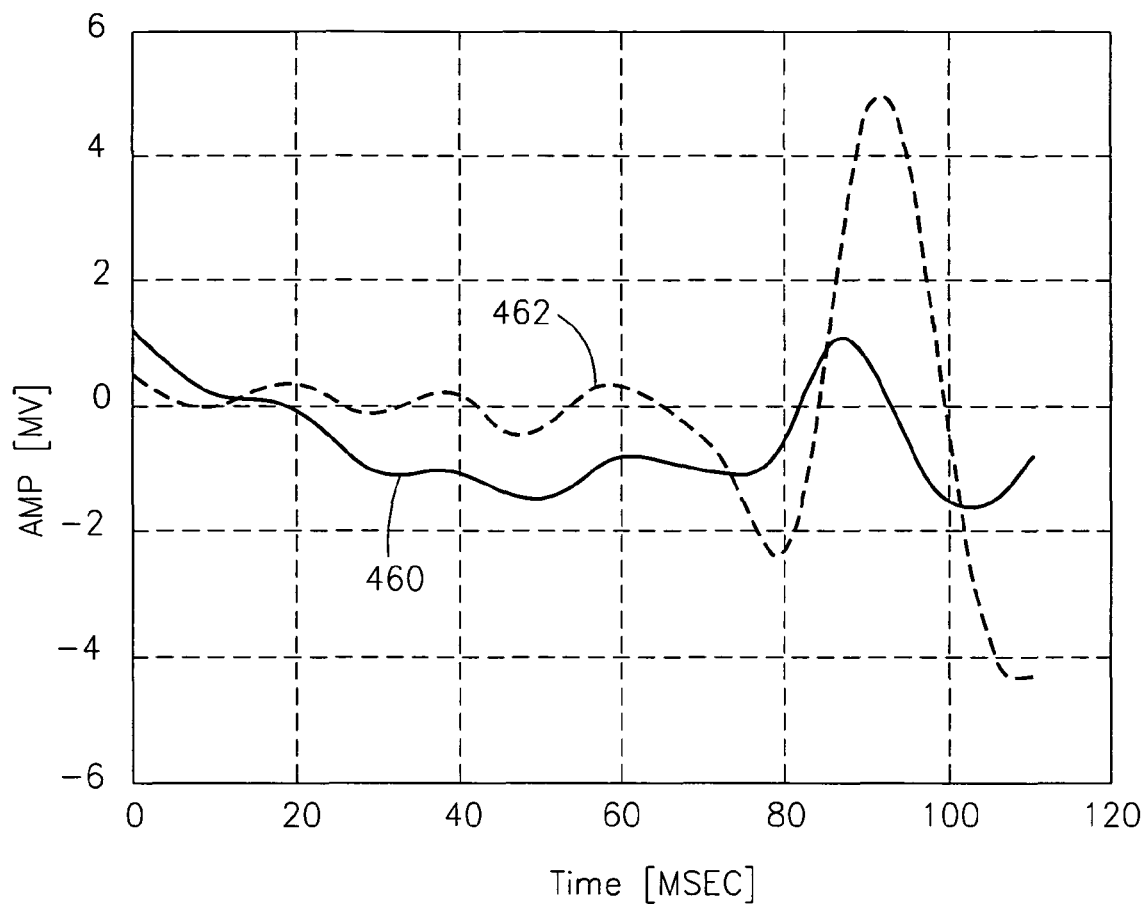
FIGS. 28-29 are schematic graphs illustrating an experimental sample of an ECG template (computed for a pig's heart in accordance with an adaptive template method of the present invention) and two different single recorded ECG signals from different cardiac beats compared with the template.
Figure 29:
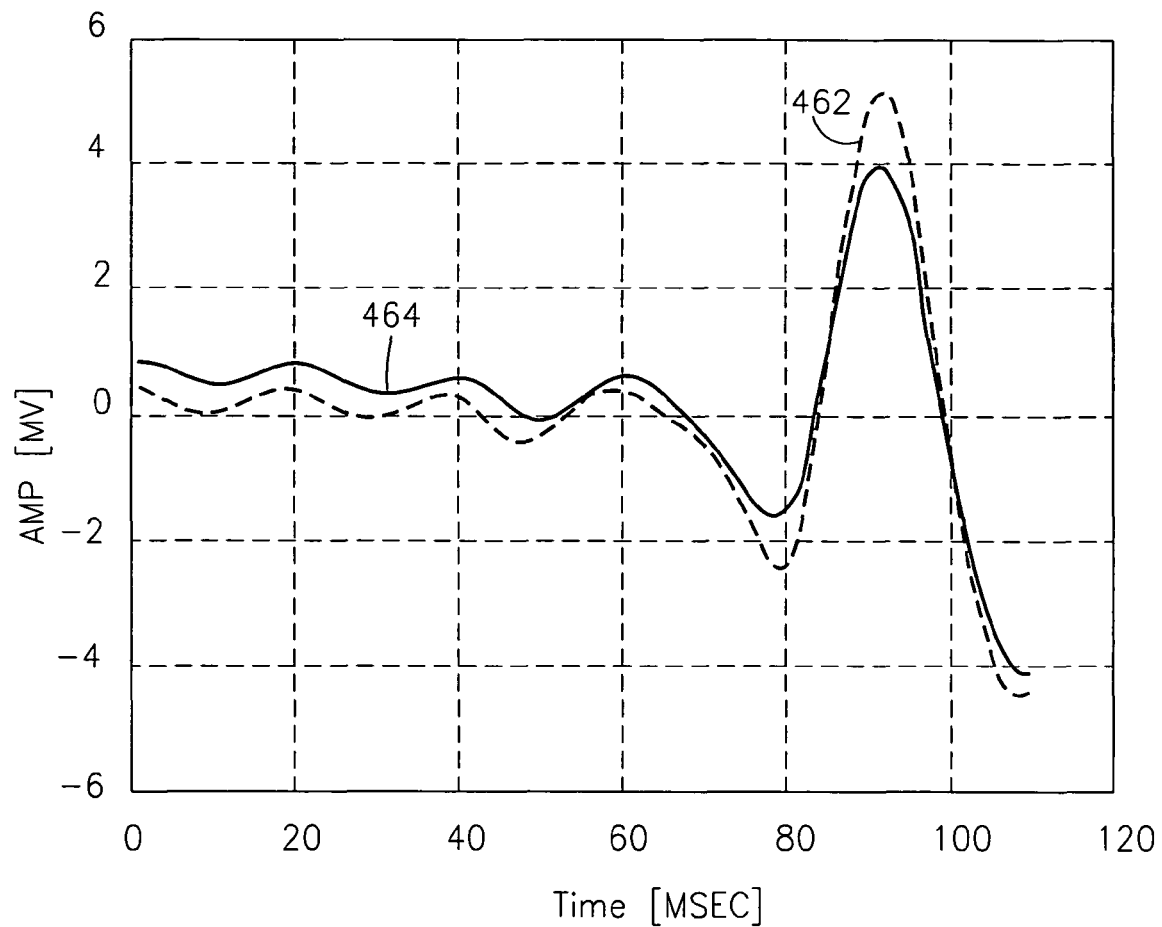

Reference is now made to FIGS. 28-29 which are schematic graphs illustrating an experimental sample of an ECG template (computed for a pig's heart in accordance with an adaptive template method of the present invention) and two different single recorded ECG signals from different cardiac beats compared with the template. In FIG. 28, the dashed curve 462 represents the ECG template generated based on averaged ECG data from multiple ECG signals recorded in multiple beats collected in the experiment. The curve 460 represents part of the ECG signal of a single ECG waveform recorded in a single beat from the same experiment. The computation of the template matching of the signal shown as curve 460 did not pass the template matching criterion and failed the test (and no CCM signal was delivered in the beat. In FIG. 29, the template curve 462 is illustrated with another different curve 464 representing part of the ECG signal of another different single ECG waveform recorded in a different single beat from the same experiment. The computation of the template matching of the signal shown as curve 464 passed the template matching test criterion successfully, and a CCM signal was delivered in the beat. It is noted that the CCM signal artifacts are not shown in FIG. 29 as the CCM signal is delivered at a later time point not included within the scale of the graph.

Figure 30:
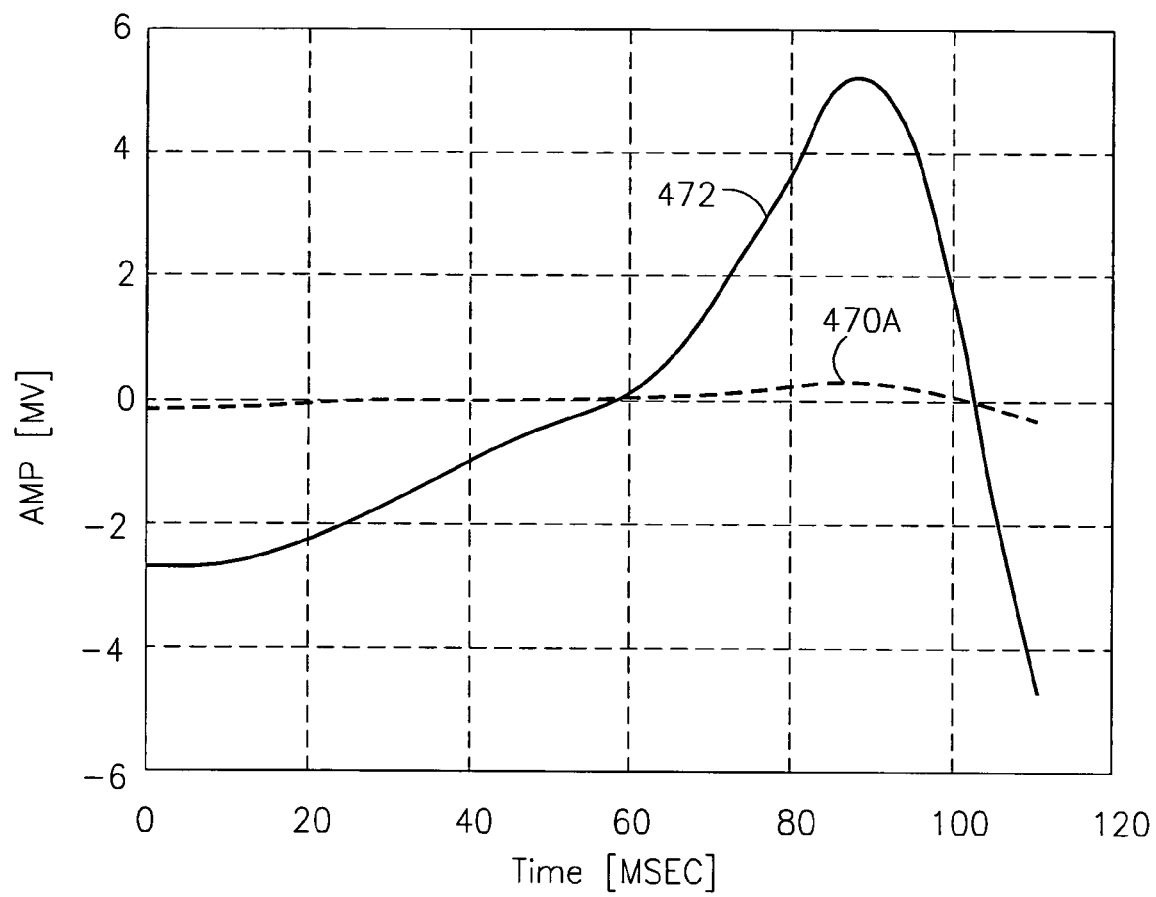
FIGS. 30-32 are schematic diagrams illustrating the gradual build up of the shape of an ECG channel template (computed for signals recorded from a pig, at three discrete times during the computation of the adaptive ECG template.
Figure 31:
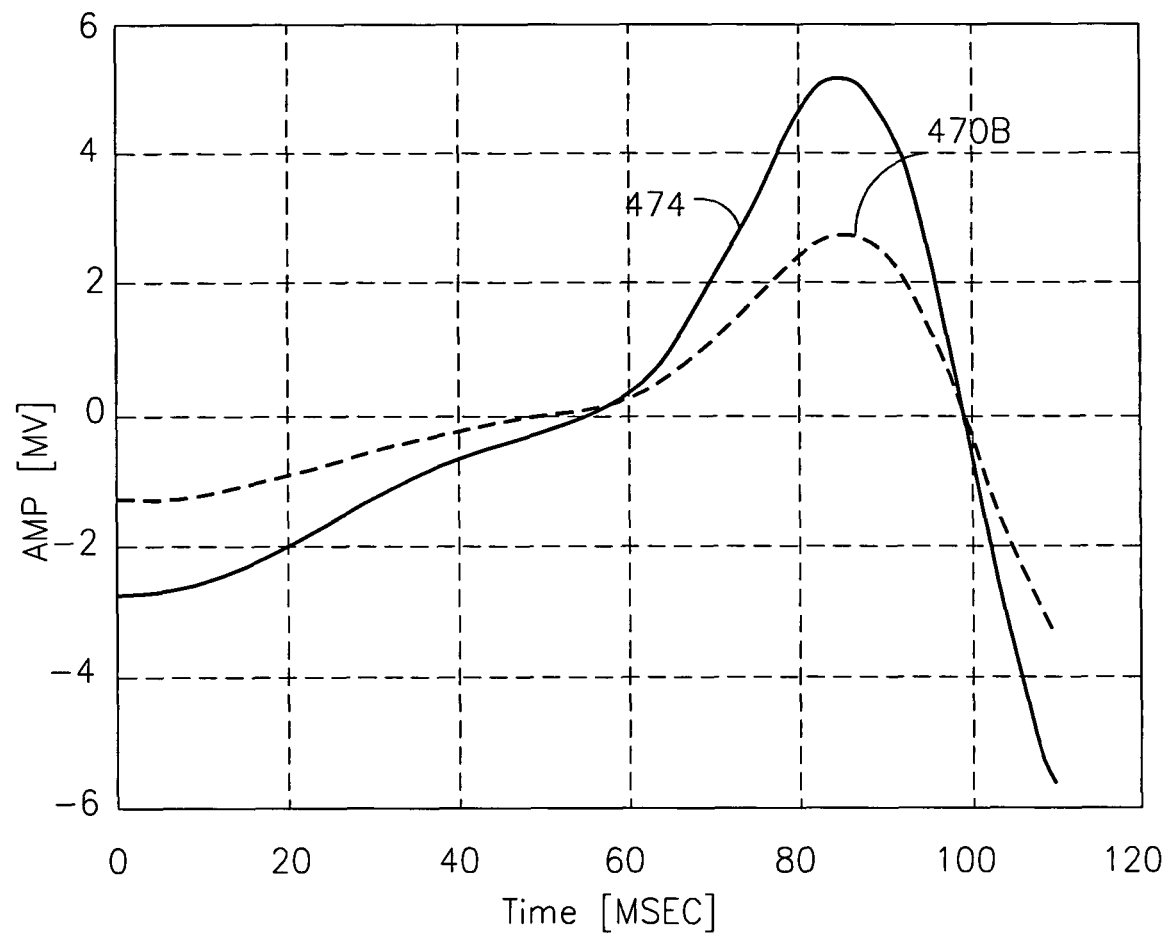
Figure 32:
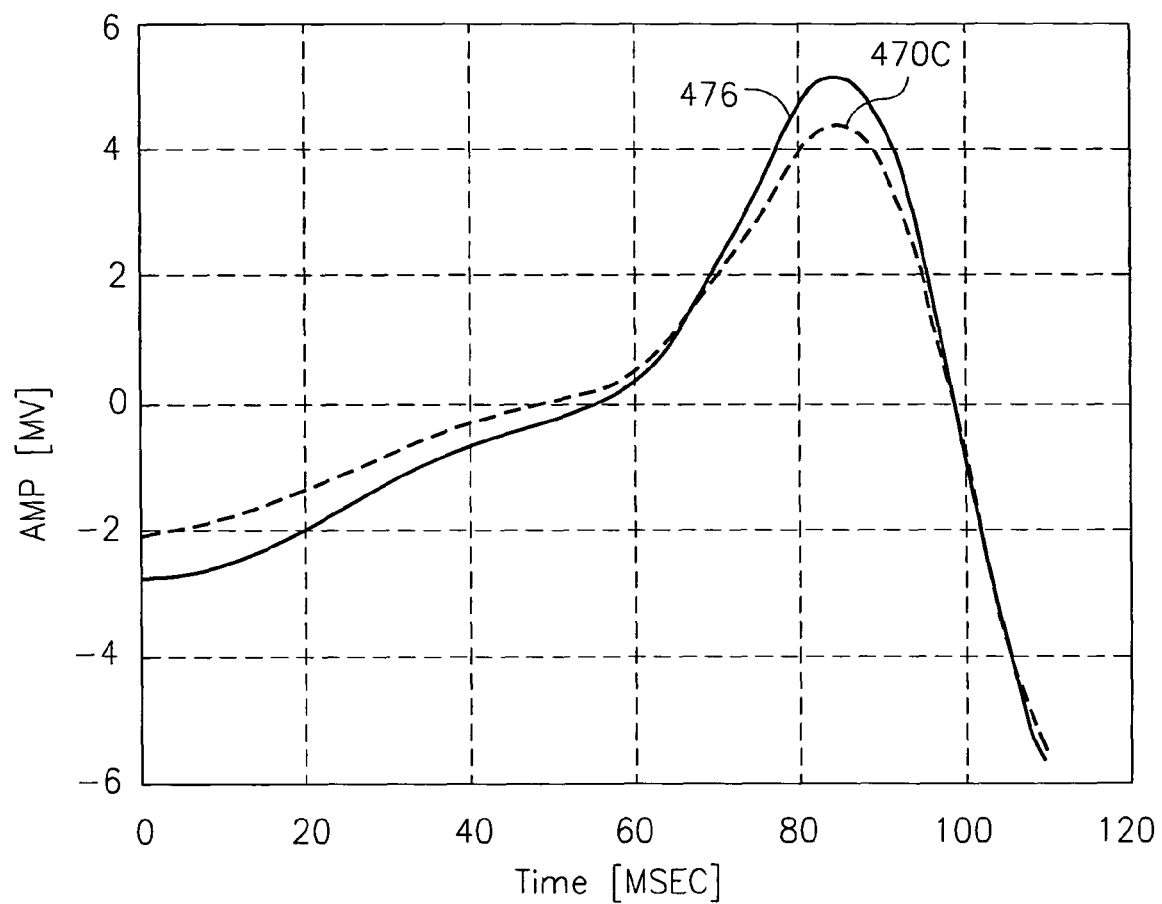

Reference is now made to FIGS. 30-32 which are schematic diagrams illustrating the gradual build-up of the shape of an ECG channel template (computed for signals recorded from a pig, at three discrete times during the computation of the adaptive ECG template. In FIG. 30, the dashed curve 470A represent the initial adaptive ECG template curve accumulated at the beginning of recording and the curve 472 represent the shape of the ECG signal recorded in the ECG buffer in the current beat. The template 470A is fairly flat and does not have good resemblance to the shape of a single beat as not enough beat samples have been averaged in the current template form.

In FIG. 31, the dashed curve 470B represent the adaptive ECG template curve accumulated at a time in the recording later than the time shown in FIG. 30. The curve 474 represent the shape of the ECG signal recorded in the ECG buffer in the current beat (and is different than the curve 472 of FIG. 30). The template 470B is in an intermediate form with higher resemblance to the shape of a single beat as more beat samples (of "good" beats passing the tests) have been averaged in the current template form.

In FIG. 32, the dashed curve 470C represent the adaptive ECG template curve accumulated at a time in the recording later than the time shown in FIG. 31. The curve 476 represent the shape of the ECG signal recorded in the ECG buffer in the current beat (and is different than the curves 472 and 474 of FIGS. 30 and 31, respectively). The template 470C is in a form with even higher resemblance to the shape of a single beat as an even larger number of good beat samples has been averaged in the template form.

Figure 33:
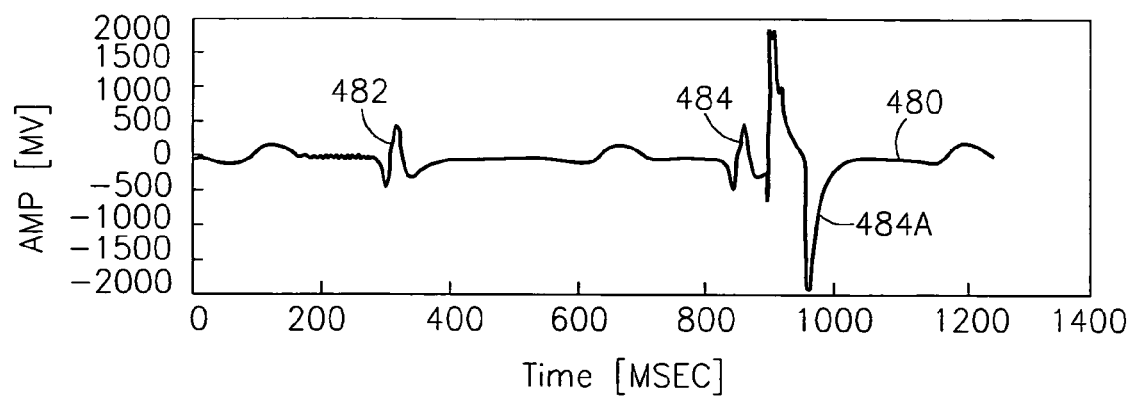
FIGS. 33-34 are schematic diagrams illustrating ventricular local sense signals and global ECG signals simultaneously recorded in non-paced heart of a pig, and the corresponding filtered forms of the signals.
Figure 33:
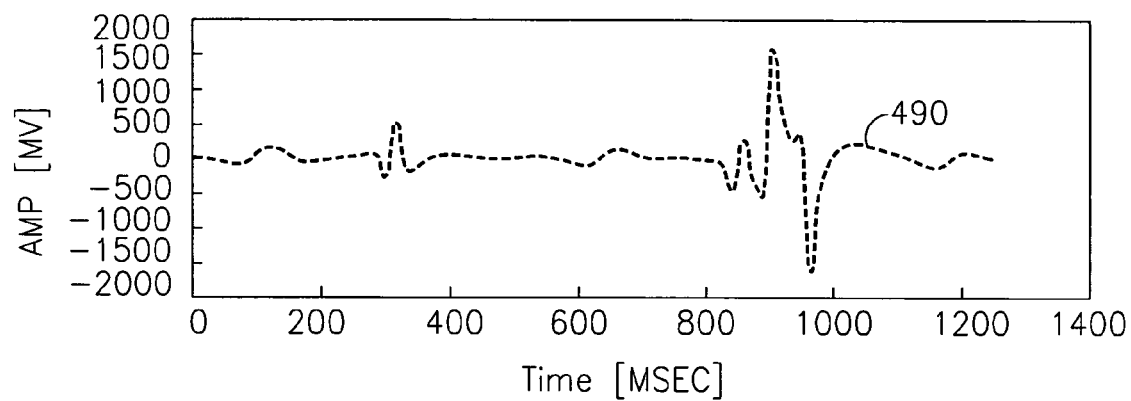
Figure 34:
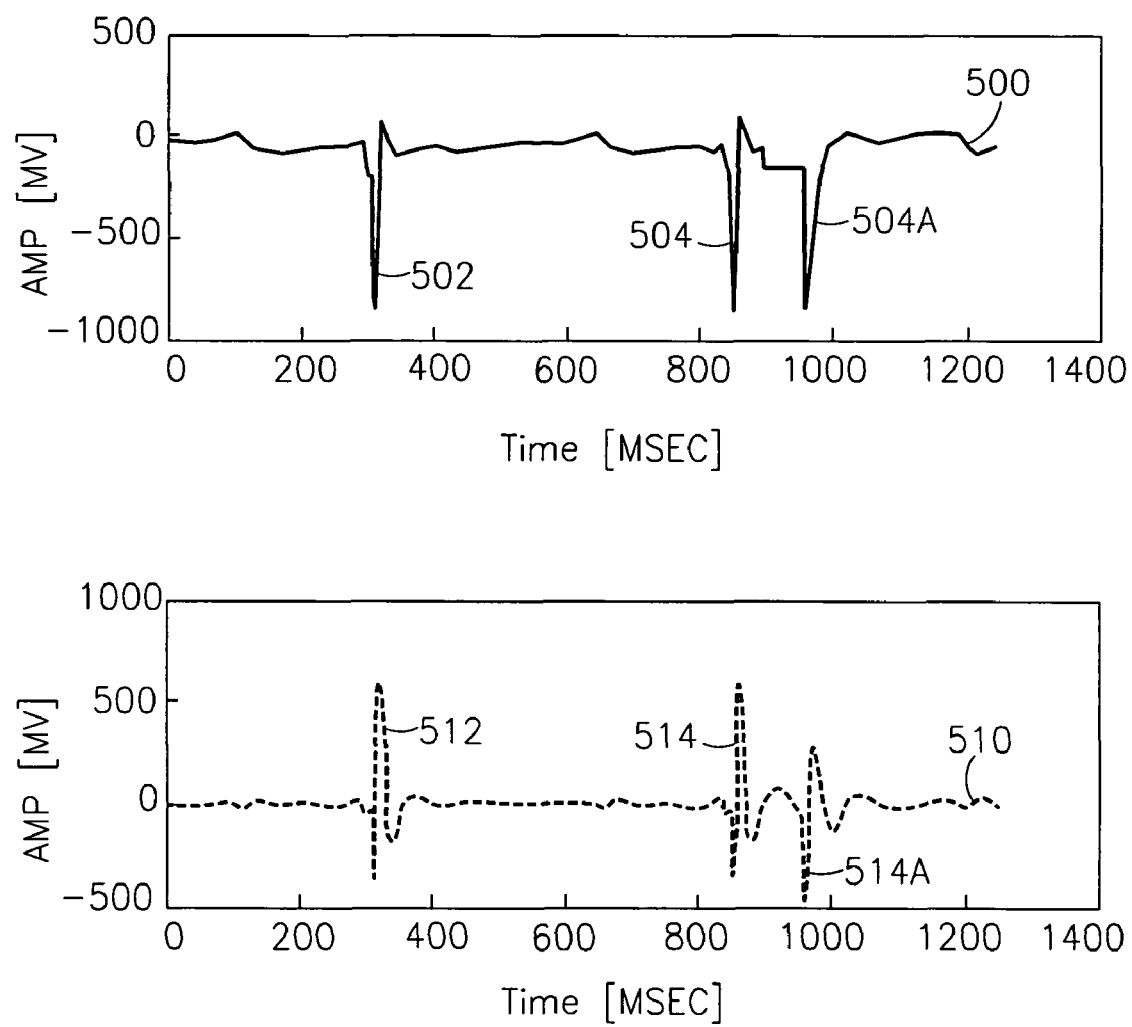

Reference is now made to FIGS. 33-34 which are schematic diagrams illustrating ventricular local sense signals and ECG signals simultaneously recorded in non-paced heart of a pig, and the corresponding filtered forms of the signals.

In FIG. 33, the curve 480 represents the non-filtered signal of the global ECG signal recorded in a non-paced pig's heart. The waveform 482 represents the ECG complex of a beat in which a CCM signal was not delivered to the heart. The waveform 484 represents part of the ECG complex of a beat in which a CCM signal was delivered to the heart. The waveform 484A represents the CCM associated switching artifacts. The curve 490 of FIG. 33 represents the simultaneous signal of the filtered form of the signal of the curve 480.

In FIG. 34 the curve 500 represents the non-filtered signal of the locally sense ventricular signal recorded simultaneously with the global ECG signal of curve 480 (of FIG. 33) in the same pig's heart. The waveform 502 represents the ventricular local SENSE signal of a beat in which a CCM signal was not delivered to the heart. The waveform 504 represents part of the Local SENSE signal of the beat in which a CCM signal was delivered to the heart. The waveform 504A represents the CCM associated switching artifacts. The curve 510 of FIG. 34 represents the signal of the filtered form of the signal of the curve 500. The waveform 512 represents the filtered local sense complex in the beat in which no CCM signal was delivered to the heart and the waveform 514 represents the filtered local sense complex in the beat in which a CCM signal was delivered to the heart. The waveform 514A represents part of the filtered CCM associated switching artifact.

It is noted that while the devices and systems disclosed herein may receive a signal from an internal pacemaker circuit integrated in or included within the CCM delivery device as disclosed hereinabove (pacemaker not shown for the sake of clarity of illustration), It is also possible to provide embodiments that may be capable of receiving a wired or a wirelessly transmitted signal from a separate additional pacemaker device simultaneously implanted within the same patient having an implanted CCM delivery device. Such a transmitted pace indicating signal, may be communicated between the two devices using suitable remote wireless transmitters and/or receivers and or transceivers, as is known in the art. Thus embodiments of the CCM devices of the present invention which include suitable telemetry devices for receiving external signals indicating pacing of the heart are included within the scope of the present invention.

Additionally or alternatively, the CCM devices and systems of the present invention may be configured into embodiments which may use signals providing other different information types from other devices implanted in the same patient. For example, if there is a defibrillator or an IECD or a combined defibrillator/pacemaker device (or any other cardiac therapeutic device known in the art) implanted in the same patient with the CCM delivering device, the CCM device may be configured to receive various signals from the defibrillator or other device which may provide the CCM device with information usable by the CCM device. Among such useful signals may be included signals providing information about the occurrence and/or timing, and/or magnitude of events such as, electrical noise generating events (such as, for example, defibrillating shocks to be delivered to the patient by a defibrillator circuit, signals reporting and or containing additional information about cardiac events including but not limited to detection of an arrhythmia in the heart, detection of tachycardia, detection of ventricular fibrillation, and the like.

Information which may additionally or alternatively be transmitted (in a wired configuration or wirelessly) to the CCM devices of the present invention may include any signals associated with information about any malfunction of a circuit or electrical part of the device(s) or short circuit or an electrical break in a circuit, or the like.

The receiving of any of the above disclosed signals from other devices (whether separate devices independently implanted in the same patient, or such devices integrated with or formed as a part of the CCM devices and systems of the present invention) may be advantageously used by the CCM devices to improve the control of CCM signal delivery to the heart. For example, if a defibrillator device detected an arrhythmia in the heart, the detection signal if transferred to the CCM device may be used to inhibit the delivery of CCM signals to improve patient safety. Similarly, any of the signals indicating the development an undesired or potentially hazardous cardiac condition or a malfunction of part of a device, may be used by the CCM device to inhibit the delivery of CCM signals to the patient.

Thus, the scope of the present invention is also intended to cover CCM devices and systems having communication means or communication units (including wired, wireless, remote, unidirectional or bidirectional communication devices) for receiving any data from another cardiac associated therapeutic or monitoring device implanted in or disposed on the same patient, and CCM devices configured to make use of such data transmitted or communicated from other devices, which data includes useful information relevant to CCM signal delivery decisions and control, in order to control, modify or disable one or more aspects of the delivering of CCM signals to the heart of a patient based on the received signal.

It is further noted that the idea of having a safe signal delivery system to the ventricle may be useful for various kinds of cardiac treatments (e.g. pacing, Bi-Ventricular pacing and the like) that may have to be applied in the presence of atrial fibrillation or atrial flutter. In such conditions the atrial sensing may not be informative enough, and knowing the condition of the ventricle may require additional analysis of ventricular activity in a form similar to the form presented in the present invention.

Thus, the method of the present invention of basing a decision to inhibit electrical therapy on locally sensed signals may be applied to other therapies and is not limited to therapeutic non-excitatory signals like CCM signals). The methods of sensing, detection and decision of the present invention may be easily and advantageously adapted for use in defibrillation/cardioversion therapy, chamber overdrive by pacing for anti-tachycardia, and other types of electrotherapy. This may be particularly advantageous for BIV pacing since BIV pacing uses the activity in one cardiac chamber to immediately initiate activity in another cardiac chamber, while having no (or very limited) sensing capabilities for activity in the left chamber. Thus, the methods of sensing, analysis and decision of the present invention may be used to effectively apply BIV pacing to a heart without the need for performing atrial sensing and therefore without the need for an implanted atrial lead). Such methods may enable the performing of BIV pacing in the presence of atrial fibrillation.

While there exist systems that analyze ventricular activity to detect fibrillation, PVCs etc, those systems take the decisions over multiple beats, after analyzing the entire ECG pattern. The methods of the present invention are used to make a real-time decision in the early phase of the current beat, thus smart analysis combining local and global sensing is required.

Figure 35:
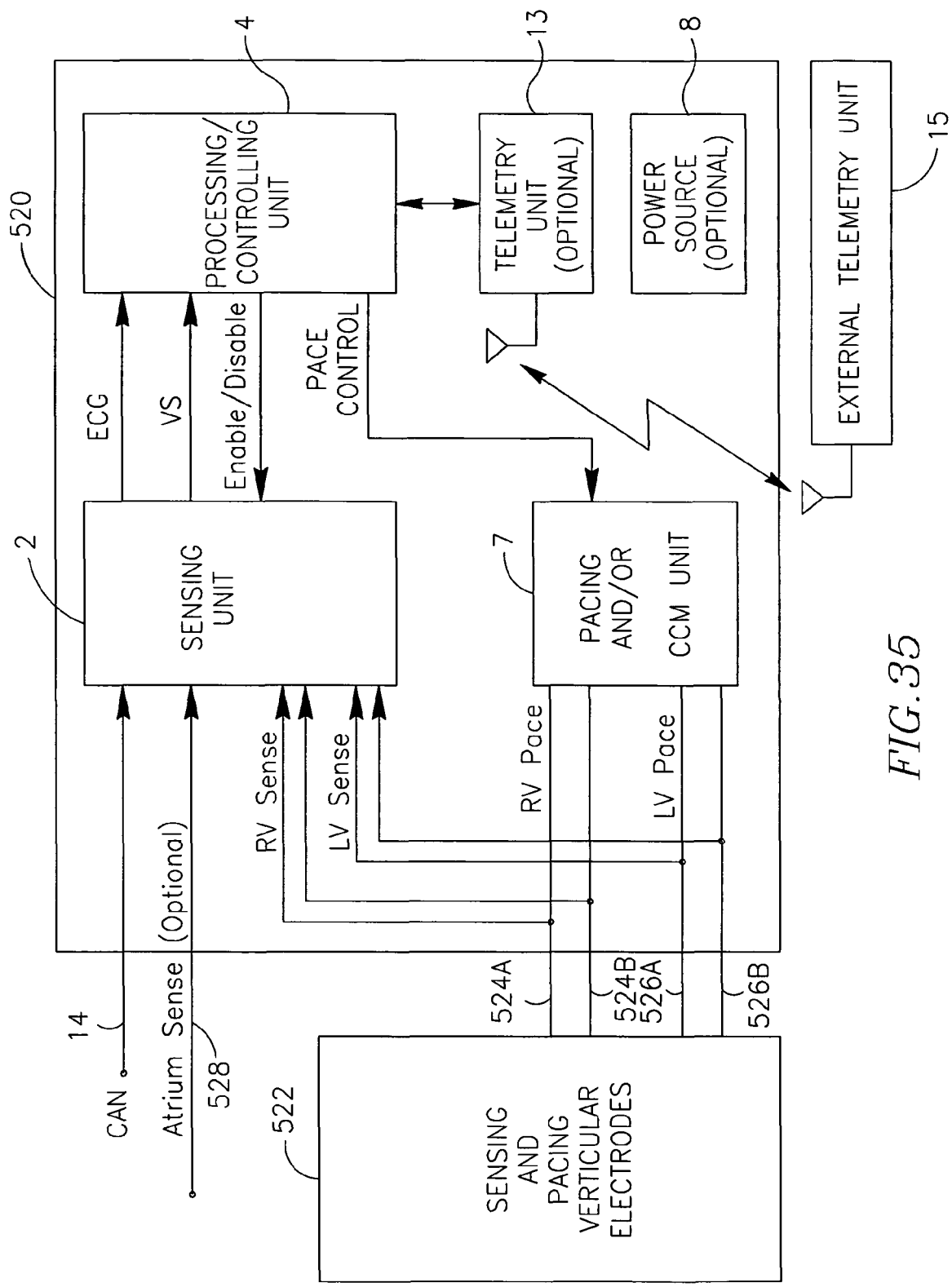
FIG. 35 is a schematic functional block diagram illustrating a pacing device adapted for using two pairs of ventricular sensing electrodes for sensing cardiac events and for controlling the delivering of biventricular pacing signals to the ventricle(s) based on information obtained from the two pairs of ventricular sensing electrodes and a can electrode, in accordance with another embodiment of the present invention.

Reference is now made to FIG. 35 which is a schematic functional block diagram illustrating a pacing device adapted for using two pairs of ventricular sensing electrodes for sensing cardiac events and for controlling the delivering of biventricular pacing signals to the ventricle(s) based on information obtained from the two pairs of ventricular sensing electrodes and a can electrode, in accordance with another embodiment of the present invention.

The pacing device 520 includes the sensing unit 2, the processing/controlling unit 4 and the power source 8 as described in detail with respect to the device 20A (of FIG. 4). The pacing device 520 also includes a pacing/CCM unit 7. The pacing/CCM unit 7 may be any pacing unit configured for providing biventricular pacing to the heart as is known in the art.

However, in accordance with another embodiment of the invention, the pacing/CCM unit 7 may be a dual-purpose unit that includes circuitry configured for providing biventricular pacing to the heart and also configured for providing CCM signals for modifying the contractility of one or more cardiac chamber, as is known in the art and as disclosed hereinabove and as illustrated in any of FIGS. 1, 2 and 4. In this case, the pacing/CCM unit 7 may in operation provide biventricular pacing as well as deliver CCM signals to one or more cardiac chambers when the cardiact conditions require such biventricular pacing and/or CCM therapy.

In the specific and non-limiting configuration illustrated in FIG. 35, the pacing/CCM unit 7 includes both biventricular pacing capabilities and CCM signal delivery capabilities. The pacing/CCM unit 7 is suitably coupled to ventricular electrodes 522. A first pair of bipolar right ventricular (RV) electrodes 524A and 524B, are used to deliver pacing signals to the right ventricle. A second pair of bipolar left ventricular (LV) electrodes 526A and 526B are used to deliver pacing signals to the left ventricle. The Electrodes 524A, 524B, 526A and 526B are also suitably coupled to the sensing unit 2 for providing local sensing (LS) capabilities in the left and right ventricles. As is typical in many biventricular pacing devices known in the art, the sensing unit 2 may also be (optionally) coupled to an atrial sensing electrode 528 disposed in an atrium of the heart (preferably but not obligatorily, in the right atrium). The atrium electrode 528 may provide useful information about atrial electrical activity, as is known in the art. It is noted that while the atrium electrode 528 is illustrated as configured for unipolar sensing of the atrium, it is also possible to have an additional atrial electrode (not shown in FIG. 35) for performing bipolar sensing, as is known in the art. It will be appreciated by those skilled in the art that any other electrode combinations and/or configurations known in the art for performing atrial sensing may also be used in the device 520 of the present invention.

The device 520 may also (optionally, but not obligatorily) include a telemetry unit 13 suitably coupled to the processing/controlling unit 4 for communicating data and/or command signals and/or programming signals to and from the processing/controlling unit 4. The telemetry unit 13 may (wirelessly) communicate with an external telemetry unit 15 as is known in the art to transmit to, and/or receive from the external telemetry unit 15 data and/or command signals and/or programming signals for sending data to the external telemetry unit 15 and/or for receiving suitable command signals for controlling and/or programming the operation of the processing/controlling unit 4. It is noted that as is the case with all the processing/controlling units of any of the devices disclosed herein, the processing/controlling unit 4 may include memory storage circuitry and/or storage devices (not shown in detail) for storing data and also means for communicating the data between the memory and/or storage units and the processing controlling unit 4.

The pacing/CCM unit 7 is suitably coupled to the processing/controlling unit 4 for receiving pacing control signals therefrom. In operation, the pacing device 520 may provide biventricular pacing signals to the cardiac ventricles, as is known in the art. However, in contrast to prior art biventricular pacing devices that will not deliver biventricular pacing in the presence of atrial fibrillation and/or atrial flutter and/or other supra-ventricular arrhythmic electrical activity, the device 520 of the present invention is capable of delivering biventricular pacing in the presence of atrial fibrillation and/or paroxysmal atrial fibrillation and/or atrial flutter and/or other supra-ventricular arrhythmic electrical activity by using the combination of the local ventricular sensing in the ventricles together with the global signal recording (such as, but not limited to the ECG recording against the can electrode 14 and/or an ECG signal obtained by using external electrodes applied to the patient's body as disclosed in detail hereinabove for the devices 20, 20A and 30 of FIGS. 1, 2 and 4, respectively). The same type of methods, algorithms and decision strategies (with the same or similar tests, acceptability criteria and templates) described hereinabove with respect to deciding if a suspected event (such as, for example, an ectopic beat and/or a PVC, and/or another arrhythmic event) has been detected in order to make a decision of whether or not to enable the delivery of a CCM signal may be also applied and used in operating the biventricular pacing of the device 520 for making a decision of whether or not to deliver biventricular pacing signals to the cardiac ventricles.

Thus, when the pacing/CCM unit 7 of the device 520 is configured to be a pacing unit only (without CCM signal delivering capability), the device 520 is a novel biventricular pacing device with improved biventricular pacing capabilities as it is capable to efficiently deliver biventricular pacing to the heart even in the presence of atrial fibrillation and/or paroxysmal atrial fibrillation and/or atrial flutter and/or other supra-ventricular arrhythmic electrical activity that would have caused a conventional prior art biventricular pacing device to disadvantageously disable the delivery of such biventricular pacing signals.

Similarly, when the Pacing/CCM unit 7 is configured for delivering biventricular pacing as well as CCM signals, the device 520 may be able to use the same type of methods, algorithms and decision strategies (with the same tests, acceptability criteria and templates) described hereinabove for determining whether a suspected ectopic event and/or PVC and/or an arrhythmic event has occurred and to use the results of this determination to enable or disable the delivery of biventricular pacing signals and the delivery of CCM signal(s), (if required by cardiac conditions).

Thus, in both of the cases described hereinabove (Pacemaker only and Pacemaker+CCM), the decision to deliver the biventricular pacing signals and/or CCM signal(s), is taken based on the locally sensed ventricular signals and the globally sensed signals (ECG), irrespective of the electrical activity occurring in the atria. This method of operation of the devices disclosed herein is advantageous, as it makes it possible to operate the devices without atrial sensing and allows the elimination of an atrial lead, simplifying the electrode implantation, and reducing lead size and additional risk to the patient. It is, however noted, that it is also possible to operate the devices with atrial sensing electrode(s), such as, for example the (optional) atrium electrode 528 of the device 520, if it is desired to also receive and/or record additional information about atrial-events for any purpose. In such a case the device 520 simply ignores the sensed atrial signals in making the decision whether to deliver biventricular pacing and/or CCM therapy.

It will be appreciated by those skilled in the art, that the device 520 may be modified to include other types of electrode configurations, as described in detail hereinabove and/or as illustrated in FIGS. 1, 2 and 4.

It is further noted that regarding the electrodes used in the present invention, there may be one or more electrode in the ventricle. There is no requirement that the same electrode(s) will be used for local sensing, global sensing and CCM signal delivery. While in some preferred embodiments of the present invention, the same ventricular electrode(s) are used for ventricular sensing and for CCM signal delivery to the ventricle (s), it may be possible to use separate electrodes or electrode sets to perform the sensing and other electrodes to deliver the CCM signals.

It is further noted that the sensing of the global cardiac activity may be obtained by unipolar recording of an electrode in the ventricle vs. the can electrode, but may also be performed in many other ways as well. For example, the global signal may be recorded multiple implantable electrodes (whether in the heart or outside the heart), or by using body surface electrodes in the case of a non-implantable system (in which the CCM device itself is disposed outside the patient and is suitably coupled to implanted ventricular electrodes.

Similarly, more than one global electrogram signal may be used in the methods and systems of the present invention. For example a 1-12 lead ECG system may be used to analyze various vectors of cardiac electrical activity, and the algorithms may be adapted to combine this information with recorded intra-ventricular signals from suitable ventricular electrodes to control the delivery of CCM signals.

It will be appreciated by those skilled in the art that the CCM devices and systems may include various analog electronic components and/or digital electronic components and/or hybrid analog/digital circuits as is well known in the art. Furthermore, the devices and systems of the present invention may also include any known type of suitable electro-optical, optical, and magneto-optical components, and the like. Any of the programs embedded in the devices of the present invention may be implemented as fully programmable or partially by a user or may be implemented on any known type of memory or storage unit known in the art, including but not limited to, FLASH devices RAM, ROM, EPROM, EEPROM, magnetic memory, or any other suitable type of memory device and/or storage device.

Similarly, the CPU unit(s) and/o the controller/processor units of the present invention may be any known microprocessor, computer, digital signal processor, controller, microcontroller, a programmable or configurable ASIC, or any other suitable processing and/or controlling chip device or element, or combination of several such elements known in the art.

It is noted that the methods and devices described herein may use as the global ECG signal any signal or recording such as an EGG signal (with all ECG electrodes applied externally to the patient's skin, and/or with one or more implanted subcutaneous or otherwise internally implanted electrodes), an Intra-cardiac ECG signal (such as, but not limited to, an Intra-cardiac electrogram, or any electrode arrangement using at least one intra-ventricular electrode and a distant electrode, where the distant electrode may be selected from an external distant electrode, an implanted distant electrode, a can of the CCM device, or any other distant electrode known in the art). Thus, the following types of ECG-like recordings may be included in the term "global ECG" used herein: electrocardiogram (ECG), intra cardiac electrocardiogram (IECG), Intra-cardiac electrogram (IEGM), global electrical activity, far field recorded electrical activity and unipolar recording. All these definitions are regarded as included within the scope of the terms "Global ECG" and/or "global signal" and/or global IECG" and such similar terms used throughout the application.

Similarly, the local sensed signals used in the present invention may be any suitable Near field recording, and/or any suitable form of bipolar recording and any other form of local electrical recording having a limited sensing range and suitable for obtaining ventricular and/or septal recording representing electrical activity in cardiac ventricles.

The invention claimed is:

1. A method for controlling the delivery of a cardiac contractility modulating signal to a heart of a subject within a cardiac beat cycle, the method comprising the steps of:
   applying electrodes to one or more ventricular sites of said heart;
   differentially recording a first non-local intra-cardiac electrocardiogram signal between a first ventricular electrode disposed at a first site of said one or more ventricular sites and a distant electrode implanted in said subject;
   differentially recording a second non-local intra-cardiac electrocardiogram signal between a second ventricular electrode disposed at a second site of said one or more ventricular sites and said distant electrode;
   recording a locally sensed third electrical signal from said first electrode and a locally sensed fourth electrical signal from said second electrode;
   processing said first electrocardiogram signal, said second electrocardiogram signal, said third signal and said fourth signal to detect a suspected ectopic electrical event within said cardiac beat cycle; and
   inhibiting the delivery of a cardiac contractility modulating signal to the heart upon detecting said suspected ectopic electrical event.

2. A method for controlling the delivery of a cardiac contractility modulating signal to a heart of a subject, the method comprising:
   applying one or more ventricular electrodes to one or more ventricular sites of said subject;
   recording at least one non-local electrocardiogram signal of said subject;
   recording at least one locally sensed electrical signal from said one or more ventricular electrode;
   processing said non-local electrocardiogram signal and said at least one locally sensed signal to detect a suspected ectopic electrical event within the current cardiac cycle; and inhibiting the delivery of one or more cardiac contractility modulating signals to the heart upon detecting said suspected ectopic electrical event.

3. The method according to claim 2 wherein said electrocardiogram signal is selected from,
- at least one unipolar intra-cardiac electrocardiogram signal recorded between at least one ventricular electrode disposed at a first site of said one or more ventricular sites and a distant electrode implanted in said subject, and
- at least one electrocardiogram signal recorded using one or more nonimplanted electrodes externally applied to said subject.

4. The method according to claim 2 wherein said current beat cycle is a paced beat cycle and said suspected ectopic electrical event is an ectopic event other than a pacing induced ventricular electrical activity.

5. A device for controlling the delivery of electrotherapeutic signals to a heart of a subject within a cardiac beat cycle, the device comprising:
At least one electrotherapeutic signal delivering unit configured for being coupled to one or more ventricular electrodes for delivering one or more electrotherapeutic signals to said heart;
a sensing unit operatively couplable to at least one of said one or more ventricular electrodes and to a distant electrode implanted in said subject, said sensing unit being configured for:
  (i) sensing at least one non-local intra-cardiac electrocardiogram signal between a ventricular electrode and a distant electrode implanted in said subject; and
  (ii) sensing at least one locally sensed electrical signal from said ventricular electrode;
a processing unit operatively coupled to said at least one electrotherapeutic signal delivering unit and to said sensing unit, said processing unit being configured for:
  (i) controlling the operation of said electrotherapeutic signal delivering unit,
  (ii) receiving from said sensing unit signals representing said non-local intra-cardiac electrocardiogram signal and said locally sensed electrical signal,
  (iii) processing said non-local electrocardiogram signal and said locally sensed signal to detect a suspected ectopic electrical event within said cardiac beat cycle; and
  (iv) inhibiting the delivery of said electrotherapeutic signal to said heart upon detecting said suspected ectopic electrical event; and
a power source for providing power to said at least one electrotherapeutic unit, said sensing unit and said processing unit.

6. The device according to claim 5 wherein said distant electrode comprises at least part of an electrically conducting can of said device implanted in said subject.

7. The device according to claim 5 wherein said power source is selected from a power source disposed within said device and a power receiving device configured for receiving power wirelessly transmitted from an external power source disposed outside of said subject.

8. The device according to claim 5 wherein said at least one electrotherapeutic unit is selected from a pacing unit configured for performing at least biventricular pacing of said heart, a cardiac contractility modulating unit configured for delivering non-excitatory cardiac contractility modulating signals to said heart, and combinations thereof.

9. The device according to claim 5 further including a telemetry unit suitably coupled to said processing unit for telemetrically communicating signals between said device and a telemetry unit external to said device.

10. The device according to claim 5 wherein said processing unit is configured for recording at least one electrocardiogram signal of said subject, recording at least one locally sensed electrical signal from at least one ventricular electrode, processing said electrocardiogram signal and said at least one locally sensed signal to detect a suspected ectopic electrical event within a current cardiac cycle, and inhibiting the delivery of one or more of said electrotherapeutic signals to the heart upon detecting said suspected ectopic electrical event.

11. The device according to claim 5 wherein said processing unit is configured for differentially recording a first intracardiac electrocardiogram signal between a first ventricular electrode disposed at a first site of one or more ventricular sites and a distant electrode implanted in said subject, differentially recording a second intracardiac electrocardiogram signal between a second ventricular electrode disposed at a second site of said one or more ventricular sites and said distant electrode, recording a locally sensed third electrical signal from said first electrode and a locally sensed fourth electrical signal from said second electrode, processing said first electrocardiogram signal, said second electrocardiogram signal, said third signal and said fourth signal to detect a suspected ectopic electrical event within a cardiac beat cycle, and inhibiting the delivery of an electrotherapeutic signal to the heart upon detecting said suspected ectopic electrical event.

12. The device of claim 6, further comprising only a single lead with two electrode contacts, coupled to said sensing unit and providing all of said one or more ventricular electrodes.

13. The device of claim 5, further comprising a memory storing therein different decision and detection criteria for different heart rates and paced and non-paced beats.

14. The device of claim 5, further comprising a memory configured for recording therein between 30 and 150 milliseconds of data for each of said sensed signals.

15. A method for controlling the delivery of electrotherapeutic signals to a heart of a subject, the method comprising:
  applying one or more electrodes to one or more ventricular sites of said subject;
  recording at least one non-local electrocardiogram signal of said subject;
  recording at least one locally sensed electrical signal from said at least one ventricular electrode;
  processing said non-local electrocardiogram signal and said at least one locally sensed signal to detect a suspected ectopic electrical event within the current cardiac cycle; and
  inhibiting the delivery of one or more of said electrotherapeutic signals to the heart upon detecting said suspected ectopic electrical event.

16. The method according to claim 15 wherein said electrocardiogram signal is selected from,
  at least one unipolar intra-cardiac electrocardiogram signal recorded between at least one ventricular electrode disposed at a first site of said one or more ventricular sites and a distant electrode implanted in said subject, and
  at least one electrocardiogram signal recorded using one or more nonimplanted electrodes externally applied to said subject.

17. The method according to claim 15 wherein said current beat cycle is a paced beat cycle and said suspected ectopic electrical event is an ectopic event other than a pacing induced ventricular electrical activity.

18. The method according to claim 15 wherein said electrotherapeutic signals are selected from one or more ventricular pacing signals, one or more non-excitatory cardiac contractility modulating signals, and a combination thereof.

19. The method according to claim 15 wherein said at least one locally sensed electrical signal is a signal obtained by bipolar recording using a ventricular electrode.

20. The method according to claim 19 wherein said distant electrode comprises at least part of an electrically conducting can of a device implanted in said subject.

21. The method according to claim 15 wherein said processing comprises differentiating between an electrical event related to an arrhythmogenic atrium and an electrical event related to a suspected ectopic event selected from a distant ventricular ectopic beat, a premature ventricular contraction and a ventricular arrhythmic event, and wherein said inhibiting the delivery of one or more of said electrotherapeutic signals to the heart is performed upon detecting said suspected ectopic electrical event and is not performed upon the detection of said electrical event related to an arrhythmogenic atrium.

22. The method according to claim 15 wherein said processing comprises performing a template matching between at least a portion of said at least one electrocardiogram signal and a template for detecting an ectopic event based on morphological criteria of said electrocardiogram.

23. The method according to claim 22 wherein said template is selected from a fixed template and a dynamically adaptive template.

24. The method according to claim 22 wherein said template is a dynamically adaptive template and wherein said dynamically adaptive template is updated based on previously recorded electrocardiogram signals.

25. The method according to claim 22 wherein the result of said template matching comprises computing a value representing the degree of matching of the current sensed electrocardiogram signal to said template and using at least said value for deciding whether the delivery of said electrotherapeutic signals to the heart should be inhibited or not.

26. The method according to claim 22 wherein said detecting of said suspected ectopic electrical event is performed based on at least one additional test criterion or decision rule.

27. The method according to claim 26 wherein said at least one additional test criterion or decision rule is selected from an R-R interval based criterion, and a criterion based on the delay in the sensing of an electrical event by two differently positioned local sensing electrodes.

28. The method according to claim 15 wherein said processing comprises processing at least portions of said at least one electrocardiogram signal and at least portions of said at least one locally sensed electrical signal to detect an ectopic event based on one or more test criterion or decision rule.

29. The method of claim 15, wherein said inhibiting comprises allowing the delivery even if the heart is in atrial arrhythmia, if a suspected ventricular ectopic electrical event is not detected.

30. The method of claim 15 wherein said electrotherapeutic signals include one or more non-excitatory cardiac modulating signals.

31. The method of claim 15, wherein said processing detects electrical events in a single chamber regardless of electrical events in other chambers.

32. The method of claim 15, wherein said recordings and processing are performed within 100 milliseconds of said inhibiting.

33. The method of claim 15, wherein said recordings and processing are performed within and using electrocardiogram recording of between 30 and 150 milliseconds of said inhibiting.

34. The method of claim 15, wherein said processing of said non-local electrocardiogram is timed and uses data synchronized according to one or both of said local sensed electrical signal and an expected time of applying said electrotherapeutic signals.

35. The method of claim 15, wherein said processing of said non-local electrocardiogram is triggered by one or both of said local sensed electrical signal and an expected time of applying said electrotherapeutic signals.

36. The method of claim 15, wherein said distant electrode comprises a plurality of electrodes.

37. A method for controlling the delivery of electrotherapeutic signals to a heart of a subject, the method comprising:
 applying one or more electrodes to one or more ventricular sites of said subject;
 recording at least one non-local electrocardiogram signal of said subject;
 processing said non-local electrocardiogram signal responsive to the timing of an expected or sensed local event to detect a suspected ectopic electrical event within the current cardiac cycle; and
 modifying the delivery of one or more of said electrotherapeutic signals to the heart upon detecting said suspected ectopic electrical event.

38. The method according to claim 37, wherein said electrotherapeutic signals include bi-ventricular pacing signals.

39. The method of claim 37, wherein said recordings and processing are performed within and using electrocardiogram recording of between 30 and 150 milliseconds of said inhibiting.

40. The method of claim 37, wherein said recordings and processing are applied to data originating within a single ventricle

* * * * *